(12) United States Patent
Pachot et al.

(10) Patent No.: US 11,060,143 B2
(45) Date of Patent: Jul. 13, 2021

(54) METHOD FOR DIAGNOSIS AND/OR PROGNOSIS OF A SEPTIC SYNDROME

(75) Inventors: Alexandre Pachot, Sulignat (FR);
Guillaume Monneret, Lyons (FR);
Alain Lepape, Saint-Genis-Laval (FR)

(73) Assignee: BIOMERIEUX, Marcy l'Etoile (FR)

( * ) Notice: Subject to any disclaimer, the term of this patent is extended or adjusted under 35 U.S.C. 154(b) by 1351 days.

(21) Appl. No.: 11/794,690

(22) PCT Filed: Jan. 30, 2006

(86) PCT No.: PCT/FR2006/050070
§ 371 (c)(1),
(2), (4) Date: Jul. 3, 2007

(87) PCT Pub. No.: WO2006/079760
PCT Pub. Date: Aug. 3, 2006

(65) Prior Publication Data
US 2009/0208933 A1    Aug. 20, 2009

(30) Foreign Application Priority Data
Jan. 31, 2005   (FR) ...................................... 0550267

(51) Int. Cl.
*C12Q 1/6883* (2018.01)
*G01N 33/68* (2006.01)
*G01N 33/569* (2006.01)

(52) U.S. Cl.
CPC ..... *C12Q 1/6883* (2013.01); *G01N 33/56911* (2013.01); *G01N 33/6893* (2013.01); *C12Q 2600/118* (2013.01); *C12Q 2600/158* (2013.01); *G01N 2800/26* (2013.01)

(58) Field of Classification Search
None
See application file for complete search history.

(56) References Cited

U.S. PATENT DOCUMENTS

| 2004/0133352 A1* | 7/2004 | Bevilacqua ........ G01N 33/5088 702/19 |
| 2004/0191255 A1* | 9/2004 | Lillard, Jr. ............. C07K 16/24 424/145.1 |
| 2004/0191783 A1* | 9/2004 | Leclercq ............... C12Q 1/6837 506/16 |
| 2004/0241729 A1* | 12/2004 | Liew .................................. 435/6 |
| 2005/0037344 A1 | 2/2005 | Stuhlmuller et al. |

FOREIGN PATENT DOCUMENTS

| EP | 1 310 567 A2 | 5/2003 |
| WO | WO 2004/043236 A2 | 5/2004 |
| WO | WO 2004/087949 A2 | 10/2004 |
| WO | WO 2004/108957 A2 | 12/2004 |

OTHER PUBLICATIONS

GenBank Accession No. X72501 (NCBI Sep. 9, 1993).*
Joyce et al. (The journal of Biological Chemistry 2001 vol. 276 p. 11199).*
Cabioglu et al. (Arch Surg 2002 vol. 137 p. 1037).*
Cheung et al (Nature Genetics, 2003, vol. 33, pp. 422-425).*
Cobb et al (Crit Care Med 2002 vol. 30 p. 2711).*
"Affymetrix GeneChip Human Genome U133 Array Set HG-U133A," XP-002254749 GEO, Mar. 11, 2002.
Prucha et al., "Expression Profiling: Toward an Application in Sepsis Diagnostics," *Shock*, vol. 22, 2004, p. 29-33.
Johnson et al., "Gene Expression Profiles Differentiate Between Sterile SIRS and Early Sepsis," *Annals of Surgery*, vol. 245, No. 4, Apr. 2007, p. 611-621.
Ramilo et al., "Gene expression patterns in blood leukocytes discriminate patients with acute infections," *Blood*, vol. 109, No. 5, Mar. 1, 2007, p. 2066-2077.
Pachot et al., "Systemic transcriptional analysis in survivor and non-survivor septic shock patients: A preliminary study," *Immunology Letters*, vol. 106, 2006, p. 63-71.
Wong et al., "Genome-level expression profiles in pediatric septic shock indicate a role for altered zinc homeostasis in poor outcome," *Physiol Genomics*, vol. 30, Mar. 20, 2007, p. 146-155.
Shanley et al., "Genome-level longitudinal expression of signaling pathways and gene networks in pediatric septic shock," *Mol. Med.*, 2007.
Calvano et al., "A network-based analysis of systemic inflammation in humans," *Nature*, vol. 437, Oct. 13, 2005, p. 1032-1037.

* cited by examiner

*Primary Examiner* — Katherine D Salmon
(74) *Attorney, Agent, or Firm* — Oliff PLC

(57) ABSTRACT

The present invention relates to a method for the diagnosis/prognosis of a septic syndrome based on a biological sample from a patient, characterized in that it comprises the following steps:
a. biological material is extracted from the biological sample,
b. the biological material is brought into contact with at least one specific reagent that is selected from specific reagents for the target genes with a nucleic sequence having any one of SEQ ID Nos 1 to 28;
c. the expression of at least one of said target genes is determined.

14 Claims, 3 Drawing Sheets
Specification includes a Sequence Listing.

SEQUENCE LISTING

<160> NUMBER OF SEQ ID NOS: 34

<210> SEQ ID NO 1
<211> LENGTH: 3100
<212> TYPE: DNA
<213> ORGANISM: Homo sapiens

<400> SEQUENCE: 1
actcgtctct ggtaaagtct gagcaggaca gggtggctga ctggcagatc cagaggttcc    60

-continued

```
cttggcagtc cacgccaggc cttcaccatg gatcagttcc ctgaatcagt gacagaaaac    120
tttgagtacg atgatttggc tgaggcctgt tatattgggg acatcgtggt ctttgggact    180
gtgttcctgt ccatattcta ctccgtcatc tttgccattg gcctggtggg aaatttgttg    240
gtagtgtttg ccctcaccaa cagcaagaag cccaagagtg tcaccgacat ttacctcctg    300
aacctggcct tgtctgatct gctgtttgta gccactttgc ccttctggac tcactatttg    360
ataaatgaaa agggcctcca caatgccatg tgcaaattca ctaccgcctt cttcttcatc    420
ggcttttttg gaagcatatt cttcatcacc gtcatcagca ttgataggta cctggccatc    480
gtcctggccg ccaactccat gaacaaccgg accgtgcagc atggcgtcac catcagccta    540
ggcgtctggg cagcagccat tttggtggca gccccagt tcatgttcac aaagcagaaa    600
gaaaatgaat gccttggtga ctaccccgag gtcctccagg aaatctggcc cgtgctccgc    660
aatgtggaaa caaattttct tggcttccta ctcccctgc tcattatgag ttattgctac    720
ttcagaatca tccagacgct gttttcctgc aagaaccaca agaaagccaa agccattaaa    780
ctgatccttc tggtggtcat cgtgttttc ctcttctgga caccctacaa cgttatgatt    840
ttcctggaga cgcttaagct ctatgacttc tttcccagtt gtgacatgag gaaggatctg    900
aggctggccc tcagtgtgac tgagacggtt gcatttagcc attgttgcct gaatcctctc    960
atctatgcat tgctgggga aagttcaga agatacctttt accacctgta tgggaaatgc   1020
ctggctgtcc tgtgtgggcg ctcagtccac gttgatttct cctcatctga atcacaaagg   1080
agcaggcatg gaagtgttct gagcagcaat tttacttacc acacgagtga tggagatgca   1140
ttgctccttc tctgaaggga atcccaaagc cttgtgtcta cagagaacct ggagttcctg   1200
aacctgatgc tgactagtga ggaaagattt tgttgttat ttcttacagg cacaaaatga   1260
tggacccaat gcacacaaaa caaccctaga gtgttgttga gaattgtgct caaaatttga   1320
agaatgaaca aattgaactc tttgaatgac aaagagtaga catttctctt actgcaaatg   1380
tcatcagaac ttttttggttt gcagatgaca aaaattcaac tcagactagt ttagttaaat   1440
gagggtggtg aatattgttc atattgtggc acaagcaaaa gggtgtctga gccctcaaag   1500 tgagggaaa ccagggcctg agccaagcta gaattccctc tctctgactc tcaaatcttt   1560
tagtcattat agatccccca gactttacat gacacagctt tatcaccaga gagggactga   1620
cacccatgtt tctctggccc caagggaaaa ttcccaggga agtgctctga taggccaagt   1680
ttgtatcagg tgcccatccc tggaaggtgc tgttatccat ggggaaggga tatataagat   1740
ggaagcttcc agtccaatct catggagaag cagaaataca tatttccaag aagttggatg   1800
ggtgggtact attctgatta cacaaaacaa atgccacaca tcaccctac catgtgcctg   1860 atccagcctc tccctgatt acaccagcct cgtcttcatt aagccctctt ccatcatgtc   1920
cccaaacctg caagggctcc ccactgccta ctgcatcgag tcaaaactca aatgcttggc   1980
ttctcatacg tccaccatgg ggtcctacca atagattccc cattgcctcc tccttcccaa   2040
aggactccac ccatcctatc agcctgtctc ttccatatga cctcatgcat ctccacctgc   2100
tcccaggcca gtaagggaaa tagaaaaacc ctgcccccaa ataagaaggg atggattcca   2160
accccaactc cagtagcttg ggacaaatca agcttcagtt cctggtctg tagaagaggg   2220 ataaggtacc tttcacatag agatcatcct ttccagcatg aggaactagc caccaactct   2280
tgcaggtctc aacccttttg tctgcctctt agacttctgc tttccacacc tgcactgctg   2340
tgctgtgccc aagttgtggt gctgacaaag cttggaagag cctgcaggtg ccttggccgc   2400
```

| | |
|---|---|
| gtgcatagcc cagacacaga agaggctggt tcttacgatg gcacccagtg agcactccca | 2460 |
| agtctacaga gtgatagcct tccgtaaccc aactctcctg gactgccttg aatatcccct | 2520 |
| cccagtcacc ttgtgcaagc ccctgcccat ctgggaaaat accccatcat tcatgctact | 2580 |
| gccaacctgg ggagccaggg ctatgggagc agcttttttt tccccctag aaacgtttgg | 2640 |
| aacaatgtaa aactttaaag ctcgaaaaca attgtaataa tgctaaagaa aaagtcatcc | 2700 |
| aatctaacca catcaatatt gtcattcctg tattcacccg tccagacctt gttcacactc | 2760 |
| tcacatgttt agagttgcaa tcgtaatgta cagatggttt tataatctga tttgttttcc | 2820 |
| tcttaacgtt agaccacaaa tagtgctcgc tttctatgta gtttggtaat tatcatttta | 2880 |
| gaagactcta ccagactgtg tattcattga agtcagatgt ggtaactgtt aaattgctgt | 2940 |
| gtatctgata gctctttggc agtctatatg tttgtataat gaatgagaga ataagtcatg | 3000 |
| ttccttcaag atcatgtacc ccaatttact tgccattact caattgataa acatttaact | 3060 |
| tgtttccaat gtttagcaaa tacatatttt atagaacttc | 3100 |

<210> SEQ ID NO 2
<211> LENGTH: 783
<212> TYPE: DNA
<213> ORGANISM: Homo sapiens

<400> SEQUENCE: 2

| | |
|---|---|
| atgcagagga tctcctccct catccatctc tctctcttct gggcaggagt catgtcagcc | 60 |
| attgagttgg tgcctgaaca ccaaacagtg cctgtgtcaa taggggtccc tgccacccctc | 120 |
| aggtgctcca tgaaaggaga agcgatcggt aactactata tcaactggta caggaagacc | 180 |
| caaggtaaca caatgacttt catataccga gaaaaggaca tctatggccc tggtttcaaa | 240 |
| gacaatttcc aaggtgacat tgatattgca agaacctggc tgtacttaa gatacttgca | 300 |
| ccatcagaga gagatgaagg gtcttactac tgtgcctgtg acaccttggg gatgggggg | 360 |
| gaatacaccg ataaactcat ctttggaaaa ggaacccgtg tgactgtgga accaagaagt | 420 |
| cagcctcata ccaaaccatc cgttttttgtc atgaaaaatg aacaaatgt cgcttgtctg | 480 |
| gtgaaggaat ctaccccaa ggatataaga ataaatctcg tgtcatccaa gaagataaca | 540 |
| gagtttgatc ctgctattgt catctctccc agtgggaagt acaatgctgt caagcttggt | 600 |
| aaatatgaag attcaaattc agtgacatgt tcagttcaac acgacaataa aactgtgcac | 660 |
| tccactgact ttgaagtgaa gacagattct acagatcacg taaaaccaaa ggaaactgaa | 720 |
| aacacaaagc aaccttcaaa gagctgccat aaacccaaag ccatagttca taccgagaag | 780 |
| taa | 783 |

<210> SEQ ID NO 3
<211> LENGTH: 5191
<212> TYPE: DNA
<213> ORGANISM: Homo sapiens

<400> SEQUENCE: 3

| | |
|---|---|
| gcggccgcgg gctctcgcgg ggcggcgacg ccgcggggag gatgctgctt gccgcgcccg | 60 |
| cgtcctcacc gtcctcccgg gccgcctgct ggggctttgt tgtggcccgg acgccgcggg | 120 |
| ccaccccctg aagtcgcctg ccgccgccgc cgccgcacct agcggacggg cgggcgggcg | 180 |
| cgcgtgtgcc caggagtgcg cgcctgtcgc ggtggtgggt gcaggactgg acccacgggc | 240 |
| ccattgtgcg cccgccgcg gcagccagga ccatgtgggt gaaccggag gaggtgttgc | 300 |
| tggccaacgc gctgtggatc accgagaggg ccaacccata cttcatcctg cagcggagga | 360 |

```
agggccacgc cggcgatgga ggcggcggcg gcggactggc gggcctgctg gtgggtaccc    420
ttgatgttgt gttggactcc agcgcccggg tcgctcctta ccgaatcttg taccagactc    480
cagactccct ggtctactgg accatcgcct gtggtggttc caggaaagaa atcactgaac    540
actgggaatg gcttgagcaa aatctcttgc agacactctc catctttgaa aatgagaatg    600
atatcaccac atttgtgaga ggaaaaatac agggcatcat tgcagaatac aacaaaatca    660
atgatgtaaa ggaagatgat gacacggaga agtttaaaga agccattgtg aaatttcata    720
ggctgtttgg gatgccagag gaagagaaac tcgtcaacta ttactcttgc agctattgga    780
aggggaaggt cccccgtcag ggttggatgt acctcagcat taaccacctt tgcttttatt    840
cttttcttat gggaagggaa gcgaaactgg tcatccggtg ggtagacatc actcagctcg    900
agaagaatgc caccctgctt ctgcctgatg tgatcaaagt gagcacacgg tccagtgagc    960
atttcttctc tgtattcctc aacatcaacg agaccttcaa gttaatggag cagcttgcca   1020
acatagccat gaggcaactc ttagacaatg agggatttga acaagatcga tccctgccca   1080
aactcaaaag gaaatctcct aaaaagtgt ctgctctaaa acgtgatctt gatgccaggg   1140
caaagagtga gagataccgt gcacttttcc ggctgcccaa agatgaaaaa ttagatggcc   1200
acacagactg cactctctgg actccattta acaaaatgca cattttgggg cagatgtttg   1260
tgtccacaaa ttcatctgt tttaccagca aggaggagaa cttatgtagc ctcattatcc   1320
cgctccgtga ggtgacaatt gtggaaaagg cagacagctc cagtgtgctc cccagtccct   1380
tatccatcag cacccgaaac aggatgacct tcctatttgc caacttgaaa gatagagact   1440
ttctagtgca gaggatctca gatttcctgc aacagactac ttccaaaata tattctgaca   1500
aggagtttgc aggaagttac aacagttcag atgatgaggt gtactctcga cccagcagcc   1560
tcgtctcctc cagcccccag agaagcacga gctctgatgc tgatggagag cgccagttta   1620
acctaaatgg caacagcgtc cccacagcca cacagaccct gatgaccatg tatcggcggc   1680
ggtctcccga ggagttcaac ccgaaattgg ccaaagagtt tctgaaagag caagcctgga   1740
agattcactt tgctgagtat gggcaaggga tctgcatgta ccgcacagag aaaacgcggg   1800
agctggtgtt gaagggcatc ccggagagca tgcgtgggga gctctggctg ctgctgtcag   1860
gtgccatcaa tgagaaggcc acacatcctg ggtactatga agacctagtg gagaagtcca   1920 tgggaagta taatctcgcc acggaggaga ttgagaggga tttacaccgc tcccttccag   1980
aacacccagc ttttcagaat gaaatgggca ttgctgcact aaggagagtc ttaacagctt   2040
atgcttttcg aaatcccaac ataggtatt gccaggccat gaatattgtc acttcagtgc   2100
tgctgcttta tgccaaagag gaggaagctt tctggctgct tgtggctttg tgtgagcgca   2160
tgctcccaga ttactacaac accagagttg tgggtgcact ggtggaccaa ggtgtctttg   2220
aggagctagc acgagactac gtcccacagc tgtacgactg catgcaagac ctgggcgtga   2280
tttccaccat ctccctgtct tggttcctca cactatttct cagtgtgatg ccttttgaga   2340
gtgcagttgt ggttgttgac tgtttcttct atgaaggaat taaagtgata ttccagttgg   2400
ccctagctgt gctggatgca aatgtggaca aactgttgaa ctgcaaggat gatgggagg   2460 ccatgaccgt tttgggaagg tatttagaca gtgtgaccaa taaagacagc acactgcctc   2520
ccattcctca cctccactcc ttgctcagcg atgatgtgga accttaccct gaggtagaca   2580 tcttagact catcagaact tcctacgaga aattcggaac tatccgggca gatttgattg   2640
aacagatgag attcaaacag agactgaaag tgatccagac gctggaggat actacgaaac   2700
```

-continued

```
gcaacgtggt acgaaccatt gtgacagaaa cttcctttac cattgatgag ctggaagaac    2760
tttatgctct tttcaaggca gaacatctca ccagctgcta ctggggcggg agcagcaacg    2820
cgctggaccg gcatgacccc agcctgccct acctggaaca gtatcgcatt gacttcgagc    2880
agttcaaggg aatgtttgct cttctctttc cttgggcatg tggaactcac tctgacgttc    2940
tggcctcccg cttgttccag ttattagatg aaaatggaga ctctttgatt aacttccggg    3000
agtttgtctc tgggctaagt gctgcatgcc atggggacct cacagagaag ctcaaactcc    3060
tgtacaaaat gcacgtcttg cctgagccat cctctgatca agatgaacca gattctgctt    3120
ttgaagcaac tcagtacttc tttgaagata ttaccccaga atgtacacat gttgttggat    3180
tggatagcag aagcaaacag ggtgcagatg atggctttgt tacggtgagc ctaaagccag    3240
acaaagggaa gagagcaaat tcccaagaaa atcgtaatta tttgagactg tggactccag    3300
aaaataaatc taagtcaaag aatgcaaagg atttacccaa attaaatcag gggcagttca    3360
ttgaactgtg taagacaatg tataacatgt tcagcgaaga ccccaatgag caggagctgt    3420
accatgccac ggcagcagtg accagcctcc tgctggagat tggggaggtc ggcaagttgt    3480
tcgtggccca gcctgcaaag gaggacaagc tgcactgcga ggacatcgga gaggacacgg    3540
tcctggtgcg gagcggccag ggcacggcgg cactgccccg gagcaccggc ctggaccggg    3600
actgggccat caccttcgag cagttcctgg cctccctctt aactgagcct gccctggtca    3660
agtactttga caagcccgtg tgcatgatgg ccaggattac cagtgcaaaa acatccggga    3720
tgatgggcaa gcccctcacc tcggccagtg actatgaaat ctcggccatg tccggctgac    3780
acgggcgcct tcccggggga gtgggaggaa agggagggga gggattttt atgttcttct    3840 gtgttgagtt ttttctttct ttctttaaa ttaaatattt attagtacct ggcttgaagc    3900
ctagtgtttt cataatgtaa ttcaatgaaa actgttggag aaatatttaa acacctcaat    3960
gtaggtacat tacactcttg ttgcggggag gggatttacc agaatacagt ttatttcgtg    4020
aattctaaaa aacaaaaaga tgaatctgtc agtgatatgt gtgtattata acttattaat    4080
cttgctgttg agctgtatac atggtttaaa aaatagtact gtttaatgct aagtaaggca    4140
gcagtcattt gtgtattcag cttttttaaa taaaattaga gctgtaagga aaatgaaaag    4200
ccacaaatgc aagactgttc ttaaatggaa ggcatagtca gcgagggtaa atcctatacc    4260
actttaggaa gtattaaaaa tatttttaag atttgaaata tatttcatag aagtcctcta    4320
ttcaaaatca tattccacag atgttcccct tcaagggaa acatttggg gttctaaaca    4380 gttatgaaag taagtgattt ttacatgatt ccagaataac acttgtattg accaatttaa    4440
acagatacca gaccaattt gcatttaaga aattgttctg attatttacg tcaactcatt    4500
agaattcagt gaaagtaac agtctttgt cacagagaat ctgaaagtag cagcaaagac    4560
agagggctca tgacaggttt ttgcttttgc tttgcttttg tttttgaaag agtaaaagta    4620
ctgatgcttc tgatactgga tgtttagctt cttactgcaa aaacataagt aaaacagtca    4680
actttaccat ttccgtattc tccatagatt gaagaaattt ataccacata tcgcatatga    4740
ccatctttcc atcaaatcaa tgtagagata atgtaaactg aaaaaaaatc tgcaagataa    4800
tgtaactgaa tgttttaaaa acagaacttg tcactttata taaagaata gtatgctcta    4860 tttcctgaat ggatgtggaa atgaaagcta gcgcacctgc actttgaatt cttgcttctt    4920
ttttattact gttatgattt tgcttttac agatgttgga cgattttttc ttctgattgt    4980
tgaattcata atcatggtct catttccttt gcttctttgg aatatttctt tcaacacatt    5040
cctttatttt attatacatt gtgtcctttt tttagctatt gctgctgttg ttttttattc    5100
```

```
tatttacagg atgattttta aactgtcaaa tgaagtagtg ttaacctcaa ataggctaaa      5160
tgtgaacaaa taaaatacag caaatactca g                                    5191

<210> SEQ ID NO 4
<211> LENGTH: 5521
<212> TYPE: DNA
<213> ORGANISM: Homo sapiens

<400> SEQUENCE: 4
cgccccgcat cgtgcccggc cccgtcgcgg agatcccgga cgaccgtcgc gggttgatgg        60
tcgcattcca gatgtaaaca gcttcagaag cctgacggtc atatggtaga atcactgtgg       120
actgagaccc acctttctag acctgaagcc caggaggagg aagaggaggc tggttggtac       180
catgggcata atgctctgaa tcctagtctc tcacctagta tgtgagcagt ccctgcagat       240
ggcccatttg gagatcttga caaagcctct tctgtttcca atggggtttt tggcgcattc       300
tcacagactt agatgaaact gtgatggcca ccgcaggggg caggtgctga catcgtcccc       360
agccctgtgg ctgttcatcc ggacatcatt tccaacctca atatctaaat gccacagtgc       420
tcttggagca agttgggctg ggaccactg ttgcctttta agaccataaa accatgggaa        480
acgcagaaag tcaacatgta gagcacgagt tttatggaga aaagcatgcc agcctggggc       540
gcaacgacac ttcccgctcc ctgcgcctct cgcacaagac gcggaggacc aggcacgctt       600
cctcggggaa ggtgatccac aggaactccg aagtgagcac ccgatccagc agcacccccca      660 gcatccccca gtccctggct gaaaatggcc tggagcccct ctcccaagat ggtaccctag       720
aagacttcgg gagcccatc tgggtggacc gagtggacat gggcttgaga cctgtgtctt        780
acactgactc ttctgtcact cccagcgtag acagcagcat cgtcctcaca gcagcctctg       840
tgcagagcat gccagacact gaggagagca ggctttacgg ggatgacgct acatatttgg       900
ctgagggagg caggaggcag cattcctata catccaatgg gcccactttc atggagacgg       960
cgagctttaa gaagaaacgc tccaaatctg cagacatctg gcgggaggac agcctggaat      1020
tctcactctc tgatctgagc caagaacatt taacaagcaa cgaagaaatc ttgggttccg      1080
ccgaagagaa ggactgcgag gaggctcggg ggatggaaac gcgggcgagt ccgcggcagc      1140
tcagcacctg tcagagagcc aattccttgg gtgacttgta tgctcagaaa aactctggag      1200
tgacagcaaa catggggccg gggagcaaat ttgcaggcta ctgtcggaat ttggtgtctg      1260
atattcccaa tcttgcaaac cataagatgc caccagctgc tgctgaagag actcctccgt      1320
acagtaatta taacacactt ccctgtagga aatctcactg tctctctgaa ggtgccacca      1380
acccacaaat tagccatagc aacagcatgc aaggcagaag agctaaaaca actcaggatg      1440
ttaatgcagg cgagggcagt gagtttgcag acagtgggat tgaaggggcc actaccgaca      1500
cggacctcct gtccaggcga tctaatgcca ccaactccag ctactcaccc accacaggcc      1560
gggcctttgt gggcagcgac agcggcagca gctccaccgg ggatgcggct cgtcagggg       1620 tgtacgagaa cttccggcgg gagctggaga tgagcaccac caacagcgag agcctggagg      1680
aggccggctc tgcgcacagc gatgagcaga gcagccgcac cctgagctct ccgggccagt      1740
cggacatcct gctgaccgcc gcacagggca cggtgcgcaa ggccggcgcc ctggccgtca      1800
agaacttcct ggtgcacaag aagaacaaga aggtggagtc agccacccgg aggaagtgga      1860
agcactactg ggtgtccctg aaaggatgca cgctattttt ctacgagagc gacgcaggt       1920 ctgggataga ccacaacagc atccccaaac acgccgtctg ggtggagaac agcattgtgc      1980
```

-continued

```
aggctgtgcc tgagcacccc aagaaggact ttgtcttctg cctcagcaat tccctgggtg    2040
atgccttcct ttttcagacc actagccaga cggagcttga aaactggatc accgccatcc    2100
actctgcctg cgccactgcg gtcgcgaggc accaccacaa ggaagacacg ctccgactcc    2160
tgaaatcaga gatcaaaaaa ctggaacaga gattgacatg gatgaaaag atgaagaaaa     2220 tgggtgaaat gcagctgtct tcagtcactg actcaaagaa aaagaaaaca atattagatc    2280
agatctttgt ctgggagcaa aatctcgagc agttccaaat ggacctgttt cgtttccgct    2340
gttatttagc cagccttcag ggtggggagc tgccaaaccc caaaaggctt ctcgcttttg    2400
caagtcgacc aacgaaagtg gccatgggcc gccttggaat cttttcggta tcatcgtttc    2460
atgccctggt ggcagcacgc actggtgaaa ctggagtgag aagacgtact caggccatgt    2520
ccagatccgc gagcaagcga aggagcaggt tttcttctct gtggggtctg gatactacct    2580
ccaaaaagaa gcagggacgg ccaagcatca atcaggtgtt tggagaggga accgaagctg    2640
taaagaaatc tttagaggga atatttgatg acattgttcc agatggcaag agggagaaag    2700
aagtggtctt acctaacgtt caccagcaca accctgactg cgacatttgg gtccacgagt    2760
atttcactcc atcctggttc tgtctgccca ataatcagcc tgccctgacg gtcgtccggc    2820
caggcgacac tgcacgggac accctggagc tgatttgcaa gacacatcaa ctggatcatt    2880
ctgctcatta cctgcgcctg aaatttctaa tagaaaacaa aatgcagctc tatgttccac    2940
agcccgagga agacatctat gagctgctgt acaaagaaat tgaaatctgt ccaaaagtca    3000
ctcacagcat ccacattgag aagtcagata cagctgctga tacttacggg ttttcacttt    3060
cttctgtgga agaagatggt attcgaaggc tgtacgtgaa tagtgtgaag gaaaccggtt    3120
tagcttccaa gaaaggcctg aaagcaggag atgagattct tgagatcaat aatcgtgctg    3180
ctgacgccct gaactcttct atgctcaaag atttcctctc acaaccctcg ctgggcctcc    3240
tggtgaggac ctaccccgag ctggaggaag agtggagct gctggaaagc ccgccccacc     3300
gagtggacgg ccctgccgac cttgacgaga gcccctcgc cttctcacc agcaacccag      3360 ggcacagcct ttgcagcgag cagggcagca gtgctgagac cgctccagag gagaccgagg    3420
ggccagactt ggaatcctca gatgagactg atcacagcag caagagtaca gaacaggtgg    3480
ccgcattttg ccgcagtttg catgagatga cccctctga ccagaaccca tctcctcagg     3540
actccacggg gcctcagctg gcgaccatga acaactctc ggatgcagat aacgtgcgca     3600
aggtgatctg cgagctcctg gagacggagc gcacctacgt gaaggattta aactgtctta    3660
tggagagata cctaaagcct cttcaaaaag aaactttct cacccaggat gagcttgacg     3720
tgctttttgg aaatttaacg gaaatggtag agtttcaagt agaattcctt aaaactctag    3780
aagatggagt gagactggta cctgatttgg aaaagcttga gaaggttgat caatttaaga    3840
aagtgctgtt ctctctgggg ggatcattcc tgtattatgc tgaccgcttc aagctctaca    3900
gtgccttctg cgccatccac acaaaagttc ccaaggtcct ggtgaaagcc aagacagaca    3960
cggctttcaa ggcattcttg gatgcccaga acccgaagca gcagcactca tccacgctgg    4020
agtcgtacct catcaagccc atccagagga tcctcaagta cccacttctg ctcagggagc    4080
tgttcgccct gaccgatgcg gagagcgagg agcactacca cctggacgtg gccatcaaga    4140
ccatgaacaa ggttgccagt cacatcaatg agatgcagaa aatccatgaa gagtttgggg    4200
ctgtgtttga ccagctgatt gctgaacaga ctggtgagaa aaagaggtt gcagatctga    4260 gcatgggaga cctgcttttg cacactaccg tgatctggct gaacccgccg gcctcgctgg    4320
gcaagtggaa aaaggaacca gagttggcag cattcgtctt caaaactgct gtggtccttg    4380
```

```
tgtataaaga tggttccaaa cagaagaaga aacttgtagg atctcacagg ctttccattt    4440
atgaggactg ggacccctte agatttcgac acatgatccc cacggaagcg ctgcaggttc    4500
gagctttggc gagtgcagat gcagaggcaa atgccgtgtg tgaaattgtc catgtaaaat    4560
ccgagtctga agggaggccg agagggtct ttcacttgtg ctgcagctcc ccagagagcc     4620
gaaaggattt cctaaaggct gtgcattcaa tcctgcgtga taagcacaga agacagctcc    4680
tcaaaaccga gagccttccc tcatcccagc aatatgtccc ttttggaggc aaaagattgt    4740
gtgcactgaa gggggccagg ccggccatga gcagggcagt gtctgcccca agcaagtctc    4800
ttgggaggag gaggcggcgg ctggctcgaa acaggtttac cattgattct gatgccgtct    4860
ccgcaagcag cccggagaaa gagtcccagc agcccccgg tggtggggac actgaccgat     4920
gggtagagga gcagtttgat cttgctcagt atgaggagca agatgacatc aaggagacag    4980
acatcctcag tgacgatgat gagttctgtg agtccgtgaa gggtgcctca gtggacagag    5040
acctgcagga gcggcttcag gccacctcca tcagtcagcg ggaaagaggc cggaaaaccc    5100
tggatagtca cgcgtcccgc atggcacagc tcaagaagca agctgccctg tcggggatca    5160
atggaggcct ggagagcgca agcgaggaag tcatttgggt taggcgtgaa gactttgccc    5220
cctccaggaa actgaacact gagatctgac tgcgtcacct gccccgtaga aatgtgtgt     5280 agatacttcc tgccctaact ctgcccaccc tcctgtaccg tcgacaagaa tgtcccctta    5340
ggtcgcgctc ttgcacacac ggttttggca gctgacttgg ttctgaagcc atgtagccac    5400
ccaactttgt cattttcaac aacatcagaa agaattgatc agaatcccaa ataaaaccca    5460
aaagtgtcta atgtattcat tcattagcta actaaaagcc caaaaagac aagcaccca      5520 g                                                                    5521

<210> SEQ ID NO 5
<211> LENGTH: 1498
<212> TYPE: DNA
<213> ORGANISM: Homo sapiens

<400> SEQUENCE: 5
accaaacctc ttcgaggcac aaggcacaac aggctgctct gggattctct tcagccaatc      60
ttcattgctc aagtgtctga agcagccatg gcagaagtac ctgagctcgc cagtgaaatg     120
atggcttatt acagtggcaa tgaggatgac ttgttctttg aagctgatgg ccctaaacag     180
atgaagtgct ccttccagga cctggacctc tgccctctgg atggcggcat ccagctacga     240
atctccgacc accactacag caagggcttc aggcaggccg cgtcagttgt tgtggccatg     300
gacaagctga ggaagatgct ggttccctgc ccacagacct tccaggagaa tgacctgagc     360
accttctttc ccttcatctt tgaagaagaa cctatcttct tcgacacatg ggataacgag     420
gcttatgtgc acgatgcacc tgtacgatca ctgaactgca cgctccggga ctcacagcaa     480
aaaagcttgg tgatgtctgg tccatatgaa ctgaaagctc tccacctcca gggacaggat     540
atggagcaac aagtggtgtt ctccatgtcc tttgtacaag agaagaaag taatgacaaa      600 atacctgtgg ccttgggcct caaggaaaag aatctgtacc tgtcctgcgt gttgaaagat     660
gataagccca ctctacagct ggagagtgta gatcccaaaa attacccaaa gaagaagatg     720
gaaaagcgat tgtcttcaa caagatagaa atcaataaca agctggaatt tgagtctgcc      780
cagttccccc actggtacat cagcacctct caagcagaaa acatgccgt cttcctggga     840 gggaccaaag gcggccagga tataactgac ttcaccatgc aatttgtgtc ttcctaaaga    900
```

| | |
|---|---|
| gagctgtacc cagagagtcc tgtgctgaat gtggactcaa tccctagggc tggcagaaag | 960 |
| ggaacagaaa ggttttttgag tacggctata gcctggactt tcctgttgtc tacaccaatg | 1020 |
| cccaactgcc tgccttaggg tagtgctaag aggatctcct gtccatcagc caggacagtc | 1080 |
| agctctctcc tttcagggcc aatcccccagc cctttttgttg agccaggcct ctctcacctc | 1140 |
| tcctactcac ttaaagcccg cctgacagaa accacggcca catttggttc taagaaaccc | 1200 |
| tctgtcattc gctcccacat tctgatgagc aaccgcttcc ctatttattt atttatttgt | 1260 |
| ttgtttgttt tattcattgg tctaatttat tcaaggggg caagaagtag cagtgtctgt | 1320 |
| aaaagagcct agttttttaat agctatgaa tcaattcaat ttggactggt gtgctctctt | 1380 |
| taaatcaagt cctttaatta agactgaaaa tatataagct cagattattt aaatgggaat | 1440 |
| atttataaat gagcaaatat catactgttc aatggttctg aaataaactt cactgaag | 1498 |

<210> SEQ ID NO 6
<211> LENGTH: 1245
<212> TYPE: DNA
<213> ORGANISM: Homo sapiens

<400> SEQUENCE: 6

| | |
|---|---|
| cgggcgtgta acccacgggt gcgcgcccac gaccgccaga ctcgagcagt ctctggaaca | 60 |
| cgctgcgggg ctcccgggcc tgagccaggt ctgttctcca cgcaggtgtt ccgcgcgccc | 120 |
| cgttcagcca tgtcgtccgg catccatgta gcgctggtga ctggaggcaa caagggcatc | 180 |
| ggcttggcca tcgtgcgcga cctgtgccgg ctgttctcgg gggacgtggt gctcacggcg | 240 |
| cgggacgtga cgcggggcca ggcggccgta cagcagctgc aggcggaggg cctgagcccg | 300 |
| cgcttccacc agctggacat cgacgatctg cagagcatcc gcgccctgcg cgacttcctg | 360 |
| cgcaaggagt acggggggcct ggacgtgctg gtcaacaacg cgggcatcgc cttcaaggtt | 420 |
| gctgatccca caccctttca tattcaagct gaagtgacga tgaaaacaaa tttctttggt | 480 |
| acccgagatg tgtgcacaga attactccct ctaataaaac cccaagggag agtggtgaac | 540 |
| gtatctagca tcatgagcgt cagagccctt aaaagctgca gcccagagct gcagcagaag | 600 |
| ttccgcagtg agaccatcac tgaggaggag ctggtgggc tcatgaacaa gtttgtggag | 660 |
| gatacaaaga agggagtgca ccagaaggag ggctggccca gcagcgcata cggggtgacg | 720 |
| aagattggcg tcaccgttct gtccaggatc cacgccagga aactgagtga gcagaggaaa | 780 |
| ggggacaaga tcctcctgaa tgcctgctgc ccagggtggg tgagaactga catggcggga | 840 |
| cccaaggcca ccaagagccc agaagaaggt gcagagaccc ctgtgtactt ggccccttttg | 900 |
| cccccagatg ctgagggtcc ccatggacaa tttgtttcag agaagagagt tgaacagtgg | 960 |
| tgagctgggc tcacagctcc atccatgggc cccatttttgt accttgtcct gagttggtcc | 1020 |
| aaagggcatt tacaatgtca taaatatcct tatataagaa aaaaaatgat ctcttatcaa | 1080 |
| ttagcactca ctaatgtact actaattgag caacctacgc actcagttga ctacgtaaat | 1140 |
| ctgtcaggtc ttttgtgatt tcctctgatg caggagagga aaaattgtaa ttgatgaaaa | 1200 |
| taatgaatga aaatcaacag atgaataaat ggttctttat aagtg | 1245 |

<210> SEQ ID NO 7
<211> LENGTH: 2460
<212> TYPE: DNA
<213> ORGANISM: Homo sapiens

<400> SEQUENCE: 7

| | |
|---|---|
| gtgtggaaca tgccttcacc acctccagct tctgctgccg gaggctgcac ccacctgtgc | 60 |

```
ccatggcctg cacaggccca tcacttccta gcgccttcga cattctaggt gcagcaggcc    120
aggacaagct cttgtatctg aagcacaaac tgaagacccc acgcccaggc tgccaggggc    180
aggacctcct gcatgccatg gttctcctga agctgggcca ggaaactgag gccaggatct    240
ctctagaggc attgaaggcc gatgcggtgg cccggctggt ggcccgccag tgggctggcg    300
tggacagcac cgaggaccca gaggagcccc cagatgtgtc ctgggctgtg cccgcttgt     360 accacctgct ggctgaggag aagctgtgcc ccgcctcgct gcgggacgtg gcctaccagg    420
aagccgtccg caccctcagc tccagggacg accaccggct gggggaactt caggatgagg    480
cccgaaaccg gtgtgggtgg gacattgctg gggatccagg gagcatccgg acgctccagt    540
ccaatctggg ctgcctccca ccatcctcgg ctttgccctc tggaccagg agcctcccac     600 gccccattga cggtgtttcg gactggagcc aagggtgctc cctgcgatcc actggcagcc    660
ctgcctccct ggccagcaac ttggaaatca gccagtcccc taccatgccc ttcctcagcc    720
tgcaccgcag cccacatggg cccagcaagc tctgtgacga ccccaggcc agcttggtgc      780 ccgagcctgt ccccggtggc tgccaggagc ctgaggagat gagctggccg ccatcggggg    840
agattgccag cccaccagag ctgccaagca gcccacctcc tgggcttccc gaagtggccc    900
cagatgcaac ctccactggc ctccctgata ccccgcagc tccagaaacc agcaccaact      960
acccagtgga gtgcaccgag gggtctgcag gcccccagtc tctccccttg cctattctgg   1020
agccggtcaa aaacccctgc tctgtcaaag accagacgcc actccaactt tctgtagaag   1080
ataccacctc tccaaatacc aagccgtgcc cacctactcc caccacccca gaaacatccc   1140
ctcctcctcc tcctcctcct ccttcatcta ctccttgttc agctcacctg accccctcct   1200
ccctgttccc ttcctccctg gaatcatcat cggaacagaa attctataac tttgtgatcc   1260
tccacgccag ggcagacgaa cacatcgccc tgcgggttcg ggagaagctg gaggcccttg   1320
gcgtgcccga cggggccacc ttctgcgagg atttccaggt gccggggcgc ggggagctga   1380
gctgcctgca ggacgccata gaccactcag cttttcatcat cctacttctc acctccaact   1440
tcgactgtcg cctgagcctg caccaggtga accaagccat gatgagcaac ctcacgcgac   1500
aggggtcgcc agactgtgtc atccccttcc tgccctggga gagctcccg gcccagctca    1560 gctccgacac ggccagcctg ctctccgggc tggtgcggct ggacgaacac tcccagatct   1620
tcgccaggaa ggtggccaac accttcaagc cccacaggct tcaggcccga aaggccatgt   1680
ggaggaagga acaggacacc cgagccctgc gggaacagag ccaacacctg gacggtgagc   1740
ggatgcaggc ggcggcactg aacgcagcct actcagccta cctccagagc tacttgtcct   1800
accaggcaca gatggagcag ctccaggtgg cttttgggag ccacatgtca tttgggactg   1860
gggcgcccta tgggctcga atgccctttg gggccaggt gccctggga gccccgccac      1920 ccttttccca ttggccgggg tgccgcagc cgccacccct gcacgcatgg caggctggca   1980 ccccccacc gccctcccca cagcagcag cttttccaca gtcactgccc ttcccgcagt     2040
ccccagcctt ccctacggcc tcacccgcac cccctcagag cccagggctg caaccctca    2100 ttatccacca cgcacagatg gtacagctgg ggctgaacaa ccacatgtgg aaccagagag   2160
ggtcccaggc gcccgaggac aagacgcagg aggcagaatg accgcgtgtc cttgcctgac   2220
cacctgggga acacccctgg acccaggcat cggccaggac cccatagagc accccggtct   2280
gccctgtgcc ctgtggacag tgaagatga ggtcatctgc cactttcagg acattgtccg    2340 ggagccctc atttaggaca aaacgggcgc gatgatgccc tggctttcag ggtggtcaga    2400
```

```
actggatacg gtgtttacaa ttccaatctc tctatttctg ggtgaagggt cttggtggtg    2460
```

<210> SEQ ID NO 8
<211> LENGTH: 2650
<212> TYPE: DNA
<213> ORGANISM: Homo sapiens

<400> SEQUENCE: 8

```
gccgcgctgg tggcggcggc gcgtcgttgc agttgcgcca tctgtcagga gcggagccgg     60
cgaggagggg gctgccgcgg gcgaggagga ggggtcgccg cgagccgaag gccttcgaga    120
cccgcccgcc gccggcggc gagagtagag gcgaggttgt tgtgcgagcg gcgcgtcctc    180
tcccgcccgg gcgcgccgcg cttctcccag cgcaccgagg accgcccggg cgcacacaaa    240
gccgccgccc gcgccgcacc gccggcggc cgccgcccgc gccagggagg gattcggccg    300
ccgggccggg gacaccccgg cgccgccccc tcggtgctct cggaaggccc accggctccc    360
gggcccgccg ggacccccc ggagccgcct cggccgcgcc ggaggagggc ggggagagga    420
ccatgtgagt gggctccgga gcctcagcgc cgcgcagttt ttttgaagaa gcaggatgct    480
gatctaaacg tggaaaaaga ccagtcctgc ctctgttgta aagacatgt ggtgtatata    540
aagtttgtga tcgttggcgg acattttgga atttagataa tgggctgtgt gcaatgtaag    600
gataaagaag caacaaaact gacggaggag agggacggca gcctgaacca gagctctggg    660
taccgctatg gcacagaccc caccctcag cactacccca gcttcggtgt gacctccatc    720
cccaactaca caacttcca cgcagccggg ggccaaggac tcaccgtctt tggaggtgtg    780
aactcttcgt ctcatacggg gaccttgcgt acgagaggag gaacaggagt gacactcttt    840
gtggcccttt atgactatga agcacggaca gaagatgacc tgagttttca caaggagaa    900
aaatttcaaa tattgaacag ctcggaagga gattggtggg aagcccgctc cttgacaact    960
ggagagacag gttacattcc cagcaattat gtggctccag ttgactctat ccaggcagaa   1020
gagtggtact ttgaaaaact tggccgaaaa gatgctgagc gacagctatt gtcctttgga   1080
aacccaagag gtacctttct tatccgcgag agtgaaacca ccaaaggtgc ctattcactt   1140
tctatccgtg attgggatga tatgaaagga ccatgtca acattataa aattcgcaaa   1200
cttgacaatg gtggatacta cattaccacc cgggcccagt ttgaaacact tcagcagctt   1260
gtacaacatt actcagagag agctgcaggt ctctgctgcc gcctagtagt tccctgtcac   1320
aaagggatgc caaggcttac cgatctgtct gtcaaaacca agatgtctg ggaaatccct   1380
cgagaatccc tgcagttgat caagagactg ggaaatgggc agtttgggga agtatggatg   1440
ggtacctgga atggaaacac aaaagtagcc ataaagactc ttaaaccagg cacaatgtcc   1500
cccgaatcat tccttgagga agcgcagatc atgaagaagc tgaagcacga caagctggtc   1560
cagctctatg cagtggtgtc tgaggagccc atctacatcg tcaccgagta tatgaacaaa   1620
ggaagtttac tggatttctt aaaagatgga gaaggaagag ctctgaaatt accaaatctt   1680
gtggacatgc agcacaggt ggctgcagga atggcttaca tcgagcgcat gaattatatc   1740
catagagatc tgcgatcagc aaacattcta gtggggaatg gactcatatg caagattgct   1800
gacttcggat tggcccgatt gatagaagac aatgagtaca cagcaagaca aggtgcaaag   1860
ttccccatca gtggacggc cccgaggca gccctgtacg ggaggttcac aatcaagtct   1920
gacgtgtggt cttttggaat cttactcaca gagctggtca ccaaaggaag agtgccatac   1980
ccaggcatga acaaccggga ggtgctggag caggtggagc gaggctacag gatgcctgc   2040
ccgcaggact gccccatctc tctgcatgag ctcatgatcc actgctggaa aaaggaccct   2100
```

```
gaagaacgcc ccactttga gtacttgcag agcttcctgg aagactactt taccgcgaca    2160
gagccccagt accaacctgg tgaaaacctg taaggcccgg gtctgcggag agaggccttg    2220
tcccagaggc tgccccaccc ctccccatta gctttcaatt ccgtagccag ctgctcccca    2280
gcagcggaac cgcccaggat cagattgcat gtgactctga agctgacgaa cttccatggc    2340
cctcattaat gacacttgtc cccaaatccg aacctcctct gtgaagcatt cgagacagaa    2400
ccttgttatt tctcagactt tggaaaatgc attgtatcga tgttatgtaa aaggccaaac    2460
ctctgttcag tgtaaatagt tactccagtg ccaacaatcc tagtgctttc cttttttaaa    2520
aatgcaaatc ctatgtgatt ttaactctgt cttcacctga ttcaactaaa aaaaaaaaag    2580
tattattttc caaagtggc ctctttgtct aaaacaataa aattttttt catgttttaa     2640 caaaaaccaa                                                           2650

<210> SEQ ID NO 9
<211> LENGTH: 3726
<212> TYPE: DNA
<213> ORGANISM: Homo sapiens

<400> SEQUENCE: 9
cagcgctgct ccccgggcgc tcctcccgg gcgctcctcc ccaggcctcc cgggcgcttg      60
gatcccggcc atctccgcac ccttcaagtg ggtgtgggtg atttcctggc ggggggagca    120
gccaggtgag cccaagatgc tgctgcgctc gaagcctgcg ctgccgccgc cgctgatgct    180
gctgctcctg gggccgctgg gtcccctctc ccctggcgcc ctgccccgac ctgcgcaagc    240
acaggacgtc gtggacctgg acttcttcac ccaggagccg ctgcacctgg tgagcccctc    300
gttcctgtcc gtcaccattg acgccaacct ggccacggac ccgcggttcc tcatcctcct    360
gggttctcca aagcttcgta ccttggccag aggcttgtct cctgcgtacc tgaggtttgg    420
tggcaccaag acagacttcc taattttcga tcccaagaag gaatcaacct ttgaagagag    480
aagttactgg caatctcaag tcaaccagga tatttgcaaa tatggatcca tccctcctga    540
tgtggaggag aagttacggt tggaatggcc ctaccaggag caattgctac tccgagaaca    600
ctaccagaaa aagttcaaga acagcaccta ctcaagaagc tctgtagatg tgctatacac    660
ttttgcaaac tgctcaggac tggacttgat cttgggccta aatgcgttat taagaacagc    720
agatttgcag tggaacagtt ctaatgctca gttgctcctg gactactgct cttccaaggg    780
gtataacatt tcttgggaac taggcaatga acctaacagt ttccttaaga aggctgatat    840
tttcatcaat gggtcgcagt taggagaaga ttttattcaa ttgcataaac ttctaagaaa    900
gtccaccttc aaaaatgcaa aactctatgg tcctgatgtt ggtcagcctc gaagaaagac    960
ggctaagatc tgaagagct tcctgaaggc tggtggagaa gtgattgatt cagttacatg    1020
gcatcactac tatttgaatg gacggactgc taccagggaa gattttctaa accctgatgt    1080
attggacatt tttatttcat ctgtgcaaaa gttttccag gtggttgaga gcaccaggcc    1140
tggcaagaag gtctggttag gagaaacaag ctctgcatat ggaggcggag cgcccttgct    1200
atccgacacc tttgcagctg gctttatgtg gctggataaa ttgggcctgt cagcccgaat    1260
gggaatagaa gtggtgatga ggcaagtatt ctttggagca ggaaactacc atttagtgga    1320
tgaaaacttc gatccttac ctgattattg gctatctctt ctgttcaaga aattggtggg    1380
caccaaggtg ttaatggcaa gcgtgcaagg ttcaaagaga aggaagcttc gagtatacct    1440
tcattgcaca aacactgaca atccaaggta taagaaggga gatttaactc tgtatgccat    1500
```

```
aaacctccat aatgtcacca agtacttgcg gttaccctat cctttttcta acaagcaagt    1560
ggataaatac cttctaagac ctttgggacc tcatggatta ctttccaaat ctgtccaact    1620
caatggtcta actctaaaga tggtggatga tcaaaccttg ccacctttaa tggaaaaacc    1680
tctccggcca ggaagttcac tgggcttgcc agctttctca tatagttttt ttgtgataag    1740
aaatgccaaa gttgctgctt gcatctgaaa ataaaatata ctagtcctga cactgaattt    1800
ttcaagtata ctaagagtaa agcaactcaa gttataggaa aggaagcaga taccttgcaa    1860
agcaactagt gggtgcttga gagacactgg gacactgtca gtgctagatt tagcacagta    1920
tttgatctc gctaggtaga acactgctaa taataatagc taataatacc ttgttccaaa     1980
tactgcttag cattttgcat gttttacttt tatctaaagt tttgttttgt tttattattt    2040
atttatttat ttattttgtg acggagagag attccatctc aaaaaaacaa gttattaaaa    2100
atgtatatga atgctcctaa tatggtcagg aagcaaggaa gcgaaggata tattatgagt    2160
tttaagaagg tgcttagctg tatatttatc tttcaaaatg tattagaaga ttttagaatt    2220
ctttccttca tgtgccatct ctacaggcac ccatcagaaa aagcatactg ccgttaccgt    2280
gaaactggtt gtaaaagaga aactatctat ttgcaccta aaagacagct agattttgct      2340
gattttcttc tttcggtttt ctttgtcagc aataatatgt gagaggacag attgttagat    2400
atgatagtat aaaaaatggt taatgacaat tcagaggcga ggagattctg taaacttaaa    2460
attactataa atgaaattga tttgtcaaga ggataaattt tagaaaacac ccaataacct    2520
ataactgtct gttaatgctt gcttttctc taccttct ccttgtttca gttgggaagc         2580
ttttggctgc aagtaacaga aactcctaat tcaaatggct taagcaataa ggaaatgtat    2640
attcccacat aactagacgt tcaaacaggc caggctccag cacttcagta cgtcaccagg    2700
ggatctgggt tcttcccagc tctctgctct gccatcttta gcgctggctt cattctcaga    2760
ctctggtagc atgatggctg tagctgtttc atgggcccct tcaaacctca tagcaaccag    2820
aggaagaaaa tgagccattt tttgagtctc cttcatagac ttgaataact cttttcaga      2880
gcttctcaca gcaaacctct cctcatgtct cctcatgtct tattgttcag aaatgggtaa    2940
tgtggccatt tcaccagtca ctgccaacaa caacgaggtt cctataattg tctctgagta    3000
acccttgga atggagaggg tgttggtcag tctacaaact gaacactgca gttctgcgct      3060
ttttaccagt gaaaaatgt aattattttc ccctcttaag gattaatatt cttcaaatgt      3120
atgcctgtta tggatatagt atctttaaaa ttttttattt taatagcttt aggggtacac    3180
acttttgct tacaggggtg aattgtgtag tggtgaagac tcggctttta atgtacttgt      3240
cacctgagtg atgtacattg tacccaatag gtaattttc atccattacc ctccttccgc      3300
cctcttccct tctgagtctc caacatccct tataccactg tgtatgttct tgtgtaccta    3360
cagctaagct tccacttata agtgagaaca tgcagtattt ggttttccat tcctgagtta    3420
cttcccttag gataacagcc cccagttccg tccaagttgc tgcaaaatac attattcttc    3480
tttatggctg agtaatagtc catggtacat atataccaca ttttctttat ccacttatca    3540
gttgatggac acttaggtta attccattca atttcattca atttaagtat atttgtaagg    3600
agctaaagct gaaattaaa ttttagatct ttcaatactc ttaaatttta tatgtaagtg      3660
gttttatat tttcacattt gaaataaagt aattttata accttgaaaa aaaaaaaaa        3720
aaaaaa                                                                3726
```

<210> SEQ ID NO 10
<211> LENGTH: 4912

<212> TYPE: DNA
<213> ORGANISM: Homo sapiens

<400> SEQUENCE: 10

```
attggggtct gctctaagct gcagcaagag aaactgtgtg tgaggggaag aggcctgttt      60
cgctgtcggg tctctagttc ttgcacgctc tttaagagtc tgcactggag gaactcctgc     120
cattaccagc tcccttcttg cagaagggag ggggaaacat acatttattc atgccagtct     180
gttgcatgca ggcttttttgg cttcctacct tgcaacaaaa taattgcacc aactccttag    240
tgccgattcc gcccacagag agtcctggag ccacagtctt ttttgctttg cattgtagga     300
gagggactaa gtgctagaga ctatgtcgct ttcctgagct accgagagcg ctcgtgaact     360
ggaatcaact gcttcaggga aaagaaaaa aaaaaaaaa agacttgcct gggaggccgc       420
gagaaacttg cattggaagc ttcagcaacc agcattcgag aaactcctct ctactttagc     480
acggtctcca gactcagccg agagacagca aactgcagcg cggtgagaga gcgagagaga     540
gggagagaga gactctccag cctgggaact ataactcctc tgcgagaggc ggagaactcc     600
ttccccaaat cttttgggga cttttctctc tttacccacc tccgcccctg cgaggagttg     660
aggggccagt tcggccgccg cgcgcgtctt cccgttcggc gtgtgcttgg cccggggaac     720
cgggagggcc cggcgatcgc gcggcggccg ccgcgagggt gtgagcgcgc gtgggcgccc     780
gccgagccga ggccatggtg cagcaaacca acaatgccga gaacacggaa gcgctgctgg     840
ccggcgagag ctcggactcg ggcgccggcc tcgagctggg aatcgcctcc tcccccacgc     900
ccggctccac cgcctccacg ggcggcaagg ccgacgaccc gagctggtgc aagacccga     960
gtgggcacat caagcgaccc atgaacgcct tcatggtgtg gtcgcagatc gagcggcgca    1020
agatcatgga gcagtcgccc gacatgcaca acgccgagat ctccaagcgg ctgggcaaac    1080
gctggaagct gctcaaagac agcgacaaga tcccctttcat tcgagaggcg gagcggctgc    1140
gcctcaagca catggctgac taccccgact acaagtaccg gcccaggaag aaggtgaagt    1200
ccggcaacgc caactccagc tcctcggccg ccgcctcctc aagccggggg gagaagggag    1260
acaaggtcgg tggcagtggc gggggcggcc atggggcgg cggcggcggc gggagcagca    1320
acgcgggggg aggaggcggc ggtgcgagtg gcggcggcgc caactccaaa ccggcgcaga    1380
aaaagagctg cggctccaaa gtggcgggcg gcgcgggcgg tggggttagc aaaccgcacg    1440
ccaagctcat cctggcaggc ggcggcggcg cgggaaagc agcggctgcc gccgccgcct    1500
ccttcgccgc cgaacaggcg ggggccgccg ccctgctgcc cctgggcgcc gccgccgacc    1560
accactcgct gtacaaggcg cggactccca gcgcctcggc ctccgcctcc tcggcagcct    1620
cggcctccgc agcgctcgcg gccccgggca agcacctggc ggagaagaag gtgaagcgcg    1680
tctacctgtt cggcggcctg ggcacgtcgt cgtcgcccgt gggcggcgtg ggcgcgggag    1740
ccgaccccag cgaccccctg ggcctgtacg aggaggaggg cgcgggctgc tcgcccgacg    1800
cgcccagcct gagcggccgc agcagcgccg cctcgtcccc cgccgccggc cgctcgcccg    1860
ccgaccaccg cggctacgcc agcctgcgcg ccgcctcgcc cgccccgtcc agcgcgccct    1920
cgcacgcgtc ctcctcggcc tcgtcccact cctcctcttc ctcctcctcg ggctcctcgt    1980
cctccgacga cgagttcgaa gacgacctgc tcgacctgaa cccagctca aactttgaga    2040
gcatgtccct gggcagcttc agttcgtcgt cggcgctcga ccgggacctg gattttaact    2100
tcgagcccgg ctccggctcg cacttcgagt tcccggacta ctgcacgccc gaggtgagcg    2160
agatgatctc gggagactgg ctcgagtcca gcatctccaa cctggttttc acctactgaa    2220
```

-continued

```
gggcgcgcag gcagggagaa gggccggggg gggtaggaga ggagaaaaaa aaagtgaaaa    2280
aaagaaacga aaaggacaga cgaagagttt aaagagaaaa gggaaaaaag aaagaaaaag    2340
taagcagggc tggcttcgcc cgcgttctcg tcgtcggatc aaggagcgcg cggcgttttt    2400
ggacccgcgc tcccatcccc caccttcccg ggccggggac ccactctgcc cagccggagg    2460
gacgcggagg aggaagaggg tagacagggg cgacctgtga ttgttgttat tgatgttgtt    2520
gttgatggca aaaaaaaaaa agcgacttcg agtttgctcc cctttgcttg aagagacccc    2580
ctccccctcc caacgagctt ccggacttgt ctgcacccc agcaagaagg cgagttagtt     2640
ttctagagac ttgaaggagt ctccccttc ctgcatcacc accttggttt tgttttattt     2700
tgcttcttgg tcaagaaagg aggggagaac ccagcgcacc cctcccccc ttttttttaaa    2760 cgcgtgatga agacagaagg ctccgggtg acgaatttgg ccgatggcag atgtttgggg     2820
ggaacgccgg gactgagaga ctccacgcag gcgaattccc gtttgggggct ttttttttcct  2880 ccctcttttc cccttgcccc ctctgcagcc ggaggaggag atgttgaggg gaggaggcca    2940
gccagtgtga ccggcgctag gaaatgaccc gagaaccccg ttggaagcgc agcagcggga    3000
gctaggggcg ggggcggagg aggacacgaa ctggaagggg gttcacggtc aaactgaaat    3060
ggatttgcac gttggggagc tggcggcggc ggctgctggg cctccgcctt cttttctacg    3120
tgaaatcagt gaggtgagac ttcccagacc ccggaggcgt ggaggagagg agactgtttg    3180
atgtggtaca ggggcagtca gtggagggcg agtggtttcg gaaaaaaaaa aagaaaaaaa    3240
gaaaaaaaaa gaaaaaaaaa agatttttt cttctcttaa tcggaatcgt gatggtgttg     3300
gattatttca atggtgggt taatatagca tgttatcctg tctatctttt aaagatttct     3360
gtataagact gttgagcagt ttttaaaata gtgtaggata atataaaaag cagatagatg    3420
gcgctatgtt tgattcctac aacgaaatta tcaccagctt ttttttcattc ttaactcttt   3480 aaaggattca aacgcaactc aaatctgtgc tggactttaa aaaaacaatt caggaccaaa    3540
ttttttctca gtgtgtgtgt ttattcctta taggtgtaaa tgagaagacg tgttttttc     3600 cttcaccgat gctccatcct cgtatttctt tttccttgta aatgtaatca gatgccattt    3660
tatatgtgga cgtatttata ctggccaaac atattttttc ttttgtccct tttttttcttt   3720 cctttcttttt tacttccttt attctttat tccttccttt tccttttttt ctttttttttt   3780 tctttttttt tttttttttt tggtagttgt tgttacccac gccattttac gtctccttca    3840
ctgaagggct agagttttaa ctttttaattt tttatattta aatgtagact tttgacactt    3900
ttaaaaaaca aaaaagaca agagagatga aaacgtttga ttatttctc agtgtatttt     3960 tgtaaaaaat atataaaggg ggtgttaatc ggtgtaaatc gctgtttgga tttcctgatt    4020
ttataacagg gcggctggtt aatatctcac acagtttaaa aaatcagccc ctaatttctc    4080
catgtttaca cttcaatctg caggcttctt aaagtgacag tatcccttaa cctgccacca    4140
gtgtccaccc tccggccccc gtcttgtaaa aaggggagga gaattagcca aacactgtaa    4200
gcttttaaga aaacaaagt tttaaacgaa atactgctct gtccagaggc tttaaaactg     4260
gtgcaattac agcaaaaagg gattctgtag cttaacttg taaaccacat cttttttgca     4320
ctttttttat aagcaaaaac gtgccgttta accactgga tctatctaaa tgccgatttg     4380
agttcgcgac actatgtact cgttttttca ttcttgtatt tgactattta atcctttcta    4440
cttgtcgcta aatataattg ttttagtctt atggcatgat gatagcatat gtgttcaggt    4500
ttatagctgt tgtgttaaa aattgaaaaa agtggaaaac atcttgtac atttaagtct      4560 gtattataat aagcaaaaag attgtgtgta tgtatgttta atataacatg acaggcacta    4620
```

-continued

| | |
|---|---|
| ggacgtctgc cttttttaagg cagttccgtt aagggttttt gttttttaaac ttttttttgc | 4680 |
| catccatcct gtgcaatatg ccgtgtagaa tatttgtctt aaaattcaag gccacaaaaa | 4740 |
| caatgtttgg gggaaaaaaa agaaaaaatc atgccagcta atcatgtcaa gttcactgcc | 4800 |
| tgtcagattg ttgatatata ccttctgtaa ataacttttt ttgagaagga aataaaatca | 4860 |
| gctggaactg aaccctaaaa aaaaaaaaaa aaaaaaaaaa aaaaaaaaaa aa | 4912 |

<210> SEQ ID NO 11
<211> LENGTH: 4045
<212> TYPE: DNA
<213> ORGANISM: Homo sapiens

<400> SEQUENCE: 11

| | |
|---|---|
| gcagccagag ctcagcaggg ccctggagag atggccacgg tcccagcacc ggggaggact | 60 |
| ggagagcgcg cgctgccacc gccccatgtc tcagccaggg cttccttcct cggctccacc | 120 |
| ctgtggatgt aatggcggcc cctgctctgt cctggcgtct gccctcctc atcctcctcc | 180 |
| tgcccctggc tacctcttgg gcatctgcag cggtgaatgg cacttcccag ttcacatgct | 240 |
| tctacaactc gagagccaac atctcctgtg tctggagcca agatgggct ctgcaggaca | 300 |
| cttcctgcca agtccatgcc tggccggaca dacggcggtg gaaccaaacc tgtgagctgc | 360 |
| tccccgtgag tcaagcatcc tgggcctgca acctgatcct cggagcccca gattctcaga | 420 |
| aactgaccac agttgacatc gtcaccctga gggtgctgtg ccgtgagggg gtgcgatgga | 480 |
| gggtgatggc catccaggac ttcaagccct tgagaaacct tcgcctgatg ccccccatct | 540 |
| ccctccaagt tgtccacgtg gagacccaca gatgcaacat aagctgggaa atctcccaag | 600 |
| cctcccacta ctttgaaaga cacctggagt tcgaggcccg gacgctgtcc ccaggccaca | 660 |
| cctgggagga ggccccctg ctgactctca agcagaagca ggaatggatc tgcctggaga | 720 |
| cgctcacccc agacacccag tatgagtttc aggtgcgggt caagcctctg caaggcgagt | 780 |
| tcacgacctg gagccctggg agccagcccc tggccttcag acaaagcct gcagcccttg | 840 |
| ggaaggacac cattccgtgg ctcggccacc tcctcgtggg cctcagcggg gcttttggct | 900 |
| tcatcatctt agtgtacttg ctgatcaact gcaggaacac cgggccatgg ctgaagaagg | 960 |
| tcctgaagtg taacaccca gacccctcga agttctttc ccagctgagc tcagagcatg | 1020 |
| gaggagacgt ccagaagtgg ctctcttcgc ccttcccctc atcgtccttc agccctggcg | 1080 |
| gcctggcacc tgagatctcg ccactagaag tgctggagag ggacaaggtg acgcagctgc | 1140 |
| tcctgcagca ggacaaggtg cctgagcccg catccttaag cagcaaccac tcgctgacca | 1200 |
| gctgcttcac caaccagggt tacttcttct tccacctccc ggatgccttg gagatagagg | 1260 |
| cctgccaggt gtactttact tacgacccct actcagagga agaccctgat gagggtgtgg | 1320 |
| ccggggcacc cacagggtct tcccccaac ccctgcagcc tctgtcaggg gaggacgacg | 1380 |
| cctactgcac cttcccctcc agggatgacc tgctgctctt ctcccccagt ctcctcggtg | 1440 |
| gccccagccc ccaagcact gcccctgggg gcagtggggc cggtgaagag aggatgcccc | 1500 |
| cttctttgca agaaagagtc cccagagact gggaccccca gcccctgggg cctcccaccc | 1560 |
| caggagtccc agacctggtg gattttcagc caccccctga gctggtgctg cgagaggctg | 1620 |
| gggaggaggt ccctgacgct ggccccaggg agggagtcag tttccccctgg tccaggcctc | 1680 |
| ctgggcaggg ggagttcagg gcccttaatg ctcgcctgcc cctgaacact gatgcctact | 1740 |
| tgtccctcca agaactccag ggtcaggacc caactcactt ggtgtagaca gatggccagg | 1800 |

-continued

```
gtgggaggca ggcagctgcc tgctctgcgc cgagcctcag aaggaccctg ttgagggtcc    1860
tcagtccact gctgaggaca ctcagtgtcc agttgcagct ggacttctcc acccggatgg    1920
cccccaccca gtcctgcaca cttggtccat ccatttccaa acctccactg ctgctcccgg    1980
gtcctgctgc ccgagccagg aactgtgtgt gttgcagggg ggcagtaact ccccaactcc    2040
ctcgttaatc acaggatccc acgaatttag gctcagaagc atcgctcctc tccagccctg    2100
cagctattca ccaatatcag tcctcgcggc tctccagggc tccctgccct gacctcttcc    2160
ctgggttttc tgccccagcc tcctccttcc ctccctccc cgtccacagg gcagcctgag    2220
cgtgctttcc aaaacccaaa tatggccacg ctcccctcg gttcaaaacc ttgcacaggt    2280
cccactgccc tcagccccac ttctcagcct ggtacttgta cctccggtgt cgtgtgggga    2340 catcccttc tgcaatcctc cctaccgtcc tcctgagcca ctcagagctc cctcacaccc    2400
cctctgttgc acatgctatt ccctggggct gctgtgcgct cccctcatc taggtgacaa    2460 acttccctga ctcttcaagt gccggttttg cttctcctgg agggaagcac tgcctccctt    2520
aatctgccag aaacttctag cgtcagtgct ggagggagaa gctgtcaggg acccaggggcg    2580 cctggagaaa gaggccctgt tactattcct ttgggatctc tgaggcctca gagtgcttgg    2640
ctgctgtatc tttaatgctg gggcccaagt aagggcacag atccccccac aaagtggatg    2700
cctgctgcat cttcccacag tggcttcaca gacccacaag agaagctgat ggggagtaaa    2760
ccctggagtc cgaggcccag gcagcagccc cgcctagtgg tgggccctga tgctgccagg    2820
cctgggacct cccactgccc cctccactgg aggggtctcc tctgcagctc agggactggc    2880
acactggcct ccagaagggc agctccacag ggcagggcct cattattttt cactgcccca    2940
gacacagtgc ccaacacccc gtcgtatacc ctggatgaac gaattaatta cctggcacca    3000
cctcgtctgg gctccctgcg cctgacattc acacagagag gcagagtccc gtgcccatta    3060
ggtctggcat gcccctcct gcaaggggct caacccccta ccccgacccc tccacgtatc    3120
tttcctagga agatcacgtt gcaatggctc aaacaacatt ccacccccagc aggacagtga    3180 ccccagtccc agctaactct gacctgggag ccctcaggca cctgcactta caggccttgc    3240
tcacagctga ttgggcacct gaccacacgc ccccacaggc tctgaccagc agcctatgag    3300
ggggtttggc accaagctct gtccaatcag gtaggctggg cctgaactag ccaatcagat    3360
caactctgtc ttgggcgttt gaactcaggg agggaggccc ttgggagcag gtgcttgtgg    3420
acaaggctcc acaagcgttg agccttggaa aggtagacaa gcgttgagcc actaagcaga    3480
ggaccttggg ttcccaatac aaaaatacct actgctgaga gggctgctga ccatttggtc    3540
aggattcctg ttgcctttat atccaaaata aactcccctt tcttgaggtt gtctgagtct    3600
tgggtctatg ccttgaaaaa agctgaatta ttggacagtc tcacctcctg ccatagggtc    3660
ctgaatgttt cagaccacaa ggggctccac acctttgctg tgtgttctgg ggcaacctac    3720
taatcctctc tgcaagtcgg tctccttatc cccccaaatg gaaattgtat ttgccttctc    3780
cactttggga ggctcccact tcttgggagg gttacatttt ttaagtctta atcatttgtg    3840
acatatgtat ctatacatcc gtatcttta atgatccgtg tgtaccatct ttgtgattat    3900
ttccttaata ttttttcttt aagtcagttc attttcgttg aaatacattt atttaaagaa    3960
aaatctttgt tactctgtaa atgaaaaaac ccattttcgc tataaataaa aggtaactgt    4020
acaaaataag tacaatgcaa caaaa                                          4045
```

<210> SEQ ID NO 12
<211> LENGTH: 3033

<212> TYPE: DNA
<213> ORGANISM: Homo sapiens

<400> SEQUENCE: 12

| | | | | | |
|---|---|---|---|---|---|
| gcgggggcgc | gtcggggctg | gagccggagc | gcgccgggcg | ctgggcgcag | cgagcgagag | 60 |
| cgcggcggcc | gcgggctccg | gcgagggaca | gacgcaccga | tcgccggagg | gacagacaca | 120 |
| cgaccacgcg | gcgccaccgc | ccacgcctcc | acccaccggc | gcccaagtcc | tccccgcgcc | 180 |
| gcctcctctg | tatggcacaa | actttcctcc | cgggacggaa | cacgctgcct | cagggagccc | 240 |
| gcgaccgcgc | cttctcctcc | gccggtccca | tacgctgctg | aaatgggttg | cggattgaac | 300 |
| aagttagaga | acgtgatga | aaaacggcct | gggaatattt | attcaacttt | gaagaggcct | 360 |
| caggtggaaa | ccaagataga | tgtgtcctat | gaataccgct | tcctggagtt | cacgactctg | 420 |
| agtgctgcgg | agctccctgg | gtcctcagca | gtgaggctgg | cctccctgcg | tgacctgccc | 480 |
| gcccagctcc | tggagctgta | ccagcagggc | ttctcgctgg | cggccctgca | ccccttcgtg | 540 |
| cagcccaccc | atgagcggga | gaagacgccc | ctggagcaca | tctttagagc | catcctgatc | 600 |
| aagaaaaccg | acagatctca | gaaaactgat | cttcacaatg | aaggctacat | cttggaatta | 660 |
| gattgctgtt | cctccttaga | ccacccgaca | gaccagaaac | tcatcccaga | gttcattaag | 720 |
| aagatccagg | aggctgcaag | ccagggcctg | aaattcgttg | gtgttatacc | tcagtaccat | 780 |
| tcctctgtga | actcggcagg | cagcagtgct | ccggtgtcta | ctgccaacag | caccgaggat | 840 |
| gccagagatg | caaaaaacgc | acgtggggat | cacgcgtcac | tggagaatga | gaaaccgggg | 900 |
| actggggatg | tgtgcagtgc | tccggctggg | agaaaccaaa | gcccagagcc | cagctcaggc | 960 |
| cccagagggg | aggtgcccct | cgccaagcag | cccagctcac | cctccggaga | gggagatggt | 1020 |
| ggagaacttt | caccacaggg | ggtgagcaag | acactggatg | gaccgagag | caaccccttg | 1080 |
| gaggtgcatg | aagagccact | ctcagggaaa | atggagatct | tcacccttt | caacaaaccg | 1140 |
| aagagccatc | agaagtgccg | gcaatactac | cctgtcacca | ttcctctcca | tgtctccaag | 1200 |
| aatggccaga | cagtgagcgg | tttggacgcc | aactggttag | agcacatgag | cgaccacttc | 1260 |
| cggaaaggag | gcatgctggt | gaacgcagtc | ttctaccttg | gaatagtgaa | tgattccttta | 1320 |
| catggcttga | cagatggagt | attcatcttt | gaagctgttt | ccacagaaga | tagcaaaaacc | 1380 |
| atacagggct | atgatgctat | tgtggttgaa | caatggacag | tcctggaagg | tgtcgaagtg | 1440 |
| cagacagact | acgtgcccct | gctgaactcg | ctggcggcct | atggctggca | gctcacctgt | 1500 |
| gtgctaccaa | ctcccgtcgt | caagactacc | agcgagggga | gtgtatccac | caagcagatt | 1560 |
| gtctttcttc | agagaccttg | tctacctcag | aaaatcaaga | agaaggaatc | gaagtttcag | 1620 |
| tggcgattct | ccagagaaga | aatgcacaac | aggcagatga | ggaaatcaaa | aggtaaactc | 1680 |
| agtgccagag | acaaacaaca | agcagaagaa | aatgagaaga | acttagaaga | ccagtcttcc | 1740 |
| aaagctggag | acatgggaaa | ctgtgtttca | ggacagcagc | aggagggtgg | agtctccgag | 1800 |
| gagatgaagg | gccctgtcca | agaggacaag | ggagaacagc | tgtcccctgg | tggcctgctg | 1860 |
| tgtgggggtgg | gtgtggaggg | tgaggctgtg | cagaatggtc | ctgccagcca | cagcagggcc | 1920 |
| ctggtgggga | tttgcactgg | gcactccaat | cctggagagg | atgccaggga | cggggatgct | 1980 |
| gaggaagtca | gagagcttgg | tacgttgaa | gaaaactgag | tcttgggcaa | tttgtgctaa | 2040 |
| aactaggtga | gttgccaaac | ccaaggcatc | ttaccaacag | ctggtttggg | ggctggtttc | 2100 |
| cctggtgttg | tgtgttacct | acccttggc | ttggcttgac | ctctccttgt | gagctcacct | 2160 |
| gagccctccc | agggccaggt | tcctgacagt | gttggttttt | gcacatccac | tggaaaggtg | 2220 |

| | |
|---|---|
| tcattaatga cccagtgtta aaatgcaaga ggtcaggtta ttctagccct catggctgaa | 2280 |
| ggcccagtcc tggctccacc actcctccag ccagagggtc tggaccatcc agtgcctgtc | 2340 |
| ctcgccacag ggcctccagg gagcattcgg gtcaaatcca tggacaccct gggctacaaa | 2400 |
| ccaaggctgc tgttcatccc acatcgtgtg gggcagtgtc catcccctgc agctacttgg | 2460 |
| tgacttaaca actccaggag ccctgtcagc tgccctcctc cacctaaacc ccttcgactc | 2520 |
| ttctgctttg acaagaaaaa tgacattggg gaggggaggt gctccgcctc ccagcttttc | 2580 |
| tcaaaatagt cctatagata ctggtaatct ggaaatgaag aagtaattct gtctctgcac | 2640 |
| ctacttttgc agaatgttca aggaagtatt ctgtgttagt attaatgcca aaaagttgtt | 2700 |
| tttaaaggtt ttgtactcag cacatcatac aaaccacatt acttctgtca cttcagggca | 2760 |
| tcgggactgg ctggcgccct tgttatgtgc tattttaatc agtgtaacat tggtcaagtt | 2820 |
| gttacccatg tatgctgtgt ttatcatgtg tatatcgtcc agaaagtatt aaggctttag | 2880 |
| gtagatgcaa ctggcgaacc ttggagaggg aatgctgatt gtcttgacca aacccacagc | 2940 |
| ctgtctcttc tcttgtttag ttacttacgg caataaatca tctatgagtt agtgcaccgt | 3000 |
| gaaaaaaaaa aaaaaaaaaa aaaaaaaaaa aaa | 3033 |

<210> SEQ ID NO 13
<211> LENGTH: 3146
<212> TYPE: DNA
<213> ORGANISM: Homo sapiens

<400> SEQUENCE: 13

| | |
|---|---|
| gccgcaaccc gtcccggagg tgtcctgtct cctgtcgccg ccgccgccgc caccaccgct | 60 |
| gccactgccg ccctgccggg gccatgttcg ctctgggctt gcccttcttg gtgctcttgg | 120 |
| tggcctcggt cgagagccat ctgggggttc tggggcccaa gaacgtctcg cagaaagacg | 180 |
| ccgagtttga gcgcacctac gtggacgagg tcaacagcga gctggtcaac atctacacct | 240 |
| tcaaccatac tgtgacccgc aacaggacag agggcgtgcg tgtgtctgtg aacgtcctga | 300 |
| acaagcagaa gggggcgccg ttgctgtttg tggtccgcca gaaggaggct gtggtgtcct | 360 |
| tccaggtgcc cctaatcctg cgagggatgt ttcagcgcaa gtacctctac caaaaagtgg | 420 |
| aacgaaccct gtgtcagccc cccaccaaga tgagtcggga gattcagttc ttctacgtgg | 480 |
| atgtgtccac cctgtcacca gtcaacacca cataccagct ccgggtcagc cgcatggacg | 540 |
| attttgtgct caggactggg gagcagttca gcttcaatac cacagcagca cagccccagt | 600 |
| acttcaagta tgagttccct gaaggcgtgg actcggtaat tgtcaaggtg acctccaaca | 660 |
| aggccttccc ctgctcagtc atctccattc aggatgtgct gtgtcctgtc tatgacctgg | 720 |
| acaacaacgt agccttcatc ggcatgtacc agacgatgac caagaaggcg ccatcaccg | 780 |
| tacagcgcaa agacttcccc agcaacagct tttatgtggt ggtggtggtg aagaccgaag | 840 |
| accaagcctg cggggggctcc ctgcctttct acccccttcgc agaagatgaa ccggtcgatc | 900 |
| aagggcaccg ccagaaaacc ctgtcagtgc tggtgtctca agcagtcacg tctgaggcat | 960 |
| acgtcagtgg gatgctcttt tgcctgggta tatttctctc cttttacctg ctgaccgtcc | 1020 |
| tcctggcctg ctgggagaac tggaggcaga agaagaagac cctgctggtg gccattgacc | 1080 |
| gagcctgccc agaaagcggt caccctcgag tcctggctga ttcttttcct ggcagttccc | 1140 |
| cttatgaggg ttacaactat ggctcctttg agaatgtttc tggatctacc gatggtctgg | 1200 |
| ttgacagcgc tggcactggg gacctctctt acgttacca ggggcacgac cagttcaagc | 1260 |
| ggcgcctccc ctctggccag atgcggcagc tgtgcattgc catgggccgc tcctttgaac | 1320 |

-continued

```
ctgtaggtac tcggccccga gtggactcca tgagctctgt ggaggaggat gactacgaca    1380
cattgaccga catcgattcc gacaagaatg tcattcgcac caagcaatac ctctatgtgg    1440
ctgacctggc acggaaggac aagcgtgttc tgcggaaaaa gtaccagatc tacttctgga    1500
acattgccac cattgctgtc ttctatgccc ttcctgtggt gcagctggtg atcacctacc    1560
agacggtggt gaatgtcaca gggaatcagg acatctgcta ctacaacttc ctctgcgccc    1620
acccactggg caatctcagc gccttcaaca acatcctcag caacctgggg tacatcctgc    1680
tggggctgct tttcctgctc atcatcctgc aacgggagat caaccacaac cgggccctgc    1740
tgcgcaatga cctctgtgcc ctggaatgtg ggatccccaa acactttggg cttttctacg    1800
ccatgggcac agccctgatg atggaggggc tgctcagtgc ttgctatcat gtgtgcccca    1860
actataccaa tttccagttt gacacatcgt tcatgtacat gatcgccgga ctctgcatgc    1920
tgaagctcta ccagaagcgg cacccggaca tcaacgccag cgcctacagt gcctacgcct    1980
gcctggccat tgtcatcttc ttctctgtgc tgggcgtggt cttttggcaaa gggaacacgg    2040 cgttctggat cgtcttctcc atcattcaca tcatcgccac cctgctcctc agcacgcagc    2100
tctattacat gggccggtgg aaactggact cggggatctt ccgccgcatc ctccacgtgc    2160
tctacacaga ctgcatccgg cagtgcagcg ggccgctcta cgtggaccgc atggtgctgc    2220
tggtcatggg caacgtcatc aactggtcgc tggctgccta tgggcttatc atgcgcccca    2280
atgatttcgc ttcctacttg ttggccattg gcatctgcaa cctgctcctt tacttcgcct    2340
tctacatcat catgaagctc cggagtgggg agaggatcaa gctcatcccc ctgctctgca    2400
tcgtttgcac ctccgtggtc tggggcttcg cgctcttctt cttcttccag ggactcagca    2460
cctggcagaa acccctgca gagtcgaggg agcacaaccg ggactgcatc ctcctcgact    2520
tctttgacga ccacgacatc tggcacttcc tctcctccat cgccatgttc gggtccttcc    2580
tggtaagcgg gcctcccggc gcagcgttga ggataacgtg aaaggtagca gctgcctcct    2640
tctctgtgag ctgatctggc gtccacaccc caggtgttag ctgacactgg atgacgacct    2700
ggatacttag aaaggggctt caggaaggga tgtgctgttt ccctctacgt gcccagtcct    2760
agcctcgctc taggacccag ggctggcttc taagtttccg tccagtcttc aggcaagttc    2820
tgtgttagtc atgcacacac atacctatga aaccttgaag tttacaaaga attgccccag    2880
ctctgggcac cctggccacc ctggtccttg gatcccttc gtcccacctg gtccacccca    2940
gatgctgagg atgggggagc tcaggcgggg cctctgcttt ggggatggga atgtgttttt    3000
ctcccaaact tgttttttata gctctgcttg aagggctggg agatgaggtg ggtctggatc    3060
ttttctcaga gcgtctccat gctatggttg catttccgtt ttctatgaat gaatttgcat    3120
acaataacca accagactca gtaaaa                                         3146
```

<210> SEQ ID NO 14
<211> LENGTH: 1558
<212> TYPE: DNA
<213> ORGANISM: Homo sapiens

<400> SEQUENCE: 14

```
cggaggagag cgcaggagga aacagtaccg gctggaggcc ggtcttgcag gagcggggga     60
ctgctggggg cggggcttgg tggtgaccgc tggcggggcg gggcctgggg ctcagagggg    120
tgggctttgg agatcagagg gtcgacgctg cttcgttgcc tggactctgg tttccgccct    180
ggagcaagcc ggggcctggt cggcagctgg gccgccatgg agtccacgct gggcgcgggc    240
```

```
atcgtgatag ccgaggcgct acagaaccag ctagcctggc tggagaacgt gtggctctgg    300
atcacctttc tgggcgatcc caagatcctc tttctgttct acttccccgc ggcctactac    360
gcctcccgcc gtgtgggcat cgcggtgctc tggatcagcc tcatcaccga gtggctcaac    420
ctcatcttca gtggtttct ttttggagac aggccctttt ggtgggtcca tgagtctggt    480
tactacagcc aggctccagc ccaggttcac cagttcccct cttcttgtga gactggtcca    540
ggcagccctt ctggacactg catgatcaca ggagcagccc tctggcccat aatgacggcc    600
ctgtcttcgc aggtggccac tcgggcccgc agccgctggg taagggtgat gcctagcctg    660
gcttattgca ccttcctttt ggcggttggc ttgtcgcgaa tcttcatctt agcacatttc    720
cctcaccagg tgctggctgg cctaataact ggcgctgtcc tgggctggct gatgactccc    780
cgagtgccta tggagcggga gctaagcttc tatgggttga ctgcactggc cctcatgcta    840
ggcaccagcc tcatctattg gaccctcttt acactgggcc tggatctttc ttggtccatc    900
agcctagcct tcaagtggtg tgagcggcct gagtggatac acgtggatag ccggcccttt    960
gcctccctga gccgtgactc aggggctgcc ctgggcctgg gcattgcctt gcactctccc    1020
tgctatgccc aggtgcgtcg ggcacagctg ggaaatggcc agaagatagc ctgccttgtg    1080
ctggccatgg ggctgctggg ccccctggac tggctgggcc accccctca gatcagcctc    1140 ttctacattt tcaatttcct caagtacacc ctctggccat gctagtcct ggccctcgtg    1200 ccctgggcag tgcacatgtt cagtgcccag gaagcaccgc ccatccactc ttcctgactt    1260
cttgtgtgcc tccctttcct ttccctccca aaagccaac actctgtgac caccacactc    1320
caggaggcag cccatcccc ttccagcccc taagtaggcc ctcccctccc taaatctgct    1380
tccgcaccac ctggtcttag ccccaaagat gggccttctc tctcccagat aagttggtcc    1440
tccctctgcc tttcctctca gccccaaa gagcaaggc aacagcaaga ccagcgggtt    1500
cttgcaacac tgtgaggggc agccagggcg gccccaataa agcccttgaa tactttga    1558
```

<210> SEQ ID NO 15
<211> LENGTH: 5388
<212> TYPE: DNA
<213> ORGANISM: Homo sapiens

<400> SEQUENCE: 15

```
gcaacagcgg cggcggccgc ggcggctggc cggactcagg tgtttcggac gctattgccc     60
ttcgcgccag ccgtcgagtg ggcagcagcg ggactcagcc gggcgccagg ttcctgccag    120
gcagcgccgg gaagcgcggg cggccgagaa ctccttcctg ctacttcgcc cagcgccgct    180
gcttcggctt cccagcgaag tgggagacct tcctccctgt ttgcagacgt ccgtgggaga    240
cccttatttt ttccaccgct aaggttaaga gattctggaa tagaagcgtc gaaggagatc    300
aagtgaacct tctacaactc ctcggatgtc gccagtctcc ctttcggggc ggaagactac    360
gtttgagcat ctcactgagg tgcaggaatg gaagaaccca ccttgcagct tttctgcagt    420
gtggcttgcc tgatctaccc ctaggaatga agaggaggct tgtaataatc cgatgaagta    480
cagatgttga agaggatatc gcaggaccta aacttgtgat cgtttggggg aggtcacaca    540
cgtttctgag tgggaatgga tgggcgtgaa tgacgtgccc tcttaaaaag cacaacagtc    600
ctttaagagg agcaaaattg agttttccca ttttggccaa gattttgaag acagttcaat    660
gtattctaca tttgacataa gatgagaact ttctaaagta ttctctccaa gagcgtaaac    720
gatgactacc ccagccctgc tgcccctctc tggacgtagg ataccactc tgaacctggg    780 gccgccttcc ttcccacatc acagggctac cttgagactt tctgagaagt ttattcttct    840
```

```
ccttattctt agtgccttca tcactctgtg ttttggggca ttcttttttcc ttccagactc      900 ttcaaaacac aaacgctttg atttgggttt agaagatgtg ttaattccac atgtagatgc      960
cggtaaaggg gctaaaaacc ccggagtctt cctgatccat ggacccgatg aacatagaca     1020
cagggaagag aagaacgtc tgagaaataa aattcgagct gatcatgaga aggccttgga     1080
agaagcaaaa gaaaaattaa gaaagtcaag agaggaaatt cgagcagaaa ttcagacaga     1140
gaaaaataag gtagtccaag aaatgaagat aaaagagaac aagccactgc caccagtccc     1200
tattcccaac cttgtaggaa tacgtggtgg agacccagaa gataatgaca taagagagaa     1260
aagggaaaaa attaaagaga tgatgaaaca tgcttgggat aactatagga catatgggtg     1320
gggacataat gaactcagac ctattgcaag gaaaggacac tcccctaaca tatttggaag     1380
ttcacaaatg ggtgctacca tagtagatgc tttggatacc ctttatatca tgggacttca     1440
tgatgaattc ctagatgggc aaagatggat tgaagacaac cttgatttca gtgtgaattc     1500
agaggtgtct gtgtttgaag tcaacattcg atttattgga ggcctacttg cagcatatta     1560
cctatcagga gaggagatat tcaagattaa agcagtgcaa ttggctgaga aactccttcc     1620
tgcctttaac acacctactg ggattccttg ggcaatggtg aatttgaaaa gtggagtagg     1680
gcgaaactgg ggctgggcat ctgcaggtag cagcattctg gctgaatttg gtacactaca     1740
tatggagttc atccacctca gctacttgac aggggacctg acttactaca aaaaggttat     1800
gcacattcgg aaactacttc agaaaatgga tcgtccaaat ggtctttatc caaattattt     1860 gaacccccaga acagggcgct ggggtcagta tcatacatct gtcggtggcc tgggagacag     1920 ttttatgaa tacttactga agcatggtt gatgtcagat aaaacagacc atgaggcaag     1980
aaagatgtat gatgatgcta ttgaggctat agaaaaacat cttattaaga agtctcgtgg     2040
aggtcttacc tttattggag aatggaagaa tgggcacttg gaaaaaaaga tggggcattt     2100
ggcctgcttt gctgggggaa tgtttgcact aggagcagat ggttccgagg cagataaagc     2160
tggtcattat ttagagctag gggcagaaat tgcacgtact tgtcatgagt catatgacag     2220
aactgcatta aagctaggtc ctgaatcatt caagtttgat ggtgcagtgg aggctgtggc     2280
tgtccggcag gctgaaaagt attatatcct ccgtccagaa gtaattgaaa cctattggta     2340
cctatggcga ttcactcacg atccaagata caggcagtgg ggctgggaag cagcactggc     2400
cattgaaaag tattgccgag ttaatggtgg gttttctgga gtcaaagatg tatattcctc     2460
tactcctaca catgatgatg tacagcagag ctttttttctt gctgaaacat taaaatattt     2520
gtatctgctg ttctccggtg atgacctttt acctttagac cactgggtgt ttaatacaga     2580
ggctcaccct ctgcctgtgt tacatttagc caacaccaca ctttcaggta atcctgctgt     2640
tcgatgaaag cagttccaga aggaccattc tcacctgtgt tttgtttaca tggaccacta     2700
cagaaattag tttgaagggg cggcttttga aaacctggac ctctatgtca acatgacagg     2760
gtgaaactat tcccctaag actgttcaac ttgtagatac atcaactttg aaattattcc     2820
attttatacc tgaccaaaac atgttctgat atgtgtagga cagagacctg gatgtgcttt     2880
gatcgttaat gaggtggtca catgagaaat gataccgtt actactgtat tgttttttaga     2940 gtcctgaagt ctggaggcta gacttcctga agcaagtca agaatataga gcaccttgca     3000
ggagttcaag atggcctttg gaaccaatta tgtatttgtt tcctcctaca gtggagcagc     3060
attcaaatca aatatttaca tattgcttat cacttttttct ccatttaat aatggaatga     3120 actaaaataa acaagaacaa aagaatagta taattatatc agtaacaaga agactcaaaa     3180
```

| | |
|---|---|
| aagaaacagg agtacctatc cctatctgaa ttttcaagtt ccccattgga tgaccagact | 3240 |
| ggcaaccatt tcaaatccca gtctatttca ttgaaatttc ttggttaagt ttaattttct | 3300 |
| ctgggggcat gatctcacaa agaatactca agtcttttc ttcttatgga atcatcgaaa | 3360 |
| ctgctattta tcataatcac cacttatgag cctgggtttg ggattttgtg catgtagttc | 3420 |
| agtctagtgt tggtagcatg acagaaagtg gggaaaatgc cgcagtttgt tgccttgaaa | 3480 |
| cctaagagca atccttggtt ttgttgctac attattttc cagaccaaca catctaccaa | 3540 |
| gtaaatttta ttcactttaa tttcataata aagttagtag agtcactcaa cttacaactt | 3600 |
| tatttatgtg gcttggcaaa aatcactata aggcagctct aaatttgcct tgataagcta | 3660 |
| aataaattac ttttataact tactaaagca gaacaaacag tgaaactttc taaaatattc | 3720 |
| tatctggaat agggacaggg gatcttttat ttataatctc atcagatgag tgagttgttc | 3780 |
| acagatattt tatgtttttt taattttctc caagaatatt tatagaattc caaagaatca | 3840 |
| gaatagtttc aaaataattt tcagtgataa aagagtgttg taattaatca tattacacta | 3900 |
| aaattgggat acatctaagg aacttatct tactatcagt aggttttgca ttgatatttc | 3960 |
| tttttaaata aactactagt tctttatatt ttgacaaaaa gaacttaaat tttatcagga | 4020 |
| actgtaagat aaatatctag tgcttataaa ttttctgtcc ttaaatttat gtgacagtgc | 4080 |
| aagatacttt tgctcttttc atttaatata ggcatcttcc attgacatta ataaaactta | 4140 |
| gaaacagtat aattagtata acatttactc tgaatttgaa gatttcctga aacaaagttt | 4200 |
| gtacaagaag cccaccttgg aattctgaag gcttattttc ttgtttgata agcttttctt | 4260 |
| ttaaacttag gttttaagtt ggggaaagac ttaattaact aatatagtat tttctaaggt | 4320 |
| tgatcatctt ataccacgaa tcgttaattt tgacagttct actgatccgt aaatgataac | 4380 |
| cactgcaaat ttttcagta taaaatttt cactgcaaaa aaatttcagt agaaaataag | 4440 |
| gatgcagggc cagttacaat agtccttaag agagttaaat tatagcacat gttttgacat | 4500 |
| tgtaatatct tttactactt gaacatttaa atttctaaat gagaaaggta tatatattac | 4560 |
| tgtaactgta gaagggaaaa gggaaagtat ttggttctaa aaaatgttag ccttcctcgt | 4620 |
| aaaagtagca caagcccact tatgaatcac tgagaaaaag tgaaaaactt gagttggcaa | 4680 |
| agatgcagag cagcagtgca gatggcaatg aactctctga attctctttt accttattta | 4740 |
| gaagaatgca gagtaaaggg accttcttgg ttctgcagga acttctcaag ggatgaggag | 4800 |
| acagaacccc tacttccaag tgctctattt gtattaccca gatgactgaa gcttaagaga | 4860 |
| aggcagggaa gtatacaagc agagccagtt ctggtacaaa caagaatttt gacagggaca | 4920 |
| atggaagggt cttcttcacc actccttacc ttctatgtga tggaaagact agagcttata | 4980 |
| aaagtacttc cattttttta ttctcctgaa taccaaaggc aattaaagtc agctacaaat | 5040 |
| gacttgccag tgtcatgttt tattttgtt atagattttt aaattattc cttcaagatc | 5100 |
| aattcttatc ccatataatg cttagcttcc aagaatattc tttactttct tctgtctttt | 5160 |
| acagctcttt gcattttgta gaccttaata ctcaggttaa atattcattg catttataag | 5220 |
| atcttctgca aaaagcccag aaatggtcct tttcaggtgc ctcttcaaag agctgacacc | 5280 |
| ttaccttgtg cctttggcac aaatgtgcag aatagataca tcagttggtg cataatcgaa | 5340 |
| aaaaatagga attttgaaca ctgttcttcc ttctacattt atttctct | 5388 |

<210> SEQ ID NO 16
<211> LENGTH: 2678
<212> TYPE: DNA
<213> ORGANISM: Homo sapiens

<400> SEQUENCE: 16

```
atgcgacccg accgcgctga ggctccagga ccgcccgcca tggctgcagg aggtcccggc      60
gcggggtctg cggccccggt ctcctccaca tcctcccttc ccctggctgc tctcaacatg     120
cgagtgcggc gccgcctgtc tctgttcttg aacgtgcgga cacaggtggc ggccgactgg     180
accgcgctgg cggaggagat ggactttgag tacttggaga tccggcaact ggagacacaa     240
gcggacccca ctggcaggct gctggacgcc tggcagggac ccctggcgc tctgtaggc      300
cgactgctcg agctgcttac caagctgggc gcgacgacg tgctgctgga gctgggaccc      360
agcattgagg aggattgcca aaagtatatc ttgaagcagc agcaggagga ggctgagaag     420
cctttacagg tggccgctgt agacagcagt gtcccacgga cagcagagct ggcgggcatc     480
accacacttg atgaccccct ggggcatatg cctgagcgtt tcgatgcctt catctgctat     540
tgccccagcg acatccagtt tgtgcaggag atgatccggc aactggaaca gacaaactat     600
cgactgaagt tgtgtgtgtc tgaccgcgat gtcctgcctg gcacctgtgt ctggtctatt     660
gctagtgagc tcatcgaaaa gaggtgccgc cggatggtgg tggttgtctc tgatgattac     720
ctgcagagca aggaatgtga cttccagacc aaatttgcac tcagcctctc tccaggtgcc     780
catcagaagc gactgatccc catcaagtac aaggcaatga gaaagagtt ccccagcatc      840
ctgaggttca tcactgtctg cgactacacc aaccccctgca ccaaatcttg gttctggact     900
cgccttgcca aggccttgtc cctgccctga agactgttct gaggccctgg gtgtgtgtgt     960
atctgtctgc ctgtccatgt acttctgccc tgcctcctcc tttcgttgta ggaggaatct    1020
gtgctctact tacctctcaa ttcctggaga tgccaacttc acagacacgt ctgcagcagc    1080
tggacatcac atttcatgtc ctgcatgaa ccagtggctg tgagtggcat gtccacttgc     1140
tggattatca gccaggacac tatagaacag gaccagctga gactaagaag gaccagcaga    1200
gccagctcag ctctgagcca ttcacacatc ttcaccctca gtttcctcac ttgaggagtg    1260
ggatggggag aacagagagt agctgtgttt gaatccctgt aggaaatggt gaagcatagc    1320
tctgggtctc ctgggggaga ccaggcttgg ctgcggagca gctggctgtt gctggactac    1380
atgctggcca ctgctgtgac cacgacactg ctggggcagc ttcttccaca gtgatgccta    1440
ctgatgcttc agtgcctctg cacaccgccc attccacttc ctccttcccc acagggcagg    1500
tggggaagca gtttggccca gcccaaggag accccatctt gagccttatt tcctaatggg    1560
tccacctctc atctgcatct ttcacacctc ccagcttctg cccaaccttc agcagtgaca    1620
agtccccaag agactcgcct gagcagcttg ggctgctttt catttccacc tgtcaggatg    1680
cctgtggtca tgctctcagc tccacctggc atgagaaggg atcctggcct ctggcatatt    1740
catcaagtat gagttctggg gatgagtcac tgtaatgatg tgagcaggga gccttcctcc    1800
ctgggccacc tgcagagagc tttcccacca actttgtacc ttgattgcct tacaaagtta    1860
tttgtttaca aacagcgacc atataaaagc ctcctgcccc aaagcttgtg ggcacatggg    1920
cacatacaga ctcacataca gacacacaca tatatgtaca gacatgtact ctcacacaca    1980
caggcaccag catacacacg ttttttctagg tacagctccc aggaacagct aggtgggaaa    2040
gtcccatcac tgagggagcc taaccatgtc cctgaacaaa aattgggcac tcatctattc    2100
cttttctctt gtgtccctac tcattgaaac caaactctgg aaaggaccca atgtaccagt    2160
atttatacct ctaatgaagc acagagagag gaagagagct gcttaaactc acacaacaat    2220
gaactgcaga cacagctgtt ctctccctct ctccttccca gagcaattta tactttaccc    2280
```

| | |
|---|---|
| tcaggctgtc ctctggggag aaggtgccat ggtcttaggt gtctgtgccc caggacagac | 2340 |
| cctaggaccc taaatccaat agaaaatgca tatctttgct ccactttcag ccaggctgga | 2400 |
| gcaaggtacc ttttcttagg atcttgggag ggaatggatg cccctctctg catgatcttg | 2460 |
| ttgaggcatt tagctgccat gcacctgtcc ccctttaata ctgggcattt taaagccatc | 2520 |
| tcaagaggca tcttctacat gttttgtacg cattaaaata atttcaaaga tatctgagaa | 2580 |
| aagccgatat ttgccattct tcctatatcc tggaatatat cttgcatcct gagtttataa | 2640 |
| taataaataa tattctacct tggaaaaaaa aaaaaaaa | 2678 |

<210> SEQ ID NO 17
<211> LENGTH: 950
<212> TYPE: DNA
<213> ORGANISM: Homo sapiens

<400> SEQUENCE: 17

| | |
|---|---|
| gggaccttaa ttctctttcc catcttgcaa gatggcgggt gaaaaagttg agaagccaga | 60 |
| tactaaagag aagaaacccg aagccaagaa ggttgatgct ggtggcaagg tgaaaaaggg | 120 |
| taacctcaaa gctaaaaagc ccaagaaggg gaagccccat tgcagccgca accctgtcct | 180 |
| tgtcagagga attggcaggt attcccgatc tgccatgtat tccagaaagg ccatgtacaa | 240 |
| gaggaagtac tcagccgcta aatccaaggt tgaaaagaaa aagaaggaga aggttctcgc | 300 |
| aactgttaca aaaccagttg gtggtgacaa gaacggcggt acccgggtgg ttaaacttcg | 360 |
| caaaatgcct agatattatc ctactgaaga tgtgcctcga aagctgttga gccacggcaa | 420 |
| aaaacccttc agtcagcacg tgagaaaact gcgagccagc attaccccg ggaccattct | 480 |
| gatcatcctc actggacgcc acaggggcaa gagggtggtt ttcctgaagc agctggctag | 540 |
| tggcttatta cttgtgactg gacctctggt cctcaatcga gttcctctac gaagaacaca | 600 |
| ccagaaattt gtcattgcca cttcaaccaa aatcgatatc agcaatgtaa aaatcccaaa | 660 |
| acatcttact gatgcttact tcaagaagaa gaagctgcgg aagcccagac accaggaagg | 720 |
| tgagatcttc gacacagaaa agagaaata tgagattacg gagcagcgca agattgatca | 780 |
| gaaagctgtg gactcacaaa ttttaccaaa aatcaaagct attcctcagc tccagggcta | 840 |
| cctgcgatct gtgtttgctc tgacgaatgg aatttatcct cacaaattgg tgttctaaat | 900 |
| gtcttaagaa cctaattaaa tagctgacta caaaaaaaaa aaaaaaaaaa | 950 |

<210> SEQ ID NO 18
<211> LENGTH: 700
<212> TYPE: DNA
<213> ORGANISM: Homo sapiens

<400> SEQUENCE: 18

| | |
|---|---|
| gcggcgtgag aagccatgag cagcaaagtc tctcgcgaca ccctgtacga ggcggtgcgg | 60 |
| gaagtcctgc acgggaacca gcgcaagcgc cgcaagttcc tggagacggt ggagttgcag | 120 |
| atcagcttga agaactatga tccccagaag gacaagcgct tctcgggcac cgtcaggctt | 180 |
| aagtccactc cccgccctaa gttctctgtg tgtgtcctgg gggaccagca gcactgtgac | 240 |
| gaggctaagg ccgtggatat cccccacatg gacatcgagg cgctgaaaaa actcaacaag | 300 |
| aataaaaaac tggtcaagaa gctggccaag aagtatgatg cgttttttggc ctcagagtct | 360 |
| ctgatcaagc agattccacg aatcctcggc ccaggtttaa ataaggcagg aaagttccct | 420 |
| tccctgctca cacacaacga aaacatggtg gccaaagtgg atgaggtgaa gtccacaatc | 480 |
| aagttccaaa tgaagaaggt gttatgtctg gctgtagctg ttggtcacgt gaagatgaca | 540 |

| | |
|---|---|
| gacgatgagc ttgtgtataa cattcacctg gctgtcaact tcttggtgtc attgctcaag | 600 |
| aaaaactggc agaatgtccg ggccttatat atcaagagca ccatgggcaa gccccagcgc | 660 |
| ctatattaag gcacatttga ataaattcta ttaccagttc | 700 |

<210> SEQ ID NO 19
<211> LENGTH: 1125
<212> TYPE: DNA
<213> ORGANISM: Homo sapiens

<400> SEQUENCE: 19

| | |
|---|---|
| cccccatgtg acagtgacgg ggtccccgct ccaggagacg ctcgagtctg cgtcccggcc | 60 |
| ctcagcactg tccactgttt cggtgccagc agagaccagc aggcccggga cagttggtgt | 120 |
| ttggccgtgc cgctgtctaa cttggtgtgc agagtgaatt gccgctgccg gagcggagag | 180 |
| aggcggagcg gccaggagag aggggatttc tgtcagcgcc ggcctcggga gctcggagac | 240 |
| atgaacggct tcacgcctga cgagatgagc gcggcggggg atgcggccgc cgcagtggcc | 300 |
| gcagtggtcg ctgccgcggc cgccgccgcc tcggcgggga acgggaccgg cgcgggcacc | 360 |
| ggggctgagg tgccgggcgc gggggcggtc tcagcggctg gccccccggg ggcggccggg | 420 |
| ccgggccccg ggcaactgtg ctgcctgcgg gaggatggtg agcggtgcgg ccgggcggca | 480 |
| ggcaacgcca gcttcagcaa gaggatccag aagagcatct cccagaagaa ggtgaagatc | 540 |
| gagctggata agagcgcaag gcatctttac atatgtgatt atcataaaaa cttaattcag | 600 |
| agtgttcgaa acagaagaaa gagaaaaggg agtgatgatg atggaggtga ttcacctgtt | 660 |
| caagatattg atacccagga ggttgattta taccaattac aagtaaatac acttaggaga | 720 |
| tacaaaagac acttcaagct accaaccaga ccaggactta taaagcaca acttgttgag | 780 |
| atagttggtt gccactttag gtctattcca gtgaatgaaa aagacacctt aacatatttc | 840 |
| atctactcag tgaagaatga caagaacaaa tcagatctca aggttgatag tggtgttcac | 900 |
| taggagacgt ggaattgaga ctaataactt ggatgttaac actgtttact gttttttcac | 960 |
| atgtagaaat gttctttgtg tattttttct acagaggatt ttctctgatt ttattttctt | 1020 |
| tgtttctgac tctaataatt agttggaaac tcatataaaa tgagctttcc taaattaaat | 1080 |
| ctattttaaa taaaggttat tactattaaa aaaaaaaaaa aaaaa | 1125 |

<210> SEQ ID NO 20
<211> LENGTH: 3608
<212> TYPE: DNA
<213> ORGANISM: Homo sapiens

<400> SEQUENCE: 20

| | |
|---|---|
| gcggccgctt cccccggcc gggccccgc cgccccgcgg tccccagagc gccaggcccc | 60 |
| cggggggagg gagggagggc gccgggccgg tgggagccag cggcgcgcgg tgggacccac | 120 |
| ggagccccgc gacccgccga gcctggagcc gggccgggtc ggggaagccg gctccagccc | 180 |
| ggagcgaact tcgcagcccg tcgggggggcg gcggggaggg ggcccggagc cggaggaggg | 240 |
| ggcggccgcg gcaccccg cctgtgcccc ggcgtccccg ggcaccatgc tgtccaactc | 300 |
| ccagggccag agcccgccgg tgccgttccc cgccccggcc ccgccgccgc agccccccac | 360 |
| ccctgccctg ccgcaccccc cggcgcagcc gccgccgccg ccccgcagc agttcccgca | 420 |
| gttccacgtc aagtccggcc tgcagatcaa gaagaacgcc atcatcgatg actacaaggt | 480 |
| caccagccag gtcctggggc tgggcatcaa cggcaaagtt ttgcagatct tcaacaagag | 540 |

```
gacccaggag aaattcgccc tcaaaatgct tcaggactgc cccaaggccc gcagggaggt      600
ggagctgcac tggcgggcct cccagtgccc gcacatcgta cggatcgtgg atgtgtacga      660
gaatctgtac gcaggagga agtgcctgct gattgtcatg gaatgtttgg acggtggaga      720
actctttagc cgaatccagg atcgaggaga ccaggcattc acagaaagag aagcatccga      780
aatcatgaag agcatcggtg aggccatcca gtatctgcat caatcaaca ttgcccatcg      840 ggatgtcaag cctgagaatc tcttatacac ctccaaaagg cccaacgcca tcctgaaact      900
cactgacttt ggctttgcca aggaaaccac cagccacaac tctttgacca ctccttgtta      960
tacaccgtac tatgtggctc agaagtgct gggtccagag aagtatgaca agtcctgtga     1020
catgtggtcc ctgggtgtca tcatgtacat cctgctgtgt gggtatcccc ccttctactc     1080
caaccacggc cttgccatct ctccgggcat gaagactcgc atccgaatgg ccagtatga     1140 atttcccaac ccagaatggt cagaagtatc agaggaagtg aagatgctca ttcggaatct     1200
gctgaaaaca gagcccaccc agagaatgac catcaccgag tttatgaacc acccttggat     1260
catgcaatca acaaaggtcc ctcaaacccc actgcacacc agccgggtcc tgaaggagga     1320
caaggagcgg tgggaggatg tcaagggtg tcttcatgac aagaacagcg accaggccac     1380
ttggctgacc aggttgtgag cagaggattc tgtgttcctg tccaaactca gtgctgtttc     1440
ttagaatcct tttattccct gggtctctaa tgggaccta aagaccatct ggtatcatct     1500
tctcattttg cagaagagaa actgaggccc agaggcggag ggcagtctgc tcaaggtcac     1560
gcagctggtg actggttggg gcagaccgga cccaggtttc ctgactcctg gcccaagtct     1620
cttcctccta tcctgcggga tcactggggg gctctcaggg aacagcagca gtgccatagc     1680
caggctctct gctgcccagc gctggggtga ggctgccgtt gtcagcgtgg accactaacc     1740
agcccgtctt ctctctctgc tcccacccct gccgccctca ccctgccctt gttgtctctg     1800
tctctcacgt ctctcttctg ctgtctctcc tacctgtctt ctggctctct ctgtacccctt    1860 cctggtgctg ccgtgccccc aggaggagat gaccagtgcc ttggccacaa tgcgcgttga     1920
ctacgagcag atcaagataa aaaagattga agatgcatcc aaccctctgc tgctgaagag     1980
gcggaagaaa gctcgggccc tggaggctgc ggctctggcc cactgagcca ccgcgccctc     2040
ctgcccacgg gaggacaagc aataactctc tacaggaata tattttttaa acgaagagac     2100
agaactgtcc acatctgcct cctctcctcc tcagctgcat ggagcctgga actgcatcag     2160
tgactgaatt ctgccttggt tctggccacc ccagagtggg agaggctggg aggttgggag     2220
gctgtggaga gaagtgagca aggtgctctt gaacctgtgc tcattttgca attttatcag     2280
taatttgact tagagttttt acgaaacctc ttttgttgtc cttgccccac tcctctccac     2340
cagacgcctt cctctctgga tactgcaaag gcttgtggtt tgttagaggg tatttgtgga     2400
aactgtcata gggattgtcc ctgtgttgtc ccatctgccc tccctgtttc tccacaacag     2460
cctggggttg tccccgctgg ctcacgcgtt ctgggagctc aaggccacct tggaggagga     2520
tgccacgcac ttcctctctc ggagccctca gacatctcca gtgtgccaga caaataggag     2580
tgagtgtatg tgtgtgtgtg tgtgtgtgtg tgtgcacacg tgtgtatgag tgcgcagatc     2640
tgtgcctggg atcgtgcatt tgaggggcca ggggcaggca gggctgcaga gggagacggc     2700
cctgctgggg cttaggaacc ttctcccttc ttgggtctgc cctgcccata ctgagcctgc     2760
caaagtgcct gggaagccca cccagattct gaaacaggcc ctctgtggcc tgtctctatt     2820
agctgggttc cgggaggcag agaggagtga ccgggcactg gcactgcgat caggaagact     2880
ggacccccag ccccagggc cccctcccc ccacttagtg ctggtcctag gtcctctgag     2940
```

| | | |
|---|---|---|
| gcactcatct actgaatgac ctctctactt ccccttcttg ccattattaa cccattttg | | 3000 |
| tttattttcc ttaaatttt agccatttct ccatgggcca ccgcccagct catgtaggtg | | 3060 |
| agcctgggca gcttctgttg gcagagcttt tgcatttcct gtgtttgtcc tgggttctgg | | 3120 |
| ggcatcagcc agctacccct tgtgggcaaa ggcagggcca cttttgaagt cttccctcag | | 3180 |
| atttccattg tgtggcctgg tgggtcaggg ggagtctttg caccaaagat gtcctgactt | | 3240 |
| tgcccccttg cccatcagcc atttgccatc accccaaaca actcagcttc ggggccggtg | | 3300 |
| aggggagggg cctcccccag cacagatgag gagcagctgg ggtaggctgt ctgtgccatg | | 3360 |
| gccccccact cccccttccc ttggaggag aggtggcagg aatacttcac ctttcctctc | | 3420 |
| cctcaggggc aggtggtgga ggggcgccca gggtcgtctt tgtgtatggg ggaaggcgct | | 3480 |
| gggtgcctgc agcgcctccc ttgtctcaga tggtgtgtcc agcactcgat tgttgtaaac | | 3540 |
| tgttgttttg tatgagcgaa attgtctta ctaaacagat ttaatagtta aaaaaaaaaa | | 3600 |
| aaaaaaaa | | 3608 |

<210> SEQ ID NO 21
<211> LENGTH: 678
<212> TYPE: DNA
<213> ORGANISM: Homo sapiens

<400> SEQUENCE: 21

| | | |
|---|---|---|
| ctcgcccaaa gaagactaca atctccaggg aaacctgggg cgtctcgcgc aaacgtccat | | 60 |
| aactgaaagt agctaaggca ccccagccgg aggaagtgag ctctcctggg gcgtggttgt | | 120 |
| tcgtgatcct tgcatctgtt acttagggtc aaggcttggg tcttgccccg cagacccttg | | 180 |
| ggacgacccg gccccagcgc agctatgaac ctggagcgag tgtccaatga ggagaaattg | | 240 |
| aacctgtgcc ggaagtacta cctgggggg tttgctttcc tgccttttct ctggttggtc | | 300 |
| aacatcttct ggttcttccg agaggccttc cttgtcccag cctacacaga acagagccaa | | 360 |
| atcaaaggct atgtctggcg ctcagctgtg ggcttcctct tctgggtgat agtgctcacc | | 420 |
| tcctggatca ccatcttcca gatctaccgg ccccgctggg gtgccctgg ggactacctc | | 480 |
| tccttcacca taccctggg caccccctga caacttctgc acatactggg gccctgctta | | 540 |
| ttctcccagg acaggctcct taaagcagag gagcctgtcc tgggagcccc ttctcaaact | | 600 |
| cctaagactt gttttcatgt cccacgttct ctgctgacat ccccaataa aggaccctaa | | 660 |
| ctttcaaaaa aaaaaaaa | | 678 |

<210> SEQ ID NO 22
<211> LENGTH: 2272
<212> TYPE: DNA
<213> ORGANISM: Homo sapiens

<400> SEQUENCE: 22

| | | |
|---|---|---|
| gaagcgactc tgagtcccgg gctcggagcg caggctcagc tccgcgctgc gagcgctacg | | 60 |
| ggcgcagggg cggggagccg gcccggagcg cagtttccag tggggccggg gtttcacccg | | 120 |
| ggccctctct gtttgaaccg aacccgacaa atgggcgcat gacgatggag agcagggaaa | | 180 |
| tggactgcta tctccgtcgc ctcaaacagg agctgatgtc catgaaggag gtgggtgatg | | 240 |
| gcttacagga tcagatgaac tgcatgatgg gtgcactgca agaactgaag ctcctccagg | | 300 |
| tgcagacagc actggaacag ctggagatct ctggagggg tcctgtgcca ggcagccctg | | 360 |
| aaggtcccag gacccagtgc gagcacccctt gttgggaggg tggcagaggt cctgccaggc | | 420 |

```
ccacagtctg ttcccctcc agtcaacctt ctcttggcag cagcaccaag tttccatccc      480
ataggagtgt ctgtggaagg gatttagccc ccttgcccag dacacagcca catcaaagct      540
gtgctcagca ggggccagag cgagtggaac cggatgactg gacctccacg ttgatgtccc      600
ggggccggaa tcgacagcct ctggtgttag gggacaacgt ttttgcagac ctggtgggca      660
attggctaga cttgccagaa ctggagaagg gtggggagaa gggtgagact ggggggggcac     720
gtgaacccaa aggagagaaa ggccagcccc aggagctggg ccgcaggttc gccctgacag      780
caaacatctt taagaagttc ttgcgtagtg tgcggcctga ccgtgaccgg ctgctgaagg      840
agaagccagg ctgggtgaca cccatggtcc ctgagtcccg aaccggccgc tcacagaagg      900
tcaagaagcg gagccttcc aagggctctg gacatttccc cttcccaggc accggggagc       960
acaggcgagg ggagaatccc cccacaagct gccccaaggc cctggagcac tcaccctcag     1020
gatttgatat taacacagct gtttgggtct gaatcctaga gacagaaagt tgactgagcc     1080
tgaaagggcc aggtcccagt gctgggcccc tggggaggag ggagggtggg cggtatggct     1140
ctcgaaagcc caactccaag ttcctttccc ccagaaagcg gggagaagcc agagttcttg     1200
gctcaggact gaagggaagg tggttgggag aggctgtctt gggggctagc tggtggagga     1260
ggtaagagta gctggagagt gagctgtgcg tgtgtgtgtg tgtgtgtgca tgtgtgtgtc     1320
tgtctggcat gcatgcactc actttggggc tggaggtgac agtaggtgag ggcagaggag     1380
gagatcagaa aatccctctg acatctccac tgccccaaa gacctccgtt gaacattctg      1440
tatggaaaag agccctggag catcaggttc cccagatagg cccccaaata aagacctgtc     1500
tatggctctc ccaaccttct gtcagcttct ttggcaagac attgctccag gcacagggac     1560
tgaaccccag gcctcctggg actggagcag cagtgaggca aaacccgacc tgctagccct     1620
ttctgccttg gaggtttcag tccataccctg gactctgaga aaatgagctg aataaggagt     1680
acagtgtgta aggagcagcc agggaagccc tagacactcc ccgcgtctcc cccatgcaca     1740
ggggaaggat gttgacatag cactgggctg tttgaatgcc ttttcatctc catggtctca     1800
tttgaaagtg agcgaggcag gcaggcatga tcccatttc cagataagga aacaagccta      1860
gatatgctac atgtccagga acaactgcag ccaggaggca aacagccta ggtctaactg      1920
cagagtagaa gctggaccct ggagttacca acactcctcc ccaacagttc ttagcgcccc     1980
gcaggctggg cgctgtggct cacgcctgta atcccagcac tttgggaggg caaggcaggc     2040
ggattacctg gggtcaggag ttcatgacca gcctggccaa catggtgaaa ccccgtctct     2100
actaaaaaaa tacgtaaaaa ttagccaggc gtggtggcac acgcctgtaa acccagctac     2160
tcgggaggct gaggcaggag aattgcttga gcccgggaga gggaggttgc agtgagccga     2220
gatcatgcca ctgcactcca gcctggctga cagagcaaga ctccccctgtc tc            2272
```

<210> SEQ ID NO 23
<211> LENGTH: 2358
<212> TYPE: DNA
<213> ORGANISM: Homo sapiens

<400> SEQUENCE: 23

```
ggagaggatc ccggagccgg tgagaattct ctgttttttc tctaccatcc tttccaggcc       60
ttttcctcac ctaatgagtc gtagagacga gggcccagag agtctgtaaa gtggctggtg      120
aaagattagt gtcccagggc cctacatccg ggaggtggtt cgggataaag agaactagtc      180
ttgggaacaa tgtaggtggg aacttaaggg aatgggagag cggcccatag aggtggacgg      240
agggcgcgat tggagtaaag cggaccctgt gtaggtatag agttgagtca agtggagtca      300
```

```
ctgcctctgt ccctctggtc agcgtgatgg ccagaggcct gggggccccc cactgggtgg    360
ccgtgggact gctgacctgg gcgaccttgg ggcttctggt ggctggactc ggggggtcatg   420 acgacctgca cgacgatctg caagaggact ccatggcca cagccacagg cactcacatg     480
aagatttcca ccatggtcac agccatgccc atggtcatgg ccacactcac gagagcatct    540
ggcatggaca tacccacgat cacgaccatg acattcaca tgaggattta caccatggcc     600
atagccatgg ctactcccat gagagcctct accacagagg acatggacat gaccatgagc    660
atagccatgg aggctatggg gagtctgggg ctccaggcat caagcaggac ctggatgctg    720
tcactctctg ggcttatgca ctgggggcca cagtgctgat ctcagcagct ccatttttg     780 tcctcttcct tatccccgtg gagtcgaact ctccccggca tcgctctcta cttcagatct    840
tgctcagttt tgcttccggt gggctcctgg gagatgcttt cctgcacctc attcctcatg    900
ctcttgaacc tcattctcac cacactctgg agcaacccgg acatggacac tcccacagtg    960
gccagggccc cattctgtct gtgggcctgt gggttctcag tggaattgtt gcctttcttg   1020
tcgtggagaa atttgtgaga catgtgaaag gaggacatgg tcacagtcat ggacatggac   1080
acgctcacag tcatacacgt ggaagtcatg gacatgaag acaagagcgt tctaccaagg    1140
agaagcagag ctcagaggaa gaaggaaagg aaacaagagg ggttcagaag aggcgaggag   1200
ggagcacagt acccaaagat gggccagtga gaccctcagaa cgctgaagaa gaaaaaagag   1260
gcttagacct gcgtgtgtcg gggtacctga atctggctgc tgacttggca cacaacttca   1320
ctgatggtct ggccattggg gcttcctttc gaggggccg gggactaggg atcctgacca    1380
caatgactgt cctgctacat gaagtgcccc acgaggtcgg ggactttgcc atcttggtcc   1440
agtctggctg caccaaaaag caggcgatgc gtctgcaact actgacagca gtaggggcac   1500
tggcaggcac agctgtgccc ttctcactga aggaggagca gtggacagtg aaattgcagg   1560
tggtgcaggt cctggctggg tcctgccatt tactgcaggt ggctttatct acgtagcaac   1620
agtgtctgtg ttgcccgagc tgctgaggga ggcatcacca ttgcaatcac ttctggaggt   1680 gctgggctg ctgggggagg ttatcatgat ggtgctgatt gcccaccttg agtgagggt     1740 ggataaacta ccctgcccca aacctctacc cctaactcca ggtcagggt gcgtagaggt    1800 tgggggccct ggccagggac atctgccaaa ggaaggaact gtagcctggg agcaatggtt   1860
actttggcat tagggccttc aagggctggc agtcttacag aggctggagc ggtgagaatg   1920
agaggccaga gggaccatag tgttgggcac tgtctgacca tgttgcattt ggaaggctaa   1980
atggggccat gaagaaggct ggaagggaca ggggtgatg gcagcctacc tggtgtcccc    2040
taccccacct gttctcggag aaccaagttg ctacacagga agttctccaa ggtccagttt   2100
cctttctccc accagttggt ggaggcttca gggaagacca gagtcctgga cagagaggg    2160 aacaggagga gtcggggata acatcaaac atcaatcgtg tgtcctgatt tgggagtgat   2220 tgggggatg gggtgggaga gggttaattg gtattctcat ggcctgattt ttttgtttc    2280 tattcctttt atatcactgt gtttgaatcg agggggaggg gtggtaaccg gaaataaaga   2340
cctccgatct tccgcccc                                                2358
```

<210> SEQ ID NO 24
<211> LENGTH: 1856
<212> TYPE: DNA
<213> ORGANISM: Homo sapiens

<400> SEQUENCE: 24

```
agccaaaaga ggaagggacc ggcctcccac gtccacaggg acctgacttc cacctctctg      60
cccagatttg cttatgtcac tgtcgccccg ggacggggag gtggggagct gagggcaagt     120
cgcgcccgcc cctgaaatcc cagccgccta gcgattggct gcaagggtct cggcttggcc     180
gcggattaat cacacccgag ggcttgaaag gtggctggga gcgccggaca cctcagacgg     240
acggtggcca gggatcaggc agcggctcag gcgaccctga gtgtgccccc accccgccat     300
ggcccggctg ctgcaggcgt cctgcctgct ttccctgctc ctggccggct tcgtctcgca     360
gagccgggga caagagaagt cgaagatgga ctgccatggt ggcataagtg gcaccattta     420
cgagtacgga gccctcacca ttgatgggga ggagtacatc cccttcaagc agtatgctgg     480
caaatacgtc ctctttgtca acgtggccag ctactgaggc ctgacgggcc agtacattga     540
actgaatgca ctacaggaag agcttgcacc attcggtctg gtcattctgg gctttccctg     600
caaccaattt ggaaaacagg aaccaggaga gaactcagag atccttccta ccctcaagta     660
tgtccgacca ggtggaggct ttgtccctaa tttccagctc tttgagaaag gggatgtcaa     720
tggagagaaa gagcagaaat tctacacttt cctaaagaac tcctgtcctc ccacctcgga     780
gctcctgggt acatctgacc gcctcttctg ggaacccatg aaggttcacg acatccgctg     840
gaactttgag aagttcctgg tggggccaga tggtataccc atcatgcgct ggcaccaccg     900
gaccacggtc agcaacgtca agatggacat cctgtcctac atgaggcggc aggcagccct     960
gggggtcaag aggaagtaac tgaaggccgt ctcatcccat gtccaccatg taggggaggg    1020
actttgttca ggaagaaatc cgtgtctcca accacactat ctacccatca cagacccctt    1080
tcctatcact caaggcccca gcctggcaca aatggatgca tacagttctg tgtactgcca    1140
ggcatgtggg tgtgggtgca atgtgggtgt ttacacacat gcctacaggt atgcgtgatt    1200
gtgtgtgtgt gcatgggtgt acagccacgt gtctacctat gtgtctttct gggaatgtgt    1260
accatctgtg tgcctgcagc tgtgtagtgc tggacagtga caacccttc tctccagttc    1320 tccactccaa tgataatagt tcacttatac ctaaacccaa aggaaaaacc agctctaggt    1380
ccaattgttc tgctctaact gatacctcaa ccttggggcc agcatctccc actgcctcca    1440
aatattagta actatgactg acgtcccag aagtttctgg gtctaccaca ctccccaacc     1500
ccccactcct acttcctgaa gggccctccc aaggctacat ccccacccca cagttctccc    1560
tgagagagat caacctccct gagatcaacc aaggcagatg tgcagcaag ggccacggac     1620 cccatggcag gggtggcgtc ttcatgaggg aggggcccaa agcccttgtg gcggacctc     1680 ccctgagcct gtctgagggg ccagcccttg gtgcattcag gctaaggccc ctgggcaggg    1740
atgccacccc tgctccttcg gaggacgtgc cctcaccct cactggtcca ctggcttgag     1800
actcaccccg tctgcccagt aaaagccttt ctgcagcaaa aaaaaaaaa aaaaaa         1856
```

<210> SEQ ID NO 25
<211> LENGTH: 2727
<212> TYPE: DNA
<213> ORGANISM: Homo sapiens

<400> SEQUENCE: 25

```
ggggacactg gatcacctag tgtttcacaa gcaggtacct tctgctgtag gagagagaga      60
actaaagttc tgaaagacct gttgcttttc accaggaagt tttactgggc atctcctgag     120
cctaggcaat agctgtaggg tgacttctgg agccatcccc gtttcccgc ccccaaaag      180 aagcggagat ttaacgggga cgtgcggcca gagctgggga aatgggcccg cgagccaggc    240
cggcgcttct cctcctgatg cttttgcaga ccgcggtcct gcagggcgc ttgctgcgtt     300
```

```
cacactctct gcactacctc ttcatgggtg cctcagagca ggaccttggt ctttccttgt      360
ttgaagcttt gggctacgtg gatgaccagc tgttcgtgtt ctatgatcat gagagtcgcc      420
gtgtggagcc ccgaactcca tgggtttcca gtagaatttc aagccagatg tggctgcagc      480
tgagtcagag tctgaaaggg tgggatcaca tgttcactgt tgacttctgg actattatgg      540
aaaatcacaa ccacagcaag gagtcccaca ccctgcaggt catcctgggc tgtgaaatgc      600
aagaagacaa cagtaccgag ggctactgga agtacgggta tgatgggcag gaccaccttg      660
aattctgccc tgacacactg gattggagag cagcagaacc cagggcctgg cccaccaagc      720
tggagtggga aaggcacaag attcgggcca ggcagaacag ggcctacctg gagagggact      780
gccctgcaca gctgcagcag ttgctggagc tggggagagg tgttttggac caacaagtgc      840
ctcctttggt gaaggtgaca catcatgtga cctcttcagt gaccactcta cggtgtcggg      900
ccttgaacta ctaccccag aacatcacca tgaagtggct gaaggataag cagccaatgg      960
atgccaagga gttcgaacct aaagacgtat tgcccaatgg ggatgggacc taccagggct     1020
ggataacctt ggctgtaccc cctggggaag agcagagata cgtgccag gtggagcacc      1080 caggcctgga tcagccctc attgtgatct gggagccctc accgtctggc acctagtca      1140 ttggagtcat cagtggaatt gctgttttg tcgtcatctt gttcattgga attttgttca      1200
taatattaag gaagaggcag ggttcaagag gagccatggg gcactacgtc ttagctgaac     1260
gtgagtgaca cgcagcctgc agactcactg tgggaaggag acaaaactag agactcaaag     1320
agggagtgca tttatgagct cttcatgttt caggagagag ttgaacctaa acatagaaat     1380
tgcctgacga actccttgat tttagccttc tctgttcatt tcctcaaaaa gatttcccca     1440
tttaggtttc tgagttcctg catgccggtg atccctagct gtgacctctc ccctggaact     1500
gtctctcatg aacctcaagc tgcatctaga ggcttccttc atttcctccg tcacctcaga     1560
gacatacacc tatgtcattt catttcctat ttttggaaga ggactcctta aatttggggg     1620
acttacatga ttcatttaa catctgagaa aagctttgaa ccctgggacg tggctagtca      1680
taaccttacc agatttttac acatgtatct atgcatttc tggacccgtt caacttttcc     1740
tttgaatcct ctctctgtgt tacccagtaa ctcatctgtc accaagcctt ggggattctt     1800
ccatctgatt gtgatgtgag ttgcacagct atgaaggctg tacactgcac gaatggaaga     1860
ggcacctgtc ccagaaaaag catcatggct atctgtgggt agtatgatgg gtgttttag     1920 caggtaggag gcaaatatct tgaaaggggt tgtgaagagg tgtttttct aattggcatg      1980 aaggtgtcat acagatttgc aaagtttaat ggtgccttca tttgggatgc tactctagta     2040
ttccagacct gaagaatcac aataattttc tacctggtct ctccttgttc tgataatgaa     2100
aattatgata aggatgataa aagcacttac ttcgtgtccg actcttctga gcacctactt     2160
acatgcatta ctgcatgcac ttcttacaat aattctatga gataggtact attatcccca     2220
tttctttttt aaatgaagaa agtgaagtag gccgggcacg gtggctcacg cctgtaatcc     2280
cagggtgctg agattacagg tgtgagccac cctgcccagc cgtcaaaaga gtcttaatat     2340
atatatccag atggcatgtg tttactttat gttactacat gcacttggct gcataaatgt     2400
ggtacaagca ttctgtcttg aagggcaggt gcttcaggat accatataca gctcagaagt     2460
ttcttcttta ggcattaaat tttagcaaag atatctcatc tcttcttta aaccattttc      2520 tttttttgtg gttagaaaag ttatgtgaaa aaaagtaaat gtgatttacg ctcattgtag     2580
aaaagctata aaatgaatac aattaaagct gttatttaat tagccagtga aaaactatta     2640
```

| | |
|---|---|
| acaacttgtc tattacctgt tagtattatt gttgcattaa aaatgcatat actttaataa | 2700 |
| atgtatattg tattgtaaaa aaaaaaa | 2727 |

<210> SEQ ID NO 26
<211> LENGTH: 879
<212> TYPE: DNA
<213> ORGANISM: Homo sapiens

<400> SEQUENCE: 26

| | |
|---|---|
| ctcctcacag aagcctggag ctgggcatcc aagaagaagc agcctcattt gttttctggt | 60 |
| gtcatcgtag gtggccacct atggcttttg ggaatgtaaa aagggcagct ctctggcatg | 120 |
| ttcctgactg aggatctcat aacatttaac ttgaggaact cctcctttt ccagctttgg | 180 |
| gagtcaagct tctcacctgg ggcgggtggg ttctgcacca ccctcccacc ctccttcctc | 240 |
| cgtgtggacg atagagccac atccagcacc acggacagct cccgggcgcc ttcatctcct | 300 |
| cgtcctccag gcagcacaag ccattgtgga atctccacca ggtgtacaga acggtgcctc | 360 |
| tgcgtcctgc cactcaggac ctctcaagtc cccgatgtga tggctcctca gcatgatcag | 420 |
| gagaaattcc atgatcttgc ttattcctgt cttgggaagt ccttctccat gtctaaccaa | 480 |
| gatctatatg gctatagcac cagctctttg gctcttggct tggcatggct aagttgggag | 540 |
| accaaaaaga agaatgtact tcatctggtt gggctggatt ccctctgata agccttccca | 600 |
| gttgactgaa agatgaggct aggctctagc aagttgaagt caaaccagct ccttcaagaa | 660 |
| gctttgagca gaatgaagtg gggaggaccc agcttccagc ccaggaagcc cactgtacct | 720 |
| ggagccatct gggataagac tttgacccat gactcccata tccacagcct gtccatccta | 780 |
| gcccatccca gtttatcctg tatcatttga gctgggattc ccacatcctc tgagttggaa | 840 |
| gtcccatctc aagtcttcaa taaagactct tgaatattg | 879 |

<210> SEQ ID NO 27
<211> LENGTH: 3287
<212> TYPE: DNA
<213> ORGANISM: Homo sapiens

<400> SEQUENCE: 27

| | |
|---|---|
| atggcgctgg ctgtcttgcg ggtcctggag ccctttccga ccgagacacc cccgttggca | 60 |
| gtgctgctgc cacccggggg cccgtggccg cggcggagc tgggcctggt gctgccctg | 120 |
| aggcctgcag gggagagccc ggcagggccg gcgctgctgg tggcagccct ggaggggccg | 180 |
| gacgcgggca ccgaagagca gggtcccggg ccgccgcagc tactggttag ccgcgcgctg | 240 |
| ctgcggctcc tggcactggg ctccggggcc tgggtgcggg cgcgggcggt gcggcggccc | 300 |
| ccggcgctag gttgggcact gcttggcacc tcgctgggc ctgggctcgg accgcgagtc | 360 |
| gggccgctgc tggtgaggcg cggagagacc ctcccagttc ccggaccgcg ggtgctggag | 420 |
| acgcggccgg cgttgcaagg gctgctgggc ccagggactc ggctggctgt gactgagctc | 480 |
| cgcgggcggg ccagactgtg tccagagtct ggggacagca gtcggccccc accccgcccc | 540 |
| gtggtgtcct cctttgcggt ttctggcaca gtgcggcgac tccagggagt tctgggaggg | 600 |
| actggagatt cactaggggt gagccggagc tgtctccgtg gccttggcct cttccagggc | 660 |
| gaatgggtgt gggtggccca ggccagagag tcatcgaaca cttcacagcc gcacttggct | 720 |
| aggtgcagg tcctagaacc tgctgggac ctctctgata gactgggacc cggctctgga | 780 |
| ccgctgggag agccctcgc tgacggactg gcgcttgtcc ctgccacttt ggcttttaat | 840 |
| cttggctgtg acccccctgga aatgggagag ctcagaattc agaggtactt ggaaggctcc | 900 |

```
atcgcccctg aagacaaagg aagctgctca ttgctgcctg ggcctccatt tgccagagag    960
ttacacatcg aaattgtgtc ttctccccac tacagcacta atggaaatta tgacggtgtt   1020
cttttaccggc actttcagat acccagggta gtccaggaag gggatgttct atgtgtgcca   1080
acaattgggc aagtagagat cctggaagga agtccagaga aactgcccag gtggcgggaa   1140
atgttttta aagtgaagaa aacagttggg gaagctccag atggaccagc cagtgcctac   1200
ttggccgaca ccaccatac ctccttgtac atggtgggtt ctaccctgag ccctgttcca   1260
tggctccctt cagaggaatc cactctctgg agcagtttgt ctcctccagg cctggaggcc   1320
ttggtgtctg aactctgtgc tgtcctgaag cctcgcctcc agccagggg tgccctgctg    1380
acaggaacta gcagtgtcct tctacggggc ccccaggct gtgggaagac cacagtagtt    1440
gctgctgcct gtagtcacct tgggctccac ttactgaagg tgccctgctc cagcctctgt   1500
gcagaaagta gtgggctgt ggagacaaaa ctgcaggcca tcttctcccg ggcccgccgt    1560
tgccggcctg cagtcctgtt gctcacagct gtggaccttc tgggccggga ccgtgatggg   1620
ctgggtgagg atgcccgtgt gatggctgtg ctgcgtcacc tcctcctcaa tgaggacccc   1680
ctcaacagct gccctcccct catggttgtg gccaccacaa gccgggccca ggacctgcct   1740
gctgatgtgc agacagcatt tcctcatgag ctcgaggtgc ctgctctgtc agaggggcag   1800
cggctcagca tcctgcgggc cctcactgcc accttcccc tgggccagga ggtgaacttg    1860
gcacagctag cacggcggtg tgcaggcttt gtggtagggg atctctatgc ccttctgacc   1920
cacagcagcc gggcagcctg caccaggatc aagaactcag gtttggcagg tggcttgact   1980
gaggaggatg aggggagct gtgtgctgcc ggctttcctc tcctggctga ggactttggg   2040
caggcactgg agcaactgca gacagctcac tcccaggccg ttggagcccc caagatcccc   2100
tcagtgtcct ggcatgatgt gggtgggctg caggaggtga agaaggagat cctggagacc   2160
attcagctcc ccctggagca ccctgagcta ctgagcctgg gcctgagacg ctcaggcctt   2220
ctgctccatg ggcccctgg caccggcaag acccttctgg ccaaggcagt agccactgag   2280
tgcagcctta ccttcctcag cgtgaagggg ccagagctca ttaacatgta tgtgggccaa   2340
agtgaggaga atgtgcggga agtgtttgcc agggccaggg ctgcagctcc atgcattatc   2400
ttctttgatg aactggactc tttggcccca agccgggggc gaagtggaga ttctggagga   2460
gtgatggaca gggtggtgtc tcagctcctt gccgagctag atgggctgca cagcactcag   2520
gatgtgtttg tgattggagc caccaacaga ccagatctcc tggaccctgc ccttctgcgg   2580
cctggcagat ttgacaagct ggtgtttgtg ggggcaaatg aggaccgggc ctcccagcta   2640
cgcgttctaa gtgccatcac acgcaaattc aagctagagc catctgtgag cctggtaaac   2700
gtgctagatt gctgccctcc ccagctgacg ggcgcggacc tctactctct ctgctctgat   2760
gctatgacag ctgccctcaa acgcaggggtt catgacctgg aggaagggct ggaacaaggt   2820
agctcagcac tgatgctcac catggaggac ttgctgcagg ctgccgcccg gctgcaaccc   2880
tcagtcagtg agcaggagct gctccggtac aagcgcatcc agcgcaagtt tgctgcctgc   2940
taggagcccc ccagggtctg gaccccgct cagcatggct gcaggtacct tgatagccca    3000
cagagagatc tgggaaggaa gggctcctcc tcaggctgct gccaacccac ctggaggcca   3060
cctccctcca ggagatccca gggtgcaaag tggcattgag acagcagcaa cagctcaaga   3120
gatatctcct gcctacttgc ccctccttcc aggccggctc taagagaaag gcccatctac   3180
tcaggaagag ggccagggcc ttgggttctg gggattgggc cctgagaggg ctagttctgt   3240
```

```
ggctgaaaat aaagcatgtc ccgccccta aaaaaaaaaa aaaaaaa            3287

<210> SEQ ID NO 28
<211> LENGTH: 7239
<212> TYPE: DNA
<213> ORGANISM: Homo sapiens

<400> SEQUENCE: 28
cggggcagcc gagggcccct gactcggctc ctcgcggcga catggatcgg atggccagct      60
ccatgaagca ggtgcccaac ccactgccca aggtgctgag ccggcgcggg gtcggcgctg     120
ggctggaggc ggcggagcgc gagagcttcg agcggactca gactgtcagc atcaataagg     180
ccattaatac gcaggaagtg gctgtaaagg aaaaacacgc cagaacgtgc atactgggca     240
cccaccatga gaaagggca cagaccttct ggtctgttgt caaccgcctg cctctgtcta     300
gcaacgcagt gctctgctgg aagttctgcc atgtgttcca caaactcctc cgagatggac     360
acccgaacgt cctgaaggac tctctgagat acagaaatga attgagtgac atgagcagga     420
tgtgggccca cctgagcgag gggtatggcc agctgtgcag catctacctg aaactgctaa     480
gaaccaagat ggagtaccac accaaaaatc ccaggttccc aggcaacctg cagatgagtg     540
accgccagct ggacgaggct ggagaaagtg acgtgaacaa cttttttccag ttaacagtgg     600 agatgtttga ctacctggag tgtgaactca acctcttcca aacagtattc aactccctgg     660
acatgtcccg ctctgtgtcc gtgacggcag cagggcagtg ccgcctcgcc ccgctgatcc     720
aggtcatctt ggactgcagc cacctttatg actacactgt caagcttctc ttcaaactcc     780
actcctgcct cccagctgac acccctgcaag gccaccggga ccgcttcatg gagcagttta     840
caaagttgaa agatctgttc taccgctcca gcaacctgca gtacttcaag cggctcattc     900
agatccccca gctgcctgag aacccaccca acttcctgcg agcctcagcc ctgtcagaac     960
atatcagccc tgtggtggtg atccctgcag aggcctcatc ccccgacagc gagccagtcc    1020
tagagaagga tgacctcatg gacatggatg cctctcagca gaatttatttt gacaacaagt    1080 ttgatgacat ctttggcagt tcattcagca gtgatccctt caatttcaac agtcaaaatg    1140
gtgtgaacaa ggatgagaag gaccacttaa ttgagcgact atacagagag atcagtggat    1200
tgaaggcaca gctagaaaac atgaagactg agagccagcg ggttgtgctg cagctgaagg    1260
gccacgtcag cgagctggaa gcagatctgg ccgagcagca gcacctgcgg cagcaggcgg    1320
ccgacgactg tgaattcctg cgggcagaac tggacgagct caggaggcag cgggaggaca    1380 ccgaaaggc tcagcggagc ctgtctgaga tagaaaggaa agctcaagcc aatgaacagc    1440
gatatagcaa gctaaaggag aagtacagcg agctggttca gaaccacgct gacctgctgc    1500
ggaagaatgc agaggtgacc aaacaggtgt ccatggccag acaagcccag gtagatttgg    1560
aacgagagaa aaaagagctg gaggattcgt tggagcgcat cagtgaccag ggccagcgga    1620
agactcaaga acagctggaa gttctagaga gcttgaagca ggaacttgcc acaagccaac    1680
gggagcttca ggttctgcaa ggcagcctgg aaacttctgc ccagtcagaa gcaaactggg    1740
cagccgagtt cgccgagcta gagaaggagc gggacagcct ggtgagtggc gcagctcata    1800
gggaggagga attatctgct cttcggaaag aactgcagga cactcagctc aaactggcca    1860
gcacagagga atctatgtgc cagcttgcca agaccaacg aaaaatgctt ctggtgggt     1920 ccaggaaggc tgcggagcag gtgatacaag acgccctgaa ccagcttgaa gaacctcctc    1980
tcatcagctg cgctgggtct gcagatcacc tcctctccac ggtcacatcc atttccagct    2040
gcatcgagca actggagaaa agctggagcc agtatctggc ctgcccagaa gacatcagtg    2100
```

```
gacttctcca ttccataacc ctgctggccc acttgaccag cgacgccatt gctcatggtg    2160
ccaccacctg cctcagagcc ccacctgagc ctgccgactc actgaccgag cctgtaagc     2220
agtatggcag ggaaaccctc gcctacctgg cctccctgga ggaagaggga agccttgaga    2280
atgccgacag cacagccatg aggaactgcc tgagcaagat caaggccatc ggcgaggagc    2340
tcctgcccag gggactggac atcaagcagg aggagctggg ggacctggtg gacaaggaga    2400
tggcggccac ttcagctgct attgaaactg ccacggccag aatagaggag atgctcagca    2460
aatcccgagc aggagacaca ggagtcaaat tggaggtgaa tgaaaggatc cttggttgct    2520
gtaccagcct catgcaagct attcaggtgc tcatcgtggc ctctaaggac ctccagagag    2580
agattgtgga gagcggcagg ggtacagcat cccctaaaga gttttatgcc aagaactctc    2640
gatggacaga aggacttatc tcagcctcca aggctgtggg ctggggagcc actgtcatgg    2700
tggatgcagc tgatctggtg gtacaaggca gagggaaatt tgaggagcta atggtgtgtt    2760
ctcatgaaat tgctgctagc acagcccagc ttgtggctgc atccaaggtg aaagctgata    2820
aggacagccc caacctagcc cagctgcagc aggcctctcg gggagtgaac caggccactg    2880
ccggcgttgt ggcctcaacc atttccggca aatcacagat cgaagagaca gacaacatgg    2940
acttctcaag catgacgctg acacagatca aacgccaaga gatggattct caggttaggg    3000
tgctagagct agaaaatgaa ttgcagaagg agcgtcaaaa actgggagag cttcggaaaa    3060
agcactacga gcttgctggt gttgctgagg gctgggaaga aggaacagag gcatctccac    3120
ctacactgca agaagtggta accgaaaaag aatagagcca aaccaacacc ccatatgtca    3180
gtgtaaatcc ttgttaccta tctcgtgtgt gttatttccc cagccacagg ccaaatcctt    3240
ggagtcccag gggcagccac accactgcca ttacccagtg ccgaggacat gcatgacact    3300
tccaaagact ccctccatag cgacacccett tctgtttgga cccatggtca tctctgttct    3360
tttcccgcct cccagttag catccaggct ggccagtgct gcccatgagc aagcctaggt    3420
acgaagaggg gtggtgggggg gcagggccac tcaacagaga ggaccaacat ccagtcctgc    3480
tgactatttg accccacaa caatgggtat ccttaataga ggagctgctt gttgtttgtt     3540
gacagcttgg aaagggaaga tcttatgcct tttcttttct gttttcttct cagtctttc     3600
agtttcatca tttgcacaaa cttgtgagca tcagagggct gatggattcc aaaccaggac    3660
actaccctga gatctgcaca gtcagaagga cggcaggagt gtcctggctg tgaatgccaa    3720
agccattctc cccctctttg ggcagtgcca tggatttcca ctgcttctta tggtggttgg    3780
ttggggttttt tggttttgtt tttttttta agtttcactc acatagccaa ctctcccaaa    3840
gggcacaccc ctggggctga gtctccaggg ccccccaact gtggtagctc cagcgatggt    3900
gctgccagg cctctcggtg ctccatctcc gcctccacac tgaccaagtg ctggcccacc    3960
cagtccatgc tccagggtca ggcggagctg ctgagtgaca gctttcctca aaaagcagaa    4020
ggagagtgag tgccttccc tcctaaagct gaatcccggc ggaaagcctc tgtccgcctt    4080
tacaagggag aagacaacag aaagagggac aagagggttc acacagccca gttcccgtga    4140
cgaggctcaa aaacttgatc acatgcttga atggagctgg tgagatcaac aacactactt    4200
ccctgccgga atgaactgtc cgtgaatggt ctctgtcaag cgggccgtct cccttggccc    4260
agagacggag tgtgggagtg attcccaact ccttctctgca gacgtctgcc ttggcatcct    4320
cttgaatagg aagatcgttc caccttctac gcaattgaca aacccggaag atcagatgca    4380
attgctccca tcagggaaga accctatact tggtttgcta cccttagtat ttattactaa    4440
```

```
cctcccttaa gcagcaacag cctacaaaga gatgcttgga gcaatcagaa cttcaggtgt    4500
gactctagca aggctcatct ttctgcccgg ctacatcagc cttcaagaat cagaagaaag    4560
gccaaggtgc tggactgtta ctgacttgga tcccaaagca aggagatcat ttggagctct    4620
tgggtcagag aaaatgagaa aggacagagc cagcggctcc aactcctttc agccacatgc    4680
cccaggctct cgctgccctg tggacaggat gaggacagag ggcacatgaa cagcttgcca    4740
gggatgggca gcccaacagc acttttcctc ttctagatgg accccagcat ttaagtgacc    4800
ttctgatctt ggaaaaacag cgtcttcctt ctttatctat agcaactcat tggtggtagc    4860
catcaagcac ttcccaggat ctgctccaac agaatattgc taggttttgc tacatgacgg    4920
gttgtgagac ttctgtttga tcactgtgaa ccaaccccca tctccctagc ccaccccct    4980 ccccaactcc ctctctgtgc attttctaag tgggacattc aaaaaactct ctcccaggac    5040
ctcggatgac catactcaga cgtgtgacct ccatactggg ctaaggaagt atcagcacta    5100
gaaattgggc agtcttaatg ttgaatgctg ctttctgctt agtatttttt tgattcaagg    5160
ctcagaagga atggtgcgtg gcttccctgt cccagttgtg gcaactaaac caatcggtgt    5220
gttcttgatg cgggtcaaca tttccaaaag tggctagtcc tcacttctag atctcagcca    5280
ttctaactca tatgttccca attaccaagg ggtggccggg cacagtggct cacgcctgta    5340
atcccagcac tttgagaggc tgaggtggta ggatcacctg aggtcaggag ttcaagacca    5400
gcctgtccaa catggtgaaa ccccatctc tactaaaaat accaaaaatt agccgagcgt    5460
agtgacgggt gccgtaatc ccagctactc aggaggctga cagagagaa tcacctgaac    5520 cccagaggca gaggttgcag tgagctgaga tcacgccatt gtactccagc ctgggcaaca    5580
agagcaaaac tccgtctcaa aaaaaaaaa aaattacaaa tggggcaaac agtctagtgt    5640
aatggatcaa attaagattc tctgcccagc cgggcacagt ggcgcatgcc tgtaatccca    5700
gaactttggg aggccaagac gggatgattg cttgagctca ggagtttgag accaggctgg    5760
gcatcatagc aagacctcat ctctactaaa attcaaaaac aaaattagcc gggcatgatg    5820
gtgcatgcct gtagtctcag ctagttgggg agctaaggtg ggagaattgc ttgagcttgg    5880
gaagtcgagg ctgcagtcag ccctgattgt gccagtgcac tccggcctgg gtgacagagt    5940
gagaccctgt ctcaaaaaaa aaaagattct gtgtcagagc ccagcccagg agtttgaggc    6000
tgcaatgagc catgatttcc cactgcactc cagcctgagt gacagagcga gactccatct    6060
ctttaaaaac aaacaaaaaa ttatctgaat gatcctgtct ctaaaagaa gccacagaaa    6120 tgtttaaaaa cttcatcgac ttagcctgag tcataacggt taagaaagca cttaaacaga    6180
agcagaggct aattcagtgt cacatgagga agtagctgtc agatgtcaca taattacttt    6240
cgtaatagct cagattagaa tggctacccc attctctaga caaatcaaa ttgtcctatt    6300 gtgactcttc taaaaatgaa gatgaagagc tatttaatga cacaccttgg attaaaacgg    6360
gaatcacatc ttaaagctaa aaatgaacct gcaagccttc taaatgagtc actgagcatc    6420
actagtgaca agtctcgggt gagcgtaaat gggtcatgac aagatgggac agcaacaaaa    6480
tcatggctta ggatcgacaa gaagttaaaa aacagctgca tctgttactt aagtttgtaa    6540
gacagtgccc tgagacctct agagaaaaga tgtttgttta cataagagaa agaggccaga    6600
catggtgtct cacacgttta atcccagcac tttgggaggc aggggcgggt ggatcacctg    6660
aggtcaggag ttcaagacta gcctggccaa catggtgaaa cccgtctct actaaaaata    6720 caaaaattag ccgggcatgg tggcaggcgc ctataatccc agctactggg gaggctgagg    6780
caggagaatc acttgaaccc ggggacaga ggttgtagtg agccaagatc gcaccactgc    6840
```

```
actccagcct gggtcacaga gtgagactcc atctcaaaaa aaaaaaagag agagagagag      6900
aaagaaatag aagagaagag ccatcttggc agggttattt tatatctgag caaggagttt      6960
aaatgagact agtttagatt gtctgctgat gcagccgtcc atagcagtac ccctaaaatc      7020
ccaccagaat acgggtccct ctaacccagt ggctggaaga accactgtct agagcaactt      7080
ttcttggaac tgtcccagct accaagtcag acaccaaggt ttatgccacc aggtaacacg      7140
ggaatcacag gtacatgtcg ctccggtcag attagttggc tttggcccct cgaccctgtg      7200
caggagctag ttctcagctt gcagctggaa gttccctct                             7239
```

<210> SEQ ID NO 29
<211> LENGTH: 21
<212> TYPE: DNA
<213> ORGANISM: Homo sapiens

<400> SEQUENCE: 29

```
tgactggcag atccagaggt t                                                   21
```

<210> SEQ ID NO 30
<211> LENGTH: 21
<212> TYPE: DNA
<213> ORGANISM: Homo sapiens

<400> SEQUENCE: 30

```
gtagaatatg gacaggaaca c                                                   21
```

<210> SEQ ID NO 31
<211> LENGTH: 21
<212> TYPE: DNA
<213> ORGANISM: Homo sapiens

<400> SEQUENCE: 31

```
cctgaagtgt aacaccccag a                                                   21
```

<210> SEQ ID NO 32
<211> LENGTH: 21
<212> TYPE: DNA
<213> ORGANISM: Homo sapiens

<400> SEQUENCE: 32

```
tccctctcca gcacttctag t                                                   21
```

<210> SEQ ID NO 33
<211> LENGTH: 31
<212> TYPE: DNA
<213> ORGANISM: Homo sapiens

<400> SEQUENCE: 33

```
tgctggagct gggacccagc attgaggagg a                                        31
```

<210> SEQ ID NO 34
<211> LENGTH: 27
<212> TYPE: DNA
<213> ORGANISM: Homo sapiens

<400> SEQUENCE: 34

```
tcagacacac acaacttcag tcgatag                                             27
```

METHOD FOR DIAGNOSIS AND/OR PROGNOSIS OF A SEPTIC SYNDROME

The present invention relates to a method for the diagnosis and/or prognosis of a septic syndrome. The invention also relates to a kit for the diagnosis and/or prognosis of a septic syndrome.

Septic syndrome, a systemic response to infection, represents one of the primary causes of mortality in intensive care units. It can result from a bacterial, viral, fungal or parasitic infection. Among this septic syndrome, the following can be distinguished in increasing order of seriousness: sepsis, severe sepsis and septic shock. In 1992, a group of experts thus proposed criteria for defining these three clinical syndromes (R. C. Bone et al, The ACCP/SCCM Consensus Conference Committee. American College of Chest Physicians/Society of Critical Care Medicine. *Chest* 101 (6):1644-1655, 1992):

sepsis is thus an inflammatory systemic response related to an infection, severe sepsis is sepsis accompanied by the dysfunction of at least one organ, septic shock is severe sepsis associated with persistent hypotension and can be defined by:
 the presence of an identified infectious site,
 a generalized inflammatory response that manifests itself by means of at least three of the following signs: a) temperature above 38° C. or below 36° C.; b) heart rate above 90 beats per minute; c) breathing rate above 20 breaths per minute; d) leukocyte count above 12 000/mm$^3$ or below 4000/mm$^3$,
 persistent hypotension despite appropriate filling and vasopressive treatments.

In general, the signs of a sepsis, of a severe sepsis and of a septic shock are similar, and the difference between these three situations lies mainly in the degree to which all the vital functions are disturbed. During a septic shock, a drop in arterial pressure, tachycardia, polypnea, blotchy skin, hypothermia or hyperthermia, shivering are principally observed. These signs are also accompanied by a dysfunction of "target" organs, with impairment of the function of organs remote from the infectious site (kidneys, lungs, central nervous system, digestive system and hematological system most commonly affected), reflected by oliguria (<0.5 ml/kg/h), renal insufficiency, hypoxemia, thrombocytopenia, agitation and confusion.

The evolution of a septic syndrome from the stage of sepsis to a stage of severe sepsis, and then of septic shock, is not systematic since approximately 64% of septic patients develop a severe sepsis, and 23% of patients in severe sepsis evolve to septic shock. Before this ultimate step of septic shock, the patient should be prescribed treatments in order to interrupt and reverse the physiopathological process. It is thus necessary to restore a satisfactory hemodynamic state and to ensure effective ventilation. It is also necessary to have in hand the symptomatic treatment of the shock and an antibiotic treatment that, as soon as possible, is appropriate to the bacteriological data.

It thus appears that, while certain patients who develop a septic syndrome, and in particular a septic shock, can be reanimated by means of a relatively simple treatment, such as a treatment with broad-spectrum antibiotics set up before the results of the bacteriological tests that indicate the infectious source, other patients, who develop a much more serious septic syndrome, require a drastic and expensive treatment, such as an injection of activated protein C, for which the cost of the injection is very high. Such treatments are not only expensive, but also expose the patients to risks of very considerable adverse effects (clotting problems, etc.). This treatment should therefore only be proposed to patients with a poor prognosis who absolutely require said treatment.

As a result, the early diagnosis of a septic syndrome is essential and makes it possible to propose a treatment suited to the patient. Furthermore, the prognosis of the septic syndrome, and in particular of a septic shock, is essential in order to provide each patient with a suitable treatment, and to discriminate, as soon as possible, between patients who have a septic syndrome with a poor prognosis, and who require extensive therapy, and patients with a good prognosis. Finally, it is also very advantageous to monitor patients at risk of developing a sepsis, such as patients who have undergone surgery or a transplant, or immunodepressed patients, in order to be able to intervene as early as possible before any major clinical signs.

Currently, the diagnosis and the prognosis of a septic syndrome, and in particular of a septic shock, are essentially based on the number of visceral failures, the response to the symptomatic treatment, and the degree to which the initial infectious site and any possible secondary sites are accessible to medical and/or surgical therapy.

This has the drawback, however, of being applicable only to an advanced stage of septic syndrome, and in particular septic shock, reducing the patient's chances of survival.

The diagnosis and the prognosis of a septic syndrome can also be based on the detection of certain proteins or soluble factors involved in this syndrome. Thus, the assaying of certain cytokines, involved during the development of a septic syndrome, can be a means of diagnosing and of forming a prognosis of a septic syndrome.

Some authors have thus described a positive correlation between the plasma content of IL-1 (interleukin-1) and a septic syndrome with a poor prognosis (Thijs & Hack, Intensive Care Med 31: S258-263, 1995). However, other authors have found no correlation between II-1 and a poor prognosis for septic syndrome, suggesting a great variability of this factor. Furthermore, high dosages of TNF (tumor necrosis factor) have also been associated with a poor prognosis (Casey et al., Ann Intern Med. 1993. 119:771-778). TNF-α then IL-1β are the first two pro-inflammatory cytokines released by monocytes after a septic state has been triggered.

Other authors have shown that the plasma IL-10 (interleukin-10) content is higher in patients developing a sepsis with a poor prognosis, whereas it significantly decreases in patients presenting a sepsis with a good prognosis, and is undetectable in normal patients (Van der Poll, J. Infect. Dis. 175:118-122, 1997). IL-10 is a very important anti-inflammatory cytokine which, by virtue of its ability to inhibit the production of TNF-α and of IL-1β, participates in setting up the state of immunoparalysis. However, since this increase in the IL-10 content is detectable only in 80% of patients in septic shock, the sole detection of this factor remains insufficient for giving a prognosis of the evolution of septic shock.

Mention may also be made of U.S. Pat. No. 6,303,321, which describes a method for the prognosis of the severity of a septic syndrome comprising measuring the serum concentration of HMG1 (high mobility group 1 protein) by means of an ELISA-type immunoblotting technique. HMG1 is, unlike TNF-α and IL-1β, described as a late pro-inflammatory mediator of septic syndromes. A high concentration of HMG1 is correlated with a poor prognosis, the serum HMG1 concentration not being detected in normal patients.

Post-transcriptional regulation of the HMG1 gene has, on the other hand, been described in the mouse, suggesting that the expression of this gene should be analyzed only at the protein level (Wang et al, Science, 1999, vol 285, p 248-251).

Patent application WO 04/108957 provides a method for the prognosis of a septic syndrome according to which the expression of at least two target genes chosen from: IL-10, TGFβ, HMG1, T-bet, IL-1β, TNFα and GATA-3, is determined. The use of such a panel makes it possible to categorize patients with a good prognosis and patients with a poor prognosis at a rate of more than 80%. It would, however, be necessary to further increase this categorization percentage, in particular as regards the categorization of patients with a poor prognosis, in order to provide them with a drastic treatment as soon as possible.

The present invention proposes to solve the drawbacks of the prior art by providing a novel reliable tool for the diagnosis and/or prognosis of a septic syndrome, such as, in particular, a septic shock.

Surprisingly, the inventors have demonstrated that the analysis of the expression of target genes selected from 28 genes, as presented in table 1 hereinafter, is very relevant for discriminating between patients which a good prognosis and patients with a poor prognosis. The use of such a panel makes it possible in particular to categorize patients with a poor prognosis, at a rate of 100%.

TABLE 1 list of the 28 genes according to the invention

| SEQ ID No. | Gene name | GENBANK No |
|---|---|---|
| 1 | chemokine (C-X3-C motif) receptor 1 | NM_001337 |
| 2 | T cell receptor delta diversity 3 | X72501 |
| 3 | KIAA0882 protein | NM_015130 |
| 4 | T-cell lymphoma invasion and metastasis 1 | NM_003253 |
| 5 | Interleukin 1, beta | NM_000576 |
| 6 | Carbonyl reductase 1 | NM_001757 |
| 7 | TIR domain containing molecule 1 | NM_182919 |
| 8 | FYN tyrosine kinase protooncogene | NM_002037 |
| 9 | Heparanase | NM_006665 |
| 10 | SRY (Sex determining region Y) box 4 | NM_003107 |
| 11 | Interleukin 2 receptor, beta | NM_000878 |
| 12 | Raft-linking protein | NM_015150 |
| 13 | CGI-40 protein Homo sapiens SID1 transmembrane family, member 2 | NM_015996 |
| 14 | glucose-6-phosphatase catalytic subunit 3 | NM_138387 |
| 15 | Mannosidase alpha, class 1A member 2 | NM_006699 |
| 16 | Myeloid differentiation primary response gene (88) | NM_002468 |
| 17 | Ribosomal protein L6 | NM_000970 |
| 18 | Ribosomal protein L10a | NM_007104 |
| 19 | sin3 -associated polypeptide, 30 kDa | NM_003864 |
| 20 | Mitogen activated protein kinase-activated protein kinase 2 | NM_004759 |
| 21 | Presenilin enhancer 2 | NM_172341 |
| 22 | Hypothetical protein LOC55924 | NM_019099 |
| 23 | Solute carrier family 39 (zinc transporter member 7) | NM_006979 |
| 24 | Glutathione peroxidase 3 (plasma) | NM_002084 |
| 25 | Hemochromatosis | NM_000410 |
| 26 | Transcriptional activator of the cfos promoter | NM_006365 |
| 27 | peroxisomal biogenesis factor 6 | NM_000287 |
| 28 | Huntingtin interacting protein | NM_005338 |

Several variants sometimes exist for the same target gene. In the present invention, all the variants are relevant. It is clearly understood that, if various isoforms of these genes exist, all the isoforms are relevant for the present invention, and not only those presented in the above table. In this respect, it should in particular be noted that three variants exist for the target gene of SEQ ID No. 8; only the first variant is presented in the above table, but the second variant, the Genbank accession number of which is NM_153047, and the third variant, the Genbank number of which is NM_153048, are just as relevant for the purpose of the present invention.

Similarly, two variants exist for the target gene of SEQ ID No. 20; only the first variant is presented in the above table, but the second variant, the Genbank accession number of which is NM_032960, is just as relevant for the purpose of the present invention. Similarly, two variants exist for the target gene of SEQ ID No. 22; only the first variant is presented in the above table, but the second variant, the Genbank accession number of which is NM_198926, is just as relevant for the purpose of the present invention. Finally, eleven variants exist for the target gene of SEQ ID No. 25; only the first variant is presented in the above table, but the other variants, the Genbank accession numbers of which are NM_139002; NM_139003; NM_139004; NM_139005; NM_139006; NM_139007; NM_139008; NM_139009; NM_139010; NM_139011, are just as relevant for the purpose of the present invention.

To this effect, the present invention relates to a method for the diagnosis/prognosis of a septic syndrome based on a biological sample from a patient, characterized in that it comprises the following steps:
   a. biological material is extracted from the biological sample,
   b. the biological material is brought into contact with at least one specific reagent that is selected from specific reagents for the target genes with a nucleic sequence having any one of SEQ ID Nos 1 to 28,
   c. the expression of at least one of said target genes is determined.

For the purpose of the present invention, the term "biological sample" is intended to mean any sample taken from a patient, and liable to contain a biological material as defined hereinafter. This biological sample may in particular be a blood, serum, saliva, tissue or circulating-cell sample from the patient. This biological sample is provided by any type of sampling known to those skilled in the art. According to a preferred embodiment of the invention, the biological sample taken from the patient is a blood sample.

In step a) of the method according to the invention, the biological material is extracted from the biological sample by any of the nucleic acid extraction and purification protocols well known to those skilled in the art. For the purpose of the present invention, the term "biological material" is intended to mean any material that makes it possible to detect the expression of a target gene. The biological material may in particular comprise proteins, or nucleic acids, such as, in particular, deoxyribonucleic acids (DNA) or ribonucleic acids (RNA). The nucleic acid may in particular be an RNA (ribonucleic acid). According to a preferred embodiment of the invention, the biological material extracted in step a) comprises nucleic acids, preferably RNAs, and even more preferably total RNA. Total RNA comprises transfer RNAs, messenger RNAs (mRNAs), such as the mRNAs transcribed from the target gene, but also transcribed from any other gene, and ribosomal RNAs. This biological material comprises material specific for a target gene, such as in particular the mRNAs transcribed from the target gene or the proteins derived from these mRNAs, but can also comprise material not specific for a target gene, such as in particular the mRNAs transcribed from a gene other than the target gene, tRNAs, rRNAs derived from genes other than the target gene.

By way of indication, the nucleic acid extraction can be carried out by:
- a step consisting of lysis of the cells present in the biological sample, in order to release the nucleic acids contained in the cells of the patient. By way of example, use may be made of the methods of lysis as described in patent applications:
  - WO 00/05338 regarding mixed magnetic and mechanical lysis,
  - WO 99/53304 regarding electrical lysis,
  - WO 99/15321 regarding mechanical lysis.

Those skilled in the art may use other well-known methods of lysis, such as thermal or osmotic shocks or chemical lyses using chaotropic agents such as guanidinium salts (U.S. Pat. No. 5,234,809);
- a purification step, for separating the nucleic acids from the other cellular constituents released in the lysis step. This generally makes it possible to concentrate the nucleic acids, and can be adapted to the purification of DNA or of RNA. By way of example, use may be made of magnetic particles optionally coated with oligonucleotides, by adsorption or covalence (in this respect, see U.S. Pat. No. 4,672,040 and U.S. Pat. No. 5,750,338), and the nucleic acids which are bound to these magnetic particles can thus be purified by means of a washing step. This nucleic acid purification step is particularly advantageous if it is desired to subsequently amplify said nucleic acids. A particularly advantageous embodiment of these magnetic particles is described in patent applications: WO-A-97/45202 and WO-A-99/35500. Another advantageous example of a nucleic acid purification method is the use of silica, either in the form of a column, or in the form of inert particles (Boom R. et al., J. Clin. Microbiol., 1990, no 28 (3), p. 495-503) or magnetic particles (Merck: MagPrep® Silica, Promega: MagneSil™ Paramagnetic particles). Other very widely used methods are based on ion exchange resins in a column or in paramagnetic particulate format (Whatman: DEAE-magarose) (Levison P R et al., J. Chromatography, 1998, p. 337-344). Another method that is very relevant, but not exclusive, for the invention is that of adsorption onto a metal oxide carrier (company Xtrana: Xtra-Bind™ matrix).

When the intention is to specifically extract the DNA from a biological sample, it is possible in particular to carry out an extraction with phenol, chloroform and alcohol in order to remove the proteins, and to precipitate the DNA with 100% ethanol. The DNA can then be pelleted by centrifugation, washed and resolubilized.

When the intention is to subsequently extract the RNAs from a biological sample, it is possible in particular to carry out an extraction with phenol, chloroform and alcohol in order to remove the proteins, and to precipitate the RNAs with 100% ethanol. The RNAs can then be pelleted by centrifugation, washed and resolubilized.

In step b), and for the purposes of the present invention, the term "specific reagent" is intended to mean a reagent which, when it is brought into contact with biological material as defined above, binds with the material specific for said target gene. By way of indication, when the specific reagent and the biological material are of nucleic origin, bringing the specific reagent into contact with the biological material allows the specific reagent to hybridize with the material specific for the target gene. The term "hybridization" is intended to mean the process during which, under appropriate conditions, two nucleotide fragments bind with stable and specific hydrogen bonds so as to form a double-stranded complex. These hydrogen bonds form between the complementary adenine (A) and thymine (T) (or uracil (U)) bases (this is referred to as an A-T bond) or between the complementary guanine (G) and cytosine (C) bases (this is referred to as a G—C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds that make it possible to form the double-stranded complex, but also bases not bound to a complementary base. The hybridization between two nucleotide fragments depends on the working conditions that are used, and in particular on the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concencentration of denaturing agents and/or the hybridization temperature. All these data are well known and the appropriate conditions can be determined by those skilled in the art. In general, depending on the length of the nucleotide fragments that it is intended to hybridize, the hybridization temperature is between approximately 20 and 70° C., in particular between 35 and 65° C. in a saline solution at a concentration of approximately 0.5 to 1 M. A sequence, or nucleotide fragment, or oligonucleotide, or polynucleotide, is a series of nucleotide motifs assembled together by phosphoric ester bonds, characterized by the informational sequence of the natural nucleic acids, capable of hybridizing to a nucleotide fragment, it being possible for the series to contain monomers having different structures and to be obtained from a natural nucleic acid molecule and/or by genetic recombination and/or by chemical synthesis. A motif is a derivative of a monomer which may be a natural nucleotide of nucleic acid, the constitutive elements of which are a sugar, a phosphate group and a nitrogenous base; in DNA, the sugar is deoxy-2-ribose, in RNA, the sugar is ribose; depending on whether DNA or RNA is involved, the nitrogenous base is selected from adenine, guanine, uracil, cytosine and thymine; alternatively the monomer is a nucleotide that is modified in at least one of the three constitutive elements; by way of example, the modification may occur either at the level of the bases, with modified bases such as inosine, methyl-5-deoxycytidine, deoxyuridine, dimethylamino-5-deoxyuridine, diamino-2,6-purine, bromo-5-deoxyuridine or any other modified base capable of hybridization, or at the level of the sugar, for example the replacement of at least one deoxyribose with a polyamide (P. E. Nielsen et al, Science, 254, 1497-1500 (1991)), or else at the level of the phosphate group, for example its replacement with esters in particular selected from diphosphates, alkyl- and arylphosphonates and phosphorothioates.

According to a specific embodiment of the invention, the specific reagent comprises at least one amplification primer. For the purpose of the present invention, the term "amlification primer" is intended to mean a nucleotide fragment comprising from 5 to 100 nucleic motifs, preferably from 15 to 30 nucleic motifs that allow the initiation of an enzymatic polymerization, for instance an enzymatic amplification reaction. The term "enzymatic amplification reaction" is intended to mean a process which generates multiple copies of a nucleotide fragment through the action of at least one enzyme. Such amplification reactions are well known to those skilled in the art and mention may in particular be made of the following techniques:

- PCR (polymerase chain reaction), as described in U.S. Pat. No. 4,683,195, U.S. Pat. No. 4,683,202 and U.S. Pat. No. 4,800,159,
- LCR (ligase chain reaction), disclosed, for, example, in patent application EP 0 201 184,
- RCR (repair chain reaction), described in patent application WO 90/01069,
- 3SR (self sustained sequence replication) with patent application WO 90/06995,
- NASBA (nucleic acid sequence-based amplification) with patent application WO 91/02818, and
- TMA (transcription mediated amplification) with U.S. Pat. No. 5,399,491.

When the enzymatic amplification is a PCR, the specific reagent comprises at least two amplification primers, specific for a target gene, that allow the amplification of the material specific for the target gene. The material specific for the target gene then preferably comprises a complementary DNA obtained by reverse transcription of messenger RNA derived from the target gene (reference is then made to target-gene-specific cDNA) or a complementary RNA obtained by transcription of the cDNAs specific for a target gene (reference is then made to target-gene-specific cRNA). When the enzymatic amplification is a PCR carried out after a reverse transcription reaction, reference is made to RT-PCR.

According to another preferred embodiment of the invention, the specific reagent of step b) comprises at least one hybridization probe.

The term "hybridization probe" is intended to mean a nucleotide fragment comprising at least 5 nucleotide motifs, such as from 5 to 100 nucleic motifs, in particular from 10 to 35 nucleic motifs, having a hybridization specificity under given conditions so as to form a hybridization complex with the material specific for a target gene. In the present invention, the material specific for the target gene may be a nucleotide sequence included in a messenger RNA derived from the target gene (reference is then made to target-gene-specific mRNA), a nucleotide sequence included in a complementary DNA obtained by reverse transcription of said messenger RNA (reference is then made to target-gene-specific cDNA), or else a nucleotide sequence included in a complementary RNA obtained by transcription of said cDNA as described above (reference will then be made to target-gene-specific cRNA). The hybridization probe may include a label for its detection. The term "detection" is intended to mean either a direct detection by a physical method, or an indirect detection by a method of detection using a label. Many methods of detection exist for detecting nucleic acids [see, for example, Kricka et al., Clinical Chemistry, 1999, no 45 (4), p. 453-458 or Keller G. H. et al., DNA Probes, 2nd Ed., Stockton Press, 1993, sections 5 and 6, p. 173-249]. The term "label" is intended to mean a tracer capable of generating a signal that can be detected. A nonlimiting list of these tracers includes enzymes which produce a signal that can be detected, for example, by colorimetry, fluorescence or luminescence, such as horseradish peroxidase, alkaline phosphatase, beta-galactosidase, glucose-6-phosphate dehydrogenase; chromophores such as fluorescent, luminescent or dye compounds; electron dense groups detectable by electron microscopy or by virtue of their electrical properties such as conductivity, by amperometry or voltametry methods, or by impedance measurement; groups that can be detected by optical methods such as diffraction, surface plasmon resonance, or contact angle variation, or by physical methods such as atomic force spectroscopy, tunnel effect, etc.; radioactive molecules such as $^{32}P$, $^{35}S$ or $^{125}I$.

For the purpose of the present invention, the hybridization probe may be a "detection" probe. In this case, the "detection" probe is labeled by means of a label as defined above. The detection probe may in particular be a "molecular beacon" detection probe as described by Tyagi & Kramer (Nature biotech, 1996, 14:303-308). These "molecular beacons" become fluorescent during the hybridization. They have a stem-loop-type structure and contain a fluorophore and a "quencher" group. The binding of the specific loop sequence with its complementary target nucleic acid sequence causes the stem to unroll and the emission of a fluorescent signal during excitation at the appropriate wavelength.

For the detection of the hybridization reaction, use may be made of target sequences that have been labeled, directly (in particular by the incorporation of a label within the target sequence) or indirectly (in particular using a detection probe as defined above). It is in particular possible to carry out, before the hybridization step, a step consisting in labeling and/or cleaving the target sequence, for example using a labeled deoxy-ribonucleotide triphosphate during the enzymatic amplification reaction. The cleavage may be carried out in particular by the action of imidazole or of manganese chloride. The target sequence may also be labeled after the amplification step, for example by hybridizing a detection probe according to the sandwich hybridization technique described in document WO 91/19812. Another specific preferred method of labeling nucleic acids is described in application FR 2 780 059.

According to a preferred embodiment of the invention, the detection probe comprises a fluorophore and a quencher. According to an even more preferred embodiment of the invention, the hybridization probe comprises an FAM (6-carboxy-fluorescein) or ROX (6-carboxy-X-rhodamine) fluorophore at its 5' end and a quencher (Dabsyl) at its 3' end.

The hybridization probe may also be a "capture" probe. In this case, the "capture" probe is immobilized or can be immobilized on a solid substrate by any appropriate means, i.e. directly or indirectly, for example by covalence or adsorption. As solid substrate, use may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate. The term "biochip" is intended to mean a solid substrate that is small in size, to which a multitude of capture probes are attached at predetermined positions. The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of capture probes attached to a solid substrate, on which probes a sample of target nucleotide fragments directly or indirectly labeled with fluorochromes is made to act. The capture probes are positioned specifically on the substrate or chip and each hybridization gives a specific piece of information, in relation to the target nucleotide fragment. The pieces of information obtained are cumulative, and make it possible, for example, to quantify the level of expression of one or more target genes. In order to analyze the expression of a target gene, a substrate comprising a multitude of probes, which correspond to all or part of the target gene, which is transcribed to mRNA, can then be prepared. For the purpose of the present invention, the term "low-density substrate" is intended to mean a substrate comprising fewer than 50 probes. For the purpose of the present invention, the term "medium-density substrate" is intended to mean a substrate comprising from 50 probes to 10 000 probes. For the purpose of the present invention, the term "high-density substrate" is intended to mean a substrate comprising more than 10 000 probes.

The cDNAs or cRNAs specific for a target gene that it is desired to analyze are then hybridized, for example, to specific capture probes. After hybridization, the substrate or chip is washed and the labeled cDNA or cRNA/capture probe complexes are revealed by means of a high-affinity ligand bound, for example, to a fluorochrome-type label. The fluorescence is read, for example, with a scanner and the analysis of the fluorescence is processed by information technology. By way of indication, mention may be made of the DNA chips developed by the company Affymetrix ("Accessing Genetic Information with High-Density DNA arrays", M. Chee et al., Science, 1996, 274, 610-614. "Light-generated oligonucleotide arrays for rapid DNA sequence analysis", A. Caviani Pease et al., Proc. Natl. Acad. Sci. USA, 1994, 91, 5022-5026), for molecular diagnoses. In this technology, the capture probes are generally small in size, around 25 nucleotides. Other examples of biochips are given in the publications by G. Ramsay, Nature Biotechnology, 1998, No. 16, p. 40-44; F. Ginot, Human Mutation, 1997, No. 10, p. 1-10; J. Cheng et al, Molecular diagnosis, 1996, No. 1 (3), p. 183-200; T. Livache et al, Nucleic Acids Research, 1994, No. 22 (15), p. 2915-2921; J. Cheng et al, Nature Biotechnology, 1998, No. 16, p. 541-546 or in U.S. Pat. No. 4,981,783, U.S. Pat. No. 5,700,637, U.S. Pat. No. 5,445,934, U.S. Pat. No. 5,744,305 and U.S. Pat. No. 5,807,522. The main characteristic of the solid substrate should be to conserve the hybridization characteristics of the capture probes on the target nucleotide fragments while at the same time generating a minimum background noise for the method of detection. Three main types of fabrication can be distinguished for immobilizing the probes on the substrate.

First of all, there is a first technique which consists in depositing presynthesized probes. The attachment of the probes is carried out by direct transfer, by means of micropipettes or of microdots or by means of an inkjet device. This technique allows the attachment of probes having a size ranging from a few bases (5 to 10) up to relatively large sizes of 60 bases (printing) to a few hundred bases (microdeposition):

Printing is an adaptation of the method used by inkjet printers. It is based on the propulsion of very small spheres of fluid (volume <1 nl) at a rate that may reach 4000 drops/second. The printing does not involve any contact between the system releasing the fluid and the surface on which it is deposited.

Microdeposition consists in attaching long probes of a few tens to several hundred bases to the surface of a glass slide. These probes are generally extracted from databases and are in the form of amplified and purified products. This technique makes it possible to produce chips called microarrays that carry approximately ten thousand spots, called recognition zones, of DNA on a surface area of a little less than 4 $cm^2$. The use of nylon membranes, referred to as "macroarrays", which carry products that have been amplified, generally by PCR, with a diameter of 0.5 to 1 mm and the maximum density of which is 25 spots/$cm^2$, should not however be forgotten. This very flexible technique is used by many laboratories. In the present invention, the latter technique is considered to be included among biochips. A certain volume of sample can, however, be deposited at the bottom of a microtitration plate, in each well, as in the case in patent applications WO-A-00/71750 and FR 00/14896, or a certain number of drops that are separate from one another can be deposited at the bottom of one and the same Petri dish, according to another patent application, FR 00/14691.

The second technique for attaching the probes to the substrate or chip is called in situ synthesis. This technique results in the production of short probes directly at the surface of the chip. It is based on in situ oligonucleotide synthesis (see, in particular, patent applications WO 89/10977 and WO 90/03382) and is based on the oligonucleotide synthesizer process. It consists in moving a reaction chamber, in which the oligonucleotide extension reaction takes place, along the glass surface.

Finally, the third technique is called photolithography, which is a process that is responsible for the biochips developed by Affymetrix. It is also an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers ($\mu m^2$). This resolution makes it possible to create up to several hundred thousand spots on a surface area of a few square centimeters ($cm^2$). Photolithography has advantages: in bulk in parallel, it makes it possible to create a chip of N-mers in only 4×N cycles. All these techniques can be used with the present invention. According to a preferred embodiment of the invention, the at least one specific reagent of step b) defined above comprises at least one hybridization probe which is preferably immobilized on a substrate. This substrate is preferably a low-, high- or medium-density substrate as defined above.

These hybridization steps on a substrate comprising a multitude of probes may be preceded by an enzymatic amplification reaction step, as defined above, in order to increase the amount of target genetic material.

In step c), the determination of the expression of a target gene can be carried out by any of the protocols known to those skilled in the art.

In general, the expression of a target gene can be analyzed by detecting the mRNAs (messenger RNAs) that are transcribed from the target gene at a given moment or by detecting the proteins derived from these mRNAs.

The invention preferably relates to the determination of the expression of a target gene by detection of the mRNAs derived from this target gene according to any of the protocols well known to those skilled in the art. According to a specific embodiment of the invention, the expression of several target genes is determined simultaneously, by detection of several different mRNAs, each mRNA being derived from a target gene.

When the specific reagent comprises at least one amplification primer, it is possible, in step c) of the method according to the invention, to determine the expression of the target gene in the following way:

1) After having extracted, as biological material, the total RNA (comprising the transfer RNAs (tRNAs), the ribosomal RNAs (rRNAs) and the messenger RNAs (mRNAs)) from a biological sample as presented above, a reverse transcription step is carried out in order to obtain the complementary DNAs (or cDNAs) of said mRNAs. By way of indication, this reverse transcription reaction can be carried out using a reverse transcriptase enzyme which makes it possible to obtain, from an RNA fragment, a complementary DNA fragment. The reverse transcriptase enzyme from AMV (Avian Myoblastosis Virus) or from MMLV (Moloney Murine Leukaemia Virus) can in particular be used. When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex which then serves as a starting point for the reverse transcription reaction carried out by the reverse transcriptase enzyme. cDNAs complementary to the mRNAs derived from a target gene (target-gene-specific cDNA) and cDNAs complementary to the mRNAs derived from genes other than the target gene (cDNAs not specific for the target gene) are then obtained.

2) The amplification primer(s) specific for a target gene is (are) brought into contact with the target-gene-specific cDNAs and the cDNAs not specific for the target gene. The amplification primer(s) specific for a target gene hybridize(s) with the target-gene-specific cDNAs and a predetermined region, of known length, of the cDNAs originating from the mRNAs derived from the target gene is specifically amplified. The cDNAs not specific for the target gene are not amplified, whereas a large amount of target-gene-specific cDNAs is then obtained. For the purpose of the present invention, reference is made, without distinction, to "target-gene-specific cDNAs" or to "cDNAs originating from the mRNAs derived from the target gene". This step can be carried out in particular by means of a PCR-type amplification reaction or by any other amplification technique as defined above. By PCR, it is also possible to simultaneously amplify several different cDNAs, each one being specific for different target genes, by using several pairs of different amplification primers, each one being specific for a target gene: reference is then made to multiplex amplification.

3) The expression of the target gene is determined by detecting and quantifying the target-gene-specific cDNAs obtained in step 2) above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal. These electrophoresis techniques are well known to those skilled in the art. The target-gene-specific cDNAs can also be detected and quantified using a quantification range obtained by means of an amplification reaction carried out until saturation. In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By realizing a ratio of the expression of the target gene to the expression of the housekeeping gene, i.e. by realizing a ratio of the amount of target-gene-specific cDNAs to the amount of housekeeping-gene-specific cDNAs, any variability between the various experiments is thus corrected. Those skilled in the art may refer in particular to the following publications: Bustin S A, *J Mol Endocrinol*, 2002, 29: 23-39; Giulietti A *Methods*, 2001, 25: 386-401.

When the specific reagent comprises at least one hybridization probe, the expression of a target gene can be determined in the following way:

1) After having extracted, as biological material, the total RNA from a biological sample as presented above, a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene).

2) All the cDNAs are brought into contact with a substrate, on which are immobilized capture probes specific for the target gene whose expression it is desired to analyze, in order to carry out a hybridization reaction between the target-gene-specific cDNAs and the capture probes, the cDNAs not specific for the target gene not hybridizing to the capture probes. The hybridization reaction can be carried out on a solid substrate which includes all the materials as indicated above. According to a preferred embodiment, the hybridization probe is immobilized on a substrate. Preferably, the substrate is a low-, high- or medium-density substrate as defined above. The hybridization reaction may be preceded by a step consisting of enzymatic amplification of the target-gene-specific cDNAs as described above, so as to obtain a large amount of target-gene-specific cDNAs and to increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812. Other preferred specific methods for labeling and/or cleaving nucleic acids are described in applications WO 99/65926, WO 01/44507, WO 01/44506, WO 02/090584, WO 02/090319.

3) A step consisting of detection of the hybridization reaction is subsequently carried out. The detection can be carried out by bringing the substrate on which the capture probes specific for the target gene are hybridized with the target-gene-specific cDNAs into contact with a "detection" probe labeled with a label, and detecting the signal emitted by the label. When the target-gene-specific cDNA has been labeled beforehand with a label, the signal emitted by the label is detected directly.

When the at least one specific reagent brought into contact in step b) of the method according to the invention comprises at least one hybridization probe, the expression of a target gene can also be determined in the following way:

1) After having extracted, as biological material, the total RNA from a biological sample as presented above, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The cRNAs of the cDNAs of the mRNAs specific for the target gene (reference is then made to target-gene-specific cRNA) and the cRNAs of the cDNAs of the mRNAs not specific for the target gene are then obtained.

2) All the cRNAs are brought into contact with a substrate on which are immobilized capture probes specific for the target gene whose expression it is desired to analyze, in order to carry out a hybridization reaction between the target-gene-specific cRNAs and the capture probes, the cRNAs not specific for the target gene not hybridizing to the capture probes. When it is desired to simultaneously analyze the expression of several target genes, several different capture probes can be immobilized on the substrate, each one being specific for a target gene. The hybridization reaction may also be preceded by a step consisting in labeling and/or cleaving the target-gene-specific cRNAs as described above.

3) A step consisting of detection of the hybridization reaction is subsequently carried out. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate of biochip type on which a large number of probes are hybridized is used.

According to a specific embodiment of the invention, steps B and C are carried out at the same time. This preferred method can in particular be carried out by "real time NASBA", which groups together, in a single step, the NASBA amplification technique and real-time detection which uses "molecular beacons". The NASBA reaction takes place in the tube, producing the single-stranded RNA with which the specific "molecular beacons" can simultaneously hybridize to give a fluorescent signal. The formation of the new RNA molecules is measured in real time by continuous verification of the signal in a fluorescent reader. Unlike an RT-PCR amplification, NASBA amplification can take place in the presence of DNA in the sample. It is not therefore necessary to verify that the DNA has indeed been completely eliminated during the RNA extraction.

The analysis of the expression of a target gene selected from any one of SEQ ID Nos 1 to 28 then makes it possible to have a tool for the diagnosis/prognosis of a septic syndrome.

Preferably, the target genes of SEQ ID Nos 1, 2, 4-8, 11 and 16 make it possible to distinguish the two groups of patients.

It is, for example, possible to analyze the expression of a target gene in a patient for whom the prognosis is not known, and to compare with known mean expression values for the target gene in patients with a good prognosis (GP) and known mean expression values for the target gene in patients with a poor prognosis (PP), in order to provide the patient with a suitable treatment.

According to another preferred embodiment, in step b), the biological material is brought into contact with at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 specific reagents that are selected from specific reagents for the target genes with a nucleic sequence having any one of SEQ ID Nos 1 to 28, and, in step c), the expression of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 of said target genes is determined.

More particularly, the inventors have demonstrated that the simultaneous analysis of the expression of a panel of 28 genes as defined above is very relevant for discriminating between GP patients and PP patients. In this respect, the invention also relates to a method as defined above, characterized in that it comprises the following steps:
  a. biological material is extracted from the biological sample,
  b. the biological material is brought into contact with at least 28 specific reagents that are selected from specific reagents for the target genes with a nucleic sequence having any one of SEQ ID Nos 1 to 28,
  c. the expression of at least 28 of said target genes is determined.

The expression of a panel of 22 specific genes, comprising the genes of SEQ ID Nos 1, 3, 7, 9-15, and 17-28, makes it possible, in this respect, to obtain excellent results since it makes it possible to correctly categorize 92% of patients with a good prognosis and 100% of patients with a poor prognosis. In this respect, the invention relates to a method for the diagnosis/prognosis of a septic syndrome based on a biological sample from a patient, characterized in that it comprises the following steps:
  a. biological material is extracted from the biological sample,
  b. the biological material is brought into contact with at least 22 specific reagents that are selected from specific reagents for the target genes with a nucleic sequence having any one of SEQ ID Nos 1, 3, 7, 9-15 and 17-28,
  c. the expression of at least 22 of said target genes is determined.

The use of a restricted panel of genes is particularly suitable for obtaining a prognostic tool. In fact, the analysis of the expression of about 20 genes does not require the custom-made fabrication of DNA chips, and can be carried out directly by PCR or NASBA techniques, or alternatively low-density chip techniques, which provides a considerable economic asset and a simplified implementation.

The invention also relates to a substrate, as defined above, comprising at least 28 hybridization probes selected from probes specific for the target genes with a nucleic sequence having any one of SEQ ID Nos 1 to 28.

According to another embodiment of the invention, the substrate comprises at least 22 hybridization probes selected from probes specific for the target genes with a nucleic sequence having any one of SEQ ID Nos 1, 3, 7, 9-15 and 17-28.

According to another embodiment of the invention, the substrate comprises at least one hybridization probe specific for at least one target gene with a nucleic sequence having any one of SEQ ID Nos 1 to 28, preferably at least one hybridization probe specific for at least one target gene with a nucleic sequence having any one of SEQ ID Nos 1, 2, 4-8, 11 and 16.

Finally, the invention relates to the use of a substrate as defined above, for the diagnosis/prognosis of a septic syndrome.

The invention also relates to the use of at least 28 specific reagents for the target genes with a nucleic sequence having any one of SEQ ID Nos 1 to 28 as defined above, for the diagnosis/prognosis of a septic syndrome. Preferably, the invention relates to the use of at least 22 specific reagents for the target genes with a nucleic sequence having any one of SEQ ID Nos 1, 3, 7, 9-15 and 17-28 as defined above, for the diagnosis/prognosis of a septic syndrome.

The invention also relates to the use of at least one specific reagent for the target genes with a nucleic sequence having any one of SEQ ID Nos 1, 2, 4-8, 11 and 16 as defined above, for the diagnosis/prognosis of a septic syndrome.

Finally, the invention relates to a kit for the diagnosis/prognosis of a septic syndrome, comprising a substrate as defined above.

The invention also relates to a kit for the diagnosis/prognosis of a septic syndrome, comprising at least 28 specific reagents for the target genes with a nucleic sequence having any one of SEQ ID Nos 1 to 28 as defined above, for the diagnosis/prognosis of a septic syndrome. Preferably, the invention relates to a kit for the diagnosis/prognosis of a septic syndrome, comprising at least 22 specific reagents for the target genes with a nucleic sequence having any one of SEQ ID Nos 1, 3, 7, 9-15 and 17-28 as defined above, for the diagnosis/prognosis of a septic syndrome.

The invention also relates to a kit for the diagnosis/prognosis of a septic syndrome, comprising at least one specific reagent for the target genes with a nucleic sequence having any one of SEQ ID Nos 1, 2, 4-8, 11 and 16 as defined above, for the diagnosis/prognosis of a septic syndrome.

Of course, all the definitions indicated above in the description apply for all the embodiments of the invention.

BRIEF DESCRIPTION OF DRAWINGS

The attached figure is given by way of explanatory example and is in no way limiting in nature. It will make it possible to understand the invention more completely.

Figure 1:
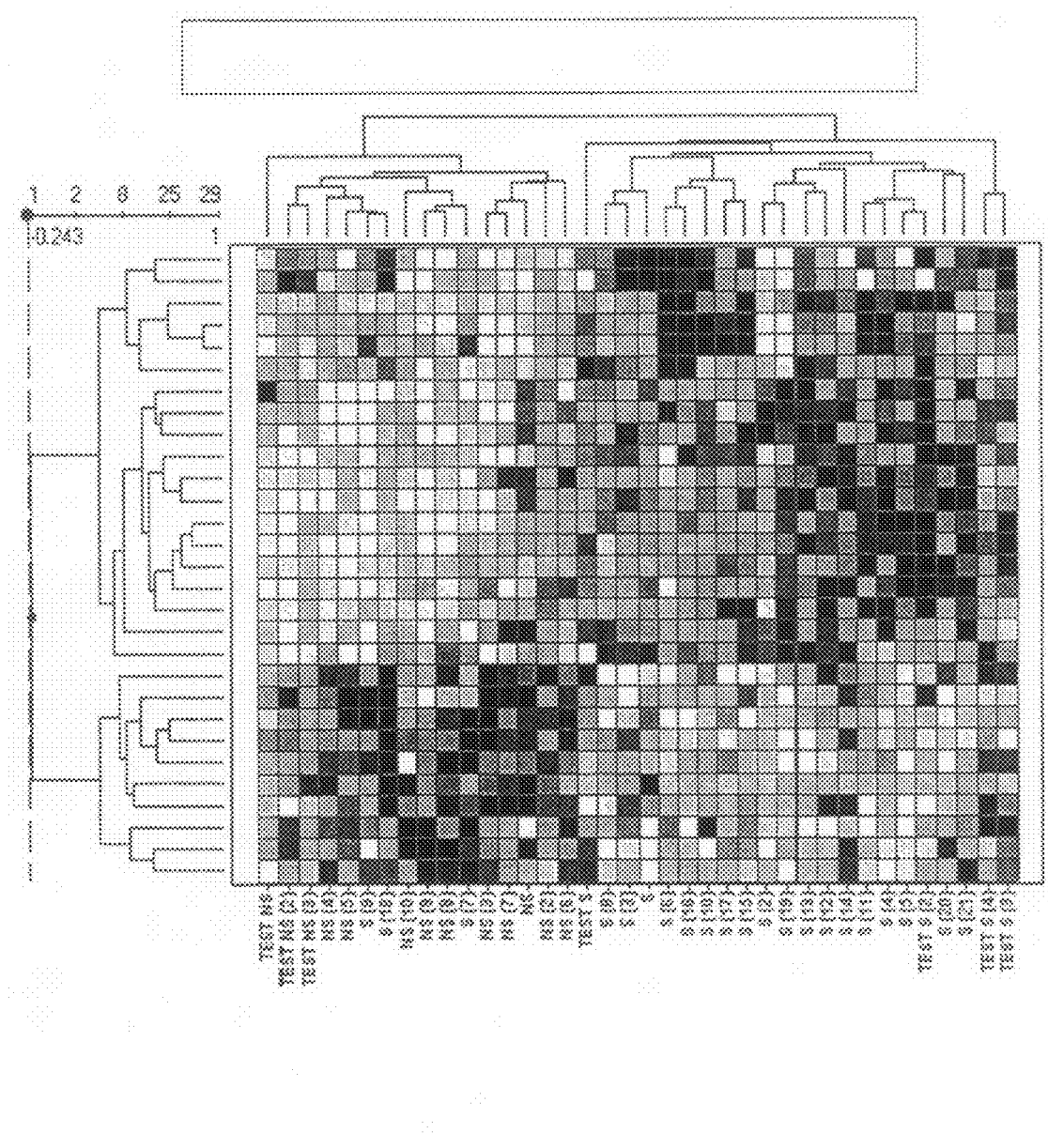
FIG. 1 represents an analysis of hierarchical clustering of 38 blood samples obtained from 13 PP patients (also called NS) and 26 GP patients (also called S), using the expression of 28 genes according to the invention, measured with 29 probe sets on the Affymetrix biochip. The hierarchical clustering function of the Spofire software organizes the PP and GP patients in columns, and the genes in rows so as to obtain in adjacent positions the patients or the genes with comparable expression profiles. Pearson's correlation coefficient was used as a similarity index for the genes and the patients. Subsequently, firstly the unweighted pair group method using arithmetic averages, UPGMA, clustering method and, secondly, the mean value of all the samples made it possible to organize the patients and the genes, respectively. The results correspond to the Affymetrix fluorescence level normalized with the <<Affy>> software. In order to take into account the constitutive differences in expression between the genes, the levels of expression of each gene were normalized by applying a reduced centered normal law. The white represents the low levels of expression, the gray the intermediate levels and the black the high levels. The height of the branches of the dendogram indicates the index of similarity between the expression profiles.

The following examples are given by way of illustration and are in no way limiting in nature. They will make it possible to understand the invention more fully.

EXAMPLE 1

Search for an Expression Profile for the Diagnosis/Prognosis of a Septic Syndrome Characteristics of the biological samples: The study was carried out on patients having developed a septic syndrome, and admitted into the surgical or medical intensive care unit of the Lyon-Sud hospital center. In order to be included in the study, the patients had to present the following criteria: over 18 years of age; presence of a septic shock according to the consensus conference previously described; absence of comorbidity (metastatic cancer, malignant hemopathy, type I diabetes, chronic hepatic pathology, chronic renal insufficiency, AIDS). Since the objective of the study was to study the late mortality induced by a septic shock, the patients who died over the first 48 hours of the syndrome were excluded from the study. The treatment for all the patients included was similar.

Taking the day of the first administration of catecholamine to be D1 of the septic shock, each patient was monitored for a maximum period of 28 days. On the basis of the mortality observed over this period, a group of 10 patients (PP) and a group of 21 patients (GP) were studied. Subsequently, the gene panel according to the invention was validated blind using two groups of patients recruited on the basis of the same criteria: one group of. 3 PP patients and one group of 4 GP patients. The genomic analyses were carried out using samples obtained between D2 and D4. The demographic characteristics of the entire cohort are presented in the following table:

|  | GP | | PP | | | |
| --- | --- | --- | --- | --- | --- | --- |
|  | Train<br>n = 21 (%) | Test<br>n = 4 (%) | Train<br>n = 10 (%) | Test<br>n = 3 (%) | Total<br>n = 38 (%) | P[a] |
| Men | 13 (62) | 2 (50) | 7 (70) | 1 (33) | 23 (61) | 0.930 |
| Women | 8 (38) | 2 (50) | 3 (30) | 2 (67) | 15 (39) |  |
| Age (years)[b] | 67 (49-71) | 71 (66-75) | 68 (57-79) | 78 (63-80) | 67 (54-78) | 0.371 |
| SAPS II at admission[b] | 48 (40-55) | 45 (37-52) | 61 (59-73) | 61 (60-72) | 55 (42-61) | <0.001 |
| Duration of hospitalization in ICU.[b] | 12 (10-26) | 32 (28-34) | 9 (8-14) | 4 (4-10) | 12 (9-25) | 0.013 |
| COPD | 1 (5) | 2 (50) | 3 (30) | 1 (33) | 7 (18) | 0.203 |
| MacCabe and           0 | 7 (33) | 1 (25) | 0 | 0 | 8 (21) | 0.045 |
| Jackson criteria      1 | 9 (43) | 2 (50) | 9 (90) | 1 (33) | 21 (55) |  |
|                       2 | 5 (24) | 1 (25) | 0 | 2 (67) | 8 (21) |  |
|                       3 | 0 | 0 | 1 (10) | 6 | 1 (3) |  |
| Microbiologically documented diagnosis | 15 (71) | 4 (100) | 7 (70) | 3 (100) | 29 (76) | >0.999 |
|            In Gram(−) Bacillus | 8 (38) | 1 (25) | 3 (30) | 3 (100) | 15 (39) | 0.950 |
|            In Gram(+) Cocci | 7 (33) | 1 (25) | 5 (50) | 1 (33) | 14 (37) |  |
|            Fungal | 6 (29) | 1 (25) | 3 (30) | 1 (33) | 11 (29) |  |
| Type of infection    Community-acquired | 7 (33) | 4 (100) | 5 (50) | 1 (33) | 17 (45) | 0.900 |
|                      Hospital-acquired | 14 (67) | 0 (0) | 5 (50) | 2 (67) | 21 (55) |  |
| Site of the infection   Pulmonary | 6 (29) | 2 (50) | 8 (80) | 1 (33) | 17 (45) | 0.061 |
|                         Abdominal | 12 (57) | 1 (25) | 2 (20) | 2 (67) | 17 (45) |  |
|                         Others | 3 (14) | 1 (25) | 0 (0) | 0 (0) | 4 (11) |  |

[a]comparison between the overall population of survivors (n = 25) and non-survivors (n = 13)
[b]Median (Q1-Q3)
COPD: chronic obstructive pulmonary disease Extraction of the Biological Material (Total RNA) from the Biological Sample:

The samples were collected directly in PAXGene™ Blood RNA tubes (PreAnalytix, Frankin Lakes, USA). After the step consisting in taking the blood sample and in order to obtain total lysis of the cells, the tubes were left at ambient temperature for 4 h and then stored at −20° C. until the extraction of the biological material. More specifically, in this protocol, the total RNA was extracted using the PAX-Gene Blood RNA® kits (PreAnalytix) while observing the manufacturer's recommendations. Briefly, the tubes were centrifuged (10 min, 3000 g) in order to obtain a pellet of nucleic acid. This pellet was washed and taken up in a buffer containing proteinase K required for digestion of the proteins (10 min at 55° C.). A further centrifugation (5 min, 19 000 g) was carried out in order to remove the cell debris, and ethanol was added in order to optimize the nucleic acid binding conditions. The total RNA was specifically bound to PAXGene RNA spin columns and, before elution of the latter, a digestion of the contaminating DNA was carried out using the RNAse-free DNAse set (Qiagen Ltd, Crawley, UK). The quality of the total RNA was analyzed with the AGILENT 2100 bioanalyzer (Agilent Technologies, Waldbronn, Germany). The total RNA comprises the transfer RNAs, the messenger RNAs (mRNAs) and the ribosomal RNAs.

Synthesis of cDNA, obtaining of cRNAs, labeling of cRNAs and quantification: In order to analyze the expression of the target genes according to the invention, the complementary DNAs (cDNAs) of the mRNAs contained in the total RNA as purified above were obtained from 5 μg of total RNA, using 400 units of the SuperScriptII reverse transcription enzyme (Invitrogen) and 100 pmol of poly-T primer containing the T7 promoter (T7-oligo(dT) 24-primer, Proligo, Paris, France). The cDNAs thus obtained were then extracted with phenol/chloroform and precipitated with ammonium acetate and ethanol and redissolved in 24 μl of DEPC water. A 20 μl volume of this purified solution of cDNA was subsequently subjected to in vitro transcription using a T7 RNA polymerase which specifically recognizes the promoter of the T7 polymerase as mentioned above. This transcription makes it possible to obtain the cRNA of the cDNA. This transcription was carried out using a Bioarray High Yield RNA Transcript Labeling Kit (Enzo Diagnostics, Farmingdale, N.Y.), which not only makes it possible to obtain the cRNA, but also allows the incorporation of biotinylated cytidine and uridine bases during the synthesis of the cRNA.

The purified cRNAs were subsequently quantified by spectrophotometry, and the cRNA solution was adjusted to a concentration of 1 μg/μl of cRNA. The step consisting of cleavage of these cRNAs was subsequently carried out at 94° C. for 35 min, using a fragmentation buffer (40 mM of tris acetate, pH 8.1, 100 mM of potassium acetate, 30 mM of magnesium acetate) in order to bring about the hydrolysis of the cRNAs and to obtain fragments of 35 to 200 bp. The success of such a fragmentation was verified by 1.5% agarose gel electrophoresis.

Demonstration of a Differential Expression Profile Between the PP and GP Patients:

For this, 20 μg of fragmented cRNAs derived from each sample were added to a hybridization buffer (Affymetrix) and 200 μl of this solution were brought into contact for 16 h at 45° C. on an expression chip (Human Genome U133A GeneChip® (Affymetrix)), which comprises 22 283 groups of probes representing approximately 14 500 genes according to the Affymetrix protocol as described on the Affymetrix internet site. In order to record the best hybridization and washing performance levels, RNAs described as "control" RNAs, that were biotinylated (bioB, bioC, bioD and cre), and oligonucleotides (oligo B2) were also included in the hybridization buffer. After the hybridization step, the solution of cRNA biotinylated and hybridized on the chip was visualized using a solution of streptavidin-phycoerythrin and the signal was amplified using an anti-streptavidin antibody. The hybridization was carried out in a "GeneChip hybridization oven" (Affymetrix), and the Euk GE-WS2V4 protocol of the Affymetrix protocol was followed. The washing and visualization steps were carried out on a "Fluidics Station 450" (Affymetrix). Each U133A chip was subsequently analyzed on an Agilent G2500A GeneArray Scanner at a resolution of 3 microns in order to pinpoint the areas hybridized on the chip. This scanner makes it possible to detect the signal emitted by the fluorescent molecules after excitation with an argon laser using the epifluorescence microscope technique. A signal proportional to the amount of cRNAs bound is thus obtained for each position. The signal was subsequently analyzed using the Microarray Suite 5.0 software (MAS5.0, Affymetrix).

In order to prevent the variations obtained by using various chips, an overall normalization approach was carried out using the MAS5.0 software (Affymetrix), which, by virtue of a statistical algorithm, makes it possible to define whether or not a gene was expressed. In order to be able to compare the chips with one another, the raw data (".CELL" file) were processed by means of a quantile normalization step using the "Affy" package of the "R" software (Gautier, L. et al., Bioinformatics (2004), p. 307-315). Each gene represented on the U133A chip was covered by 11 pairs of probes of 25 oligonucleotides. The term "pair of probes" is intended to mean a first probe which hybridized perfectly (reference is then made to PM or perfect match probes) with one of the cRNAs derived from a target gene, and a second probe, identical to the first probe with the exception of a mismatch (reference is then made to MM or mismatched probe) at the center of the probe. Each MM probe was used to estimate the background noise corresponding to a hybridization between two nucleotide fragments of non-complementary sequence (Affymetrix technical note "Statistical Algorithms Reference Guide"; Lipshutz, et al (1999) Nat. Genet. 1 Suppl., 20-24). The 38 samples of the study showed an average of 38.1±4.2% of expressed genes.

The analysis of the expression data was carried out using the Microsoft Excel software, the Spotfire decision site for functional genomics V7.1 software (Spotfire A B, Gothenburg, Sweden), and a statistical algorithm: the genetic algorithm (Gautier, L. et al., Bioinformatics (2004), p. 307-315; Ooi, C. H. and Tan, P. Bioinformatics (2003), p. 37-44).

Based on the 22 283 groups of probes, representing approximately 14 500 genes, of the chip, the inventors duly selected the relevant genes that made it possible to differentiate between the PP patients and the GP patients.

For this, a first step consisted in excluding the genes exhibiting a level of expression comparable between all the groups of patients. Four steps were carried out:
- the genes not expressed in all the patients were excluded (MAS5.0 software).
- the genes for which the fluorescence median was less than 30 in the two groups were excluded;
- the genes that were not expressed in at least 30% of the patients in one of the two groups were excluded;
- the genes for which the ratio of the expression medians between the GP and PP patients was between 0.77 and 1.3 were excluded.

Subsequent to the application of these filters, a group of 2216 groups of probes was selected and was used as a working base for a multiparametric analysis with the Genetic Algorithm.

Results obtained: a list of 28 genes was identified. The increase or the decrease in expression of each of these genes, observed in the PP patients compared with the BP patients, is indicated in table 2.

TABLE 2

List of 28 genes differentially expressed in PP and GP patients

| SEQ ID N° | Gene name | Abbreviated name | Expression in PP versus GP |
|---|---|---|---|
| 1 | chemokine (C-X3-C motif) receptor 1 | CX3CR1 | Increased* |
| 2 | T cell receptor delta diversity 3 | TRDD3 | Increased£ |
| 3 | KIAA0882 protein | KIAA0882 | Increased |
| 4 | T-cell lymphoma invasion and metastasis 1 | TIAM1 | Increased£ |
| 5 | Interleukin 1, beta | IL1B | Increased* |
| 6 | Carbonyl reductase 1 | CBR1 | Increased£ |
| 7 | TIR domain containing molecule 1 | TRIF | Increased* |
| 8 | FYN tyrosine kinase protooncogene | FYN | Increased£ |
| 9 | Heparanase | HPSE | Increased |
| 10 | SRY (Sex determining region Y) box 4 | SOX4 | Increased£ |
| 11 | Interleukin 2 receptor, beta | IL2RB | Increased* |
| 12 | Raft-linking protein | RAFTLIN | Increased |
| 13 | CGI-40 protein Homo sapiens SID1 transmembrane family, member 2 | CGI-40 SIDT2 | Increased |
| 14 | glucose-6-phosphatase catalytic subunit 3 | G6PC3 | Increased |
| 15 | Mannosidase alpha, class 1A member 2 | MAN1A2 | Increased |
| 16 | Myeloid differentiation primary response gene (88) | MYD88 | Increased* |
| 17 | Ribosomal protein L6 | RPL6 | Increased |
| 18 | Ribosomal protein L10a | RPL10a | Increased |
| 19 | sin3-associated polypeptide, 30 kDa | SAP30 | Decreased |
| 20 | Mitogen activated protein kinase-activated protein kinase 2 | MAPKAPK2 | Decreased |
| 21 | Presenilin enhancer 2 | PEN2 | Decreased |
| 22 | Hypothetical protein LOC55924 | LOC55924 | Decreased |
| 23 | Solute carrier family 39 (zinc transporter member 7) | SLC39A7 | Decreased£ |
| 24 | Glutathione peroxidase 3 (plasma) | GPX3 | Decreased£ |
| 25 | Hemochromatosis | HFE | Decreased |
| 26 | Transcriptional activator of the cfos promoter | CROC4 | Decreased |
| 27 | peroxisomal biogenesis factor 6 | PEX6 | Decreased |
| 28 | Huntingtin interacting protein | | Decreased |

The indication of an * and £ indicate respectively a statistically different difference between the two groups according to a T test with Bonferroni or Benjamini and Hochberg correction, respectively. This indicates that these genes taken in isolation are very relevant in the diagnosis/prognosis of a septic syndrome.

Validation by Quantitative RT-PCR

In order to confirm these results by means of another molecular biology technique, certain genes were assayed by quantitative RT-PCR. Briefly, a reverse transcription (RT) reaction was carried out in a final volume of 20 µl. The total RNA (1 µg) was mixed with 1 µl of polyT at 50 µM and 1 µl of DNTP mix (ThermoScript™ RT-PCR system, Invitrogen), and then incubated for 5 min at 65° C. After cooling in ice, the solution was mixed with 4 µl of 5×cDNA synthesis buffer, 1 µl of RNAse out (40 U/µl), 1 µl of DEPC-treated water and 1 µl of Thermoscript RT (15 U/µl), all these products being derived from the ThermoScript™ RT-PCR system (Invitrogen). The reverse transcription was carried out for 1 h at 50° C. and then stopped by incubation at 85° C. for 5 min. To finish, each cDNA solution was diluted to 1/10 in DEPC water. For each of the genes of interest, a standard was prepared by means of a PCR (polymerase chain reaction) amplification carried out until saturation. The amplicons obtained were purified (PCR purification kit, Qiagen Ltd) and the presence of a unique amplicon was verified by agarose gel electrophoresis and ethidium bromide staining. The standard consisting of the peptidylpropyl isomerase B (PPIB)<<housekeeping>> gene encoding cycophilin B was obtained from Search-LC (Heidelberg, Germany).

Analysis of mRNA Expression by Real Time PCR

The mRNAs of the target genes of SEQ ID Nos 1, 5, 11 and 16 were quantified by real time quantitative PCR using the LightCycler™ (Roche). The PCR reactions were carried out using the Fast-Start™ DNA Master SYBR Green I real-time PCR kit (Roche Molecular Biochemicals). Each PCR was carried out in a final volume of 20 µl containing 1 µl of LC-Fast Start Reaction Mix SYBR Green I, 1 µl of LC-Fast Start DNA Master SYBR Green I/Enzyme (including the Taq DNA polymerase, the reaction buffer and a deoxynucleotide triphosphate mix), $MgCl_2$ (final concentration of 3 mM), the sense and antisense primers (final concentration of 0.5 µM), and 10 µl of cDNA solution. After a denaturation step of 10 min at 95° C., the amplification was carried out by means of 40 cycles of a "touch-down" PCR protocol (10 s at 95° C., 10 s of hybridization at 68-58° C., followed by an extension of 16 s at 72° C.). At the end of each cycle, the fluorescence emitted by the SYBR Green was measured.

In order to confirm the specificity of the amplification, the PCR products were systematically subjected to a melting curve analysis (LightCycler™—Roche). For this, the PCR products were treated with an increase in temperature of from 58 to 98° C., with an increase of 0.1° C./s. For each PCR product, a single peak was obtained in the analysis of the curve, characterized by a specific melting point.

The combinations of primers required for the quantification of the PPIB housekeeping gene and IL-1β gene (SEQ ID No. 5) were obtained from Search-LC (Heidelberg, Germany). For PPIB, the Genbank accession no. was M60857 and the 105-338 region was amplified. For IL-1β, the Genbank accession no. was M15330 and the 438-642 region was amplified. The pairs of primers used to quantitatively determine the target genes of SEQ ID Nos 1, 11 and 16, the Genbank sequence used as reference and the position of the amplicons are described in the table below.

| TARGET GENE OF SEQ ID No. | | | | amplicon |
|---|---|---|---|---|
| 1 | Sense primer 5'-->3' | SEQ ID No. 29 | TGACTGGCAGATCCAGAGGTT | 164 bases |
|   | Antisense primer 5'-->3 | SEQ ID No. 30 | GTAGAATATGGACAGGAACAC |   |
| 11 | Sense primer 5'-->3' | SEQ ID No. 31 | CCTGAAGTGTAACACCCCAGA | 162 bases |
|   | Antisense primer 5'-->3 | SEQ ID No. 32 | TCCCTCTCCAGCACTTCTAGT |   |
| 16 | Sense primer 5'-->3' | SEQ ID No. 33 | TGCTGGAGCTGGGACCCAGCATTGAGGAGGA | 280 bases |
|   | Antisense primer 5'-->3 | SEQ ID No. 34 | TCAGACACACACAACTTCAGTCGATAG |   |

The amount of target mRNA relative to the amount of mRNA of the PPIB housekeeping gene was analyzed by the relative quantification technique with the LightCycler Relative Quantification Software (Roche Molecular Biochemicals). The "Second Derivative Maximum Method" of the LightCycler™ (Roche) was used to automatically determine the crossing point (Cp) for each sample. The value of the Cp was defined as the number of cycles for which the fluorescence was significantly different than the background noise.

Five serial 10-fold dilutions were carried out in quadruplicate with each standard in order to generate a standard curve expressing the Cp as a function of the logarithm of the number of copies. The standard dilutions were optimized so that the standard curve covered the expected level of expression for the target gene and the housekeeping gene. The relative standard curves describing the PCR efficiency for the target gene and the housekeeping gene were generated and used to perform a quantification with the LightCycler Relative Quantification Software (Roche Molecular Biochemicals).

The results obtained for the quantitative determination of the mRNAs of the target genes of SEQ ID Nos 1, 5, 11 and 16 by quantitative RT-PCR are given in table 3 below. The results correspond to 25 samples (8 PP and 17 GP). The correlation of the results obtained, firstly, with the biochip and, secondly, with the quantitative RT-PCR technique was established by means of Spearman's correlation test.

TABLE 3

Comparison of the levels of expression of 4 genes between Affymetrix and quantitative RT-PCR

| Abbreviated gene name | median Affymetrix GP | median Affymetrix PP | median RT-PCR GP | median RT-PCR PP | Spearman correlation coefficient: r | Spearman test degree of significance: p |
|---|---|---|---|---|---|---|
| CX3CR1 | 582.965 | 92.995 | 0.04295 | 0.00663 | 0.94 | <0.001 |
| IL-1β | 227.64 | 113.4 | 0.329 | 0.18 | 0.83 | <0.001 |
| IL-2Rβ | 204.86 | 131.965 | 0.00075 | 0.00024 | 0.76 | <0.001 |
| MyD88 | 2644.03 | 1986.315 | 0.0351 | 0.0294 | 0.56 | <0.01 |

For the 4 genes analyzed, a significant correlation was observed between the Affymetrix results and the quantitative RT-PCR results, confirming the relevance of the genes according to the invention.

Figure 2:
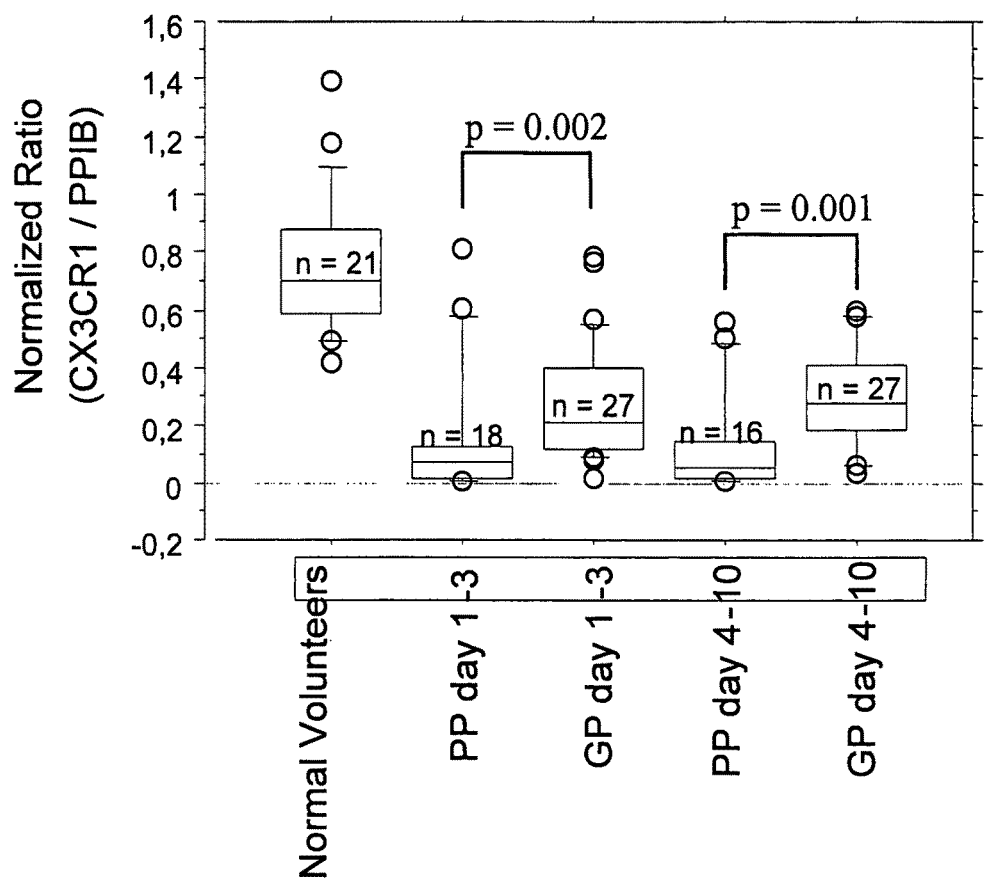
FIG. 2 presents the quantification of CX3CR1 mRNA in the blood of patients in septic shock. The gene expression level was measured by quantitative RT-PCR in 50 patients in septic shock (19 PP and 21 GP) and 21 normal volunteers. The results were normalized to the level of expression of the PPEB housekeeping gene. The results are presented with the median, the 25th percentile and the 75th percentile. Statistical comparison between the GP and PP was carried out by virtue of the nonparametric Mann-Whitney test.

By following the same protocol as that described in the above paragraphs, the CX3CR1 mRNAs were quantified from blood samples taken from 50 patients in septic shock (19 PP and 21 GP). A blood sample was obtained during the first 72 hours after the beginning of the shock, and then a second sample was obtained later on in the course of the syndrome. The level of expression of CX3CR1 was normalized to that of the PPIB housekeeping gene. The results are given in FIG. 2. The comparison between GP and PP was carried out using the nonparametric Mann-Whitney test. It is therefore particularly advantageous to analyze the expression of CX3CR1 mRNA as a poor prognosis factor.

Figure 3:
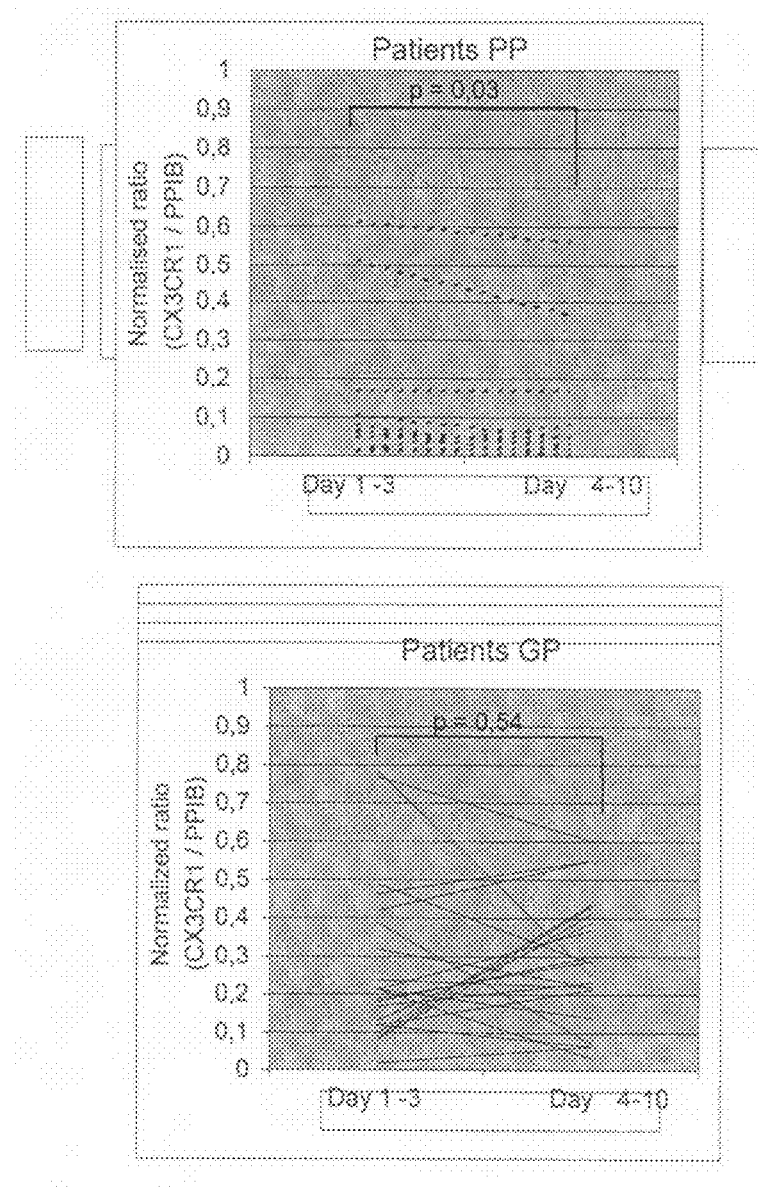
FIG. 3 presents the quantification of CX3CR1 mRNAs quantified in the blood of patients in septic shock. The gene expression level was measured by quantitative RT-PCR in 37 patients in septic shock (12 PP and 21 GP). For each patient, a PAXgene sample was obtained between D1 and D3 and another between D4 and D10. The results were normalized to the level of expression of the PPIB housekeeping gene. The evolution of the gene expression level of CX3CR1 between D1-D3 and D4-D10 in the PP and GP was performed by virtue of the nonparameteric Wilcoxon test.

The level of expression of the CX3CR1 mRNA showed a significant decrease over time in the PP patients. The results are given in FIG. 3. The evolution of the expression over time was tested using the Wilcoxon test.

It is therefore particularly advantageous to follow the expression of the CX3CR1 mRNA over time in order to confirm this poor prognosis.

Analysis of the Expression of a Panel of Genes

The inventors also demonstrated that the simultaneous analysis of the expression of several genes was very relevant for discriminating between GP and PP patients.

The inventors thus demonstrated that the simultaneous analysis of the expression of the 28 genes described above was very relevant for discriminating between the two GP and PP groups.

The results are given in FIG. 1. This list made it possible to clusterize 88% of the samples from GP patients in one group and 100% of the samples from PP patients in another group.

In addition, the inventors demonstrated that the simultaneous analysis of the expression of the genes of SEQ ID Nos 1, 3, 7, 9-15 and 17-28, among the 28 described above, was also particularly relevant for discriminating between the two GP and PP groups. The results are given in FIG. 2. This list made it possible to clusterize 92% of the samples from GP patients in one group and 100% of the samples from PP patients in another group.

Among the 28 genes described above, each of the 9 genes of SEQ ID Nos 1, 2, 4-8, 11 and 16 makes it possible to discriminate between the two groups of patients. Table 4 represents the p value calculated using the T test with Bonferroni or Benjamini and Hochberg correction. All these genes were overexpressed in the GP compared with the PP.

TABLE 4

Genes for discriminating between the two groups of patients.

| Gene name | Gene Symbol | Bonferroni correction | BHFDR correction | Fold change |
|---|---|---|---|---|
| Chemokine (C-X3-C motif) receptor 1 | CX3CR1 | 6.3E−05 | 6.3E−05 | 8.33 |
| T cell receptor delta diversity 3 | TRDD3 | >0.05 | 4.4E−02 | 4.00 |
| T-cell lymphoma invasion and metastasis 1 | TIAM1 | >0.05 | 2.7E−02 | 2.08 |
| Interleukin 1, beta | IL1B | 4.9E−02 | 9.7E−03 | 2.08 |
| Carbonyl reductase 1 | CBR1 | >0.05 | 2.8E−02 | 1.89 |
| TIR domain containing adaptor inducing interferon-beta | TRIF | 5.3E−04 | 2.6E−04 | 1.72 |
| FYN tyrosine kinase protooncogene | FYN | >0.05 | 2.7E−02 | 1.67 |
| Interleukin 2 receptor, beta | IL2RB | 4.3E−02 | 9.7E−03 | 1.52 |
| Myeloid differentiation primary response gene (88) | MYD88 | 3.5E−02 | 9.7E−03 | 1.37 |

What is claimed is:

1. A method comprising:
    obtaining a blood sample from a patient;
    measuring an expression level of a target gene comprising the nucleic acid sequence of SEQ ID NO: 1 in the blood sample obtained from the patient;
    performing cluster analysis of the target gene expression level of the patient with expression levels of the target gene from human patients that survived a septic syndrome and expression levels of the target gene from human patients that did not survive a septic syndrome;
    determining that the target gene expression level of the patient clusters with the expression levels of the target gene from the patients that did not survive a septic syndrome to identify the patient as having a decreased chance of survival; and
    treating the patient having the decreased chance of survival with an antibiotic and/or activated protein C.

2. The method according to claim 1, further comprising measuring expression levels of target genes respectively comprising the nucleic acid sequences of SEQ ID NOs: 3, 7, 9-15, and 17-28 in the blood sample.

3. The method according to claim 1, further comprising measuring expression levels of target genes respectively comprising the nucleic acid sequences of SEQ ID NOs: 2, 4-8, 11, and 16 in the blood sample.

4. The method according to claim 1, further comprising measuring expression levels of target genes respectively comprising the nucleic acid sequences of SEQ ID NOs: 2-28 in the blood sample.

5. The method according to claim 1, further comprising extracting biological material from the blood sample.

6. The method according to claim 5, wherein the expression level is measured by contacting the biological material with a reagent specific for an expression product of SEQ ID NO: 1.

7. The method according to claim 6, further comprising detecting hybridization of the specific reagent to the expression product.

8. The method according to claim 6, wherein the specific reagent comprises a hybridization probe.

9. The method according to claim 8, wherein the hybridization probe is immobilized on a substrate.

10. The method according to claim 5, wherein the biological material comprises nucleic acids.

11. The method according to claim 2, wherein the expression levels of 22 target genes in the blood sample are measured.

12. The method according to claim 1, wherein the expression levels of 28 target genes in the blood sample are measured.

13. The method according to claim 4, wherein no more than 50 specific reagents are used to measure expression levels of the target genes in the blood sample.

14. The method according to claim 1, further comprising monitoring the expression level of SEQ ID NO: 1 over time.

* * * * *